US009289416B2

(12) United States Patent
Gruening et al.

(10) Patent No.: US 9,289,416 B2
(45) Date of Patent: Mar. 22, 2016

(54) PHARMACEUTICAL DOSAGE FORMS COMPRISING 6'-FLUORO-(N-METHYL- OR N,N-DIMETHYL-)-4-PHENYL-4',9'-DIHYDRO-3'H-SPIRO[CYCLOHEXANE-1,1'-PYRANO[3,4,B]INDOL]-4-AMINE

(71) Applicant: Gruenenthal GmbH, Aachen (DE)

(72) Inventors: Nadja Gruening, Aachen (DE); Marc Schiller, Aachen (DE); Ashish Hemani, Wiltshire (GB); Chris Kirby, Reading (GB); Ingo Friedrich, Aachen (DE); John Bothmer, Heerlen (NL); Andreas Scholz, Giessen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 14/579,401

(22) Filed: Dec. 22, 2014

(65) Prior Publication Data

US 2015/0111939 A1  Apr. 23, 2015

Related U.S. Application Data

(62) Division of application No. 13/198,182, filed on Aug. 4, 2011.

(60) Provisional application No. 61/370,643, filed on Aug. 4, 2010, provisional application No. 61/370,634, filed on Aug. 4, 2010, provisional application No. 61/370,648, filed on Aug. 4, 2010.

(30) Foreign Application Priority Data

Aug. 4, 2010 (EP) .................................... 10008115
Aug. 4, 2010 (EP) .................................... 10008116
Aug. 4, 2010 (EP) .................................... 10008117

(51) Int. Cl.
*A61K 31/40* (2006.01)
*A61K 31/407* (2006.01)
*A61K 9/107* (2006.01)
*A61K 9/48* (2006.01)

(52) U.S. Cl.
CPC ............. *A61K 31/407* (2013.01); *A61K 9/1075* (2013.01); *A61K 9/4866* (2013.01)

(58) Field of Classification Search
USPC .......................................... 514/411; 548/427
See application file for complete search history.

(56) References Cited

U.S. PATENT DOCUMENTS

| | | | |
|---|---|---|---|
| 5,356,896 A | 10/1994 | Kabadi et al. | |
| 7,951,948 B2 | 5/2011 | Hinze et al. | |
| 8,293,758 B2 * | 10/2012 | Zemolka et al. | 514/278 |
| 2001/0004459 A1 | 6/2001 | Barthelemy et al. | |
| 2006/0004034 A1 * | 1/2006 | Hinze et al. | 514/278 |
| 2006/0193914 A1 | 8/2006 | Ashworth et al. | |
| 2007/0048228 A1 | 3/2007 | Arkenau-Maric et al. | |
| 2008/0125475 A1 | 5/2008 | Linz et al. | |
| 2009/0163716 A1 | 6/2009 | Hinze et al. | |
| 2010/0151028 A1 | 6/2010 | Ashworth et al. | |
| 2011/0015220 A1 | 1/2011 | Linz et al. | |

FOREIGN PATENT DOCUMENTS

| | | |
|---|---|---|
| CA | 2 595 954 A1 | 8/2006 |
| CN | 1633307 A | 6/2005 |
| CN | 1671419 A | 9/2005 |
| CN | 1735619 A | 2/2006 |
| CN | 100560061 C | 11/2009 |
| EA | 200601570 A1 | 2/2007 |
| ES | 2 333 956 T3 | 3/2010 |
| ES | 2 351 528 T3 | 2/2011 |
| JP | 2006-508114 A | 3/2006 |
| RU | 2 278 657 C2 | 6/2006 |
| RU | 2 354 656 C2 | 5/2009 |
| TW | 200940541 A1 | 10/2009 |
| TW | 201209059 A1 | 3/2012 |
| WO | WO 03/055466 A1 | 7/2003 |
| WO | WO 03/105906 A1 | 12/2003 |
| WO | WO 2004/043967 A1 | 5/2004 |
| WO | WO 2005/062722 A2 | 7/2005 |
| WO | WO 2005/087194 A1 | 9/2005 |
| WO | WO 2006/082099 A1 | 8/2006 |
| WO | WO 2008/040481 A1 | 4/2008 |

OTHER PUBLICATIONS

K. H. Bauer et al., "Lehrbuch der Pharmazeutischen Technologie", Wissenschaftliche Verlagsgesellschaft mbH Stuttgart, 1999, 6th Edition (table of contents) (Eight (8) pages).
R. Griffith et al., "Tablet crushing and the law: the implications for nursing", Professional Nurse, Sep. 2003, vol. 19, No. 1, pp. 41-42 (Two (2) pages).
C. M. Lopes et al., "Compressed Matrix Core Tablet as a Quick/Slow Dual-Component Delivery System Containing Ibuprofen", AAPS PharmSciTech, 2007, vol. 8, No. 3, Article 76, pp. E1-E8, (http://www.aapspharmscitech.org) (Eight (8) pages).
H. Miller et al., "To Crush or not to Crush—What to consider before giving medications to a patient with a tube or who has trouble swallowing", Nursing 2000, Feb. 2000, vol. 30, No. 2, pp. 50-52 (Three (3) pages).
J. F. Mitchell, "Oral Dosage Forms That Should Not Be Crushed : 2000 Update", Hospital Pharmacy, May 2000, vol. 35, No. 5, pp. 553-567 (Fifteen (15) pages).
S. Sahin et al., "The Operational Multiple Dosing Half-life : A Key to Defining Drug Accumulation in Patients and to Designing Extend Release Dosage Forms", Pharmaceutical Research, Dec. 2008, vol. 25, No. 12, pp. 2869-2877 (Nine (9) pages).

(Continued)

Primary Examiner — Rei-Tsang Shiao
(74) Attorney, Agent, or Firm — Crowell & Moring LLP

(57) ABSTRACT

A pharmaceutical dosage form for administration twice daily, once daily or less frequently, which contains 6'-fluoro-(N-methyl- or N,N-dimethyl)-4-phenyl-4',9'-dihydro-3'H-spiro[cyclohexane-1,1'-pyrano[3,4,b]indol]-4-amine or a physiologically acceptable salt thereof.

30 Claims, 10 Drawing Sheets

(56) References Cited

OTHER PUBLICATIONS

Shargel et al. "Applied Biopharmaceuticals & Pharmacokinetics", $5^{th}$ Edition, 2005, (table of contents) (Eight (8) pages).

Patel et al., "Self-Emulsifying Drug Delivery Systems," Jul. 2, 2008, Advanstar (seven (7) pages).

Jingli, 2005, pp. 47-48 (two (2) pages).

Jingli, "The Main Ways to Improve the Dissolution of Tablets," 2005 (two (2) pages).

"Shin Yakuzaigaku Souron," (Introduction to Modern Pharmaceutics), Revised $3^{rd}$ Edition, 1987, pp. 357-359, with English-language translation (six (6) pages).

R.M. Dannenfelser et al., "Development of Clinical Dosage Forms for a Poorly Water Soluble Drug 1: Application of Polyethylene Glycol-Polysorbate 80 Solid Dispersion Carrier System," Journal of Pharmaceutical Sciences, vol. 93, No. 5 (May 2004), pp. 1165-1175.

P. Sudheer et al., "Approaches to Development of Solid—Self Micron Emulsifying Drug Delivery System: Formulation techniques and Dosage Forms—A Review," Asian Journal of Pharmacy and Life Science, vol. 2, No. 2 (Apr.-Jun. 2012), pp. 214-225.

S.D. Mandawgade et al., "Development of SMEDDS Using Natural Lipophile: Application to β-Artemether Delivery," International Journal of Pharmaceutics 362 (2008), pp. 179-183.

\* cited by examiner

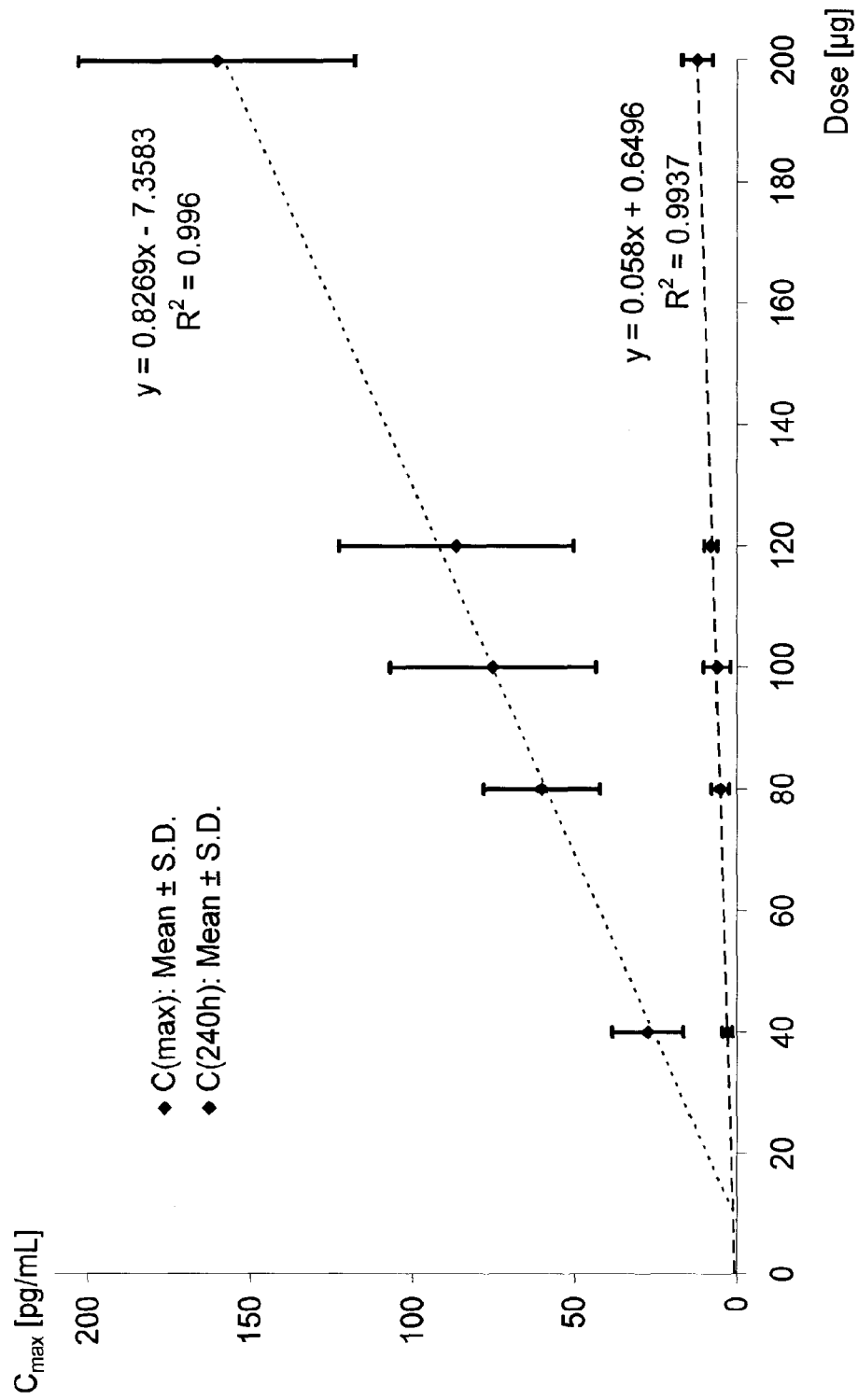

PHARMACEUTICAL DOSAGE FORMS COMPRISING 6'-FLUORO-(N-METHYL- OR N,N-DIMETHYL-)-4-PHENYL-4',9'-DIHYDRO-3'H-SPIRO[CYCLOHEXANE-1,1'-PYRANO[3,4,B]INDOL]-4-AMINE

FIELD OF THE INVENTION

The invention relates to a pharmaceutical dosage form for preferably oral administration twice daily, once daily or less frequently, which contains a pharmacologically active agent according to general formula (I)

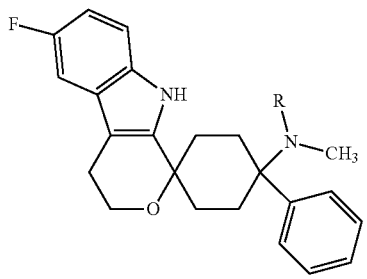

(I)

wherein R is —H or —CH$_3$, or a physiologically acceptable salt thereof.

The invention also relates to the use of a pharmaceutical dosage form for preferably oral administration once daily, which contains a pharmacologically active agent according to general formula (I)

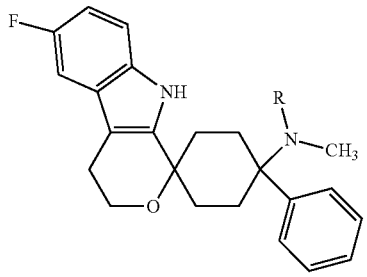

(I)

wherein R is —H or —CH$_3$, or a physiologically acceptable salt thereof, in the treatment of neuropathic pain, preferably chronic neuropathic pain.

The invention additionally relates to the use of a pharmaceutical dosage form for preferably oral administration once daily, which contains a pharmacologically active agent according to general formula (I)

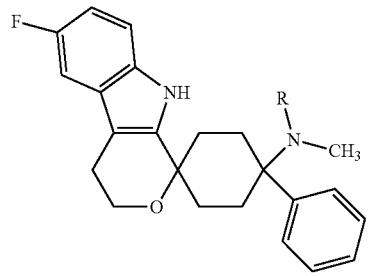

(I)

wherein R is —H or —CH$_3$, or a physiologically acceptable salt thereof, in the treatment of nociceptive pain, preferably acute or chronic nociceptive pain.

The pharmacologically active agents according to general formula (I) can also be referred to as 6'-fluoro-(N-methyl- or N,N-dimethyl-)-4-phenyl-4',9'-dihydro-3'H-spiro[cyclohexane-1,1'-pyrano[3,4,b]indol]-4-amine. Unless expressly stated otherwise, this term also includes the physiologically acceptable salts.

BACKGROUND OF THE INVENTION

The pharmacologically active agents according to the invention are known from the prior art and can be administered orally, perorally, parenterally, intravenously, intraperitoneally, intradermally, intramuscularly, intrathecally, epidurally, intranasally, buccally, rectally or locally, for example to the skin, the mucous membranes or into the eyes. The compounds exhibit analgesic properties and are particularly suitable for the treatment of acute, visceral, neuropathic or chronic pain (cf., e.g., WO 2004/043967 and WO 2008/040481).

Conventional analgesics are typically available as formulations providing immediate release or as formulations providing prolonged release.

On the one hand, formulations providing immediate release upon oral administration have the advantage that they lead to a fast release of the analgesic in the gastrointestinal tract. As a result, a comparatively high dose of the analgesic is quickly absorbed leading to high plasma levels within a short period of time and resulting in a rapid onset of pain relief, i.e. analgesic action begins shortly after administration. This is particularly desirable in acute pain.

At the same time, however, a rapid reduction in the analgesic action is usually observed, because metabolization and/or distribution and/or excretion of the analgesic cause a decrease of its plasma levels. For that reason, formulations providing immediate release of analgesics typically need to be administered frequently, e.g. eight times per day. This is not only detrimental with respect to patient compliance but also may cause comparatively high peak plasma drug concentrations and high fluctuations between peak and trough plasma drug concentrations which in turn may deteriorate tolerability.

On the other hand, formulations providing prolonged release upon oral administration have the advantage that they need to be administered less frequently, typically once daily or twice daily. This improves patient compliance and also can reduce peak plasma drug concentrations and fluctuations between peak and trough plasma drug concentrations which in turn may improve tolerability.

At the same time, however, release of the analgesic in the gastrointestinal tract is prolonged. As a result, a comparatively low dose of the analgesic is quickly absorbed leading to low plasma levels and resulting in a retarded onset of pain relief, i.e. analgesic action begins quite a while after first administration.

Furthermore, as formulations providing prolonged release typically contain higher doses of the analgesics than formulations providing immediate release, they bear a higher risk of being misused. Older patients in particular frequently have difficulties in taking solid pharmaceutical dosage forms. Further, most elderly require adaptations in dosages due to different ADME (absorption, distribution, metabolism excretion) characteristics in age which is another reason for the need of breakable tablets. To counter this problem, various apparatuses have been developed by means of which solid pharmaceutical dosage forms may be comminuted or pulverized ("tablet crushers"). Such apparatuses are used, for example, by the care staff in old people's homes. The pharmaceutical dosage forms are then administered to the people being cared for not as tablets etc. but rather as powder, for example to get round the difficulties involved in swallowing tablets. However, the comminution of pharmaceutical dosage forms with such apparatuses is problematic if the pharmaceutical dosage forms are prolonged release formulations. As a rule, comminution then results in destruction of the inner structure of the pharmaceutical dosage form, which is responsible for the prolonged release, so doing away with the prolonged-release action. Consequently, after administration, frequently all the physiologically active substance originally contained in the pharmaceutical dosage form is released in a relatively short time, whereby a comparatively very high plasma concentration of the substance is abruptly reached for a relatively short period (dose dumping). In this way, the original prolonged-release formulations become immediate-release formulations. Depending on the physiological activity of the substance, this may cause considerable side-effects however, and in extreme cases may even lead to the death of the patient (cf., e.g., J. E. Mitchell, Oral Pharmaceutical dosage forms That Should Not Be Crushed: 2000 Update, Hospital Pharmacy, 2000; H. Miller et al., To Crush or Not to Crush, Nursing 2000; R. Griffith et al., Tablet Crushing and the law: the implications for nursing; Prof. Nurse 2003). Intentional chewing of prolonged-release formulations may also lead to an overdose of the substance contained therein. Sometimes patients chew the pharmaceutical dosage forms deliberately, though often in ignorance of the type and purpose of a prolonged-release formulation, because they hope for a quicker effect.

Formulations providing a dual release mode, i.e. a combination of immediate release with prolonged release, are also known (cf., e.g., C. M. Lopez et al., Compressed Matrix Core Tablet as a Quick/Slow Dual-Component Delivery System Containing Ibuprofen, AAPS PharmSciTech 2007; 8(3), E1-E8). However, these formulations typically rely upon immediate-release units and prolonged-release units that are locally separated from one another and therefore, such pharmaceutical dosage forms can only be prepared by specific and costly methods.

The treatment of chronic pain involves long-term analgesic treatment which often requires higher doses than those sufficient in acute pain episodes. In order to keep adverse events at a tolerable level, titration of the analgesic dose may be required at the start of therapy, especially when common μ-opioid analgesics such as morphine are employed. Accordingly, titrated long-term opioid therapy typically starts with sub-therapeutic doses which are gradually increased until adequate analgesia is reported.

It is an object of the invention to provide pharmaceutical dosage forms containing 6'-fluoro-(N-methyl- or N,N-dimethyl-)-4-phenyl-4',9'-dihydro-3'H-spiro[cyclohexane-1,1'-pyrano[3,4,b]indol]-4-amine which have advantages compared to the pharmaceutical dosage forms of the prior art. In particular, the pharmaceutical dosage forms should provide good bioavailability and rapid and adequate pain relief already after the first administration, but also should have a high tolerability, good compliance, and safety.

This object has been achieved by the invention as described and claimed hereinafter.

It has been found that 6'-fluoro-(N-methyl- or N,N-dimethyl-)-4-phenyl-4',9'-dihydro-3'H-spiro[cyclohexane-1,1'-pyrano[3,4,b]indol]-4-amine has a comparatively poor water solubility. Further, it has been found that in spite of said poor water solubility, pharmaceutical dosage forms can be prepared which provide immediate release of 6'-fluoro-(N-methyl- or N,N-dimethyl-)-4-phenyl-4',9'-dihydro-3'H-spiro [cyclohexane-1,1'-pyrano[3,4,b]indol]-4-amine and provide good bioavailability. Still further, it has been found that 6'-fluoro-(N-methyl- or N,N-dimethyl-)-4-phenyl-4',9'-dihydro-3'H-spiro[cyclohexane-1,1'-pyrano[3,4,b]indol]-4-amine has a relatively large pharmacokinetic terminal half life time ($t_{1/2} \approx 60\text{-}90$ h) and thus, provides pharmacological activity for a comparatively extended period of time after administration (the operational half life is about 24 h). For details concerning the terminal half life and the operational half life see e.g. to S. Sahin et al., *Pharm. Res.*, 2008, 25(12), 2869-2877.

Therefore, it has been surprisingly found that upon preferably oral administration of the pharmaceutical dosage form containing the pharmacologically active agent according to the invention, a rapid onset of pain relief can be achieved followed by a prolonged analgesic effect, although, or even if, the pharmaceutical dosage form provides immediate release. Therefore, the pharmaceutical dosage form according to the invention combines the advantageous properties of conventional formulations providing immediate release—e.g., rapid pain relief due to adequately high concentration of active ingredient just a short time (e.g., about one hour) after administration of the pharmaceutical composition—with the advantageous properties of conventional formulations providing prolonged release—e.g., long-lasting analgesic action owing to an adequately high level of active ingredient over a prolonged time —, and at the same time even overcomes the drawbacks of said conventional formulations. By taking the pharmacologically active agent in the formulation according to the invention, the patient can effectively combat his pain acutely and, at the same time, treat it effectively over a prolonged period without further measures and merely by regular administration at 12 (or e.g., 24) hourly intervals.

It is particularly surprising that the pharmaceutical dosage form according to the invention not only allows the pharmacologically active agent to start flowing rapidly in the plasma when the pharmaceutical dosage form is first administered, leading to a rapid onset of pain relief in the patient owing to the immediate release, but at the same time ensures long-lasting therapeutic efficacy over a relatively long period (at least 12 hours, preferably at least 24 hours). Therefore, the pain suffered by a patient can rapidly be alleviated when the pharmaceutical dosage form according to the invention is administered without the analgesic action quickly fading again.

Further, it has been surprisingly found that due to its large pharmacokinetic half-life, the highest plasma concentrations (peak plasma concentrations) of 6'-fluoro-(N-methyl- or N,N-dimethyl-)-4-phenyl-4',9'-dihydro-3'H-spiro[cyclohexane-1,1'-pyrano[3,4,b]indol]-4-amine are increased upon once daily administration of fixed dosages. The peak concentration ($C_{max}$) was observed surprisingly late, namely at about 4 to 6 hours after administration.

It has been surprisingly found that once daily administration of fixed, comparatively small doses of 6'-fluoro-(N-methyl- or N,N-dimethyl-)-4-phenyl-4',9'-dihydro-3'H-spiro[cyclohexane-1,1'-pyrano[3,4,b]indol]-4-amine, e.g. daily doses of 40 μg, leads to subtherapeutic peak plasma concentrations on the first day of therapy, but to therapeutic peak plasma concentrations later on. For example, in case of a daily dose of 40 μg, a substantial analgesic effect was observed in patients with painful diabetic neuropathy on the fourth and fifth day of once daily administration.

Moreover, it has been surprisingly found that at such comparatively small doses, the occurrence of side effects compared to morphine was considerably decreased under equianalgesic conditions.

These surprising effects suggest that during long-term therapy of neuropathic pain, preferably chronic neuropathic pain, the dose of 6'-fluoro-(N-methyl- or N,N-dimethyl-)-4-phenyl-4',9'-dihydro-3'H-spiro[cyclohexane-1,1'-pyrano[3,4,b]indol]-4-amine may generally be kept at a low level, not only initially but throughout the whole analgesic therapy and accordingly, undesired side-effects may be reduced or even fully suppressed. Dose titration during the initial administration phase may be possible but is not required necessarily.

The pharmaceutical dosage form according to the invention has good patient compliance and safety. Even if the pharmaceutical dosage form according to the invention is tampered with, e.g. by means of tablet crushers, dose dumping cannot occur—crushing the pharmaceutical dosage form does not further accelerate the immediate release profile. This finding is supported by the pharmacokinetic profiles of three different galenic formulations (solution in macrogol, self-emulsifying capsules filled with liquid, and tablets).

The invention relates to a pharmaceutical dosage form containing a pharmacologically active agent according to general formula (I)

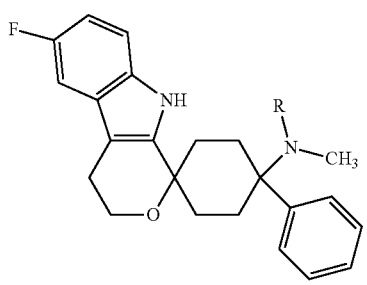

(I)

wherein R is —H or —CH$_3$,
or a physiologically acceptable salt thereof;
said pharmaceutical dosage form being for administration twice daily, once daily or less frequently.

The invention also relates to a pharmaceutical dosage form for administration once daily and containing a pharmacologically active agent according to general formula (I)

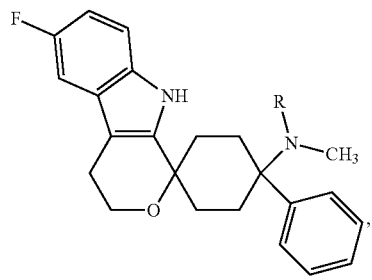

(I)

wherein R is —H or —CH$_3$,
or a physiologically acceptable salt thereof,
which provides immediate release in vitro of the pharmacologically active agent according to general formula (I) in accordance with Ph. Eur.; and
which contains the pharmacologically active agent according to general formula (I) in a dose of from 10 μg to 190 μg; and
wherein the pharmacokinetic parameter $t_{max}$ is within the range of from 0.5 to 16 h, for use in the treatment of neuropathic pain, preferably chronic neuropathic pain.

The invention additionally relates to a pharmaceutical dosage form for administration once daily and containing a pharmacologically active agent according to general formula (I)

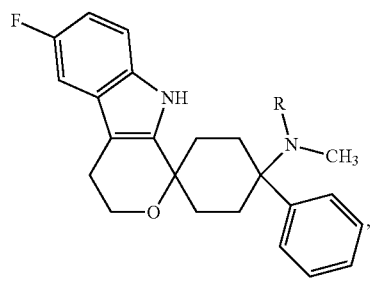

(I)

wherein R is —H or —CH$_3$,
or a physiologically acceptable salt thereof,
which provides immediate release in vitro of the pharmacologically active agent according to general formula (I) in accordance with Ph. Eur.; and
which contains the pharmacologically active agent according to general formula (I) in a dose of from 150 μg to 800 μg, preferably more than 190 μg to 800 μg; and
wherein the pharmacokinetic parameter $t_{max}$ is within the range of from 0.5 to 16 h, for use in the treatment of nociceptive pain, preferably acute or chronic nociceptive pain.

Unless expressly stated otherwise, all dosages concerning the pharmacologically active agent according to the invention are preferably expressed as weight equivalent dosages based upon the free base.

The pharmacologically active agent according to general formula (I) can also be referred to as "6'-fluoro-N-methyl-4-phenyl-4',9'-dihydro-3'H-spiro[cyclohexane-1,1'-pyrano[3,4,b]indol]-4-amine" when R is —H, and "6'-fluoro-N,N-dimethyl-4-phenyl-4',9'-dihydro-3'H-spiro[cyclohexane-1,1'-pyrano[3,4,b]indol]-4-amine" when R is —CH$_3$; for the purpose of the specification, the pharmacologically active agent according to general formula (I) can also be referred to as "6'-fluoro-(N-methyl- or N,N-dimethyl-)-4-phenyl-4',9'-dihydro-3'H-spiro[cyclohexane-1,1'-pyrano[3,4,b]indol]-4-amine".

In a preferred embodiment, the pharmacologically active agent according to general formula (I) has a stereochemistry according to general formula (I')

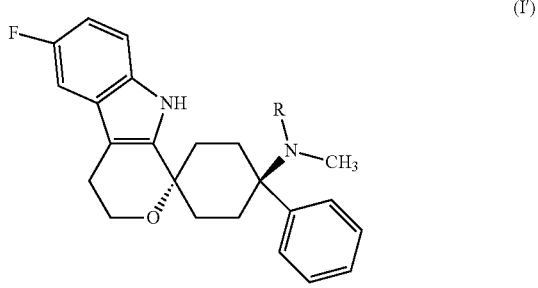
(I')

wherein R is —H or —CH₃, or a physiologically acceptable salt thereof.

In another embodiment of the pharmaceutical dosage form according to the invention, the compound of formula (I) is selected from

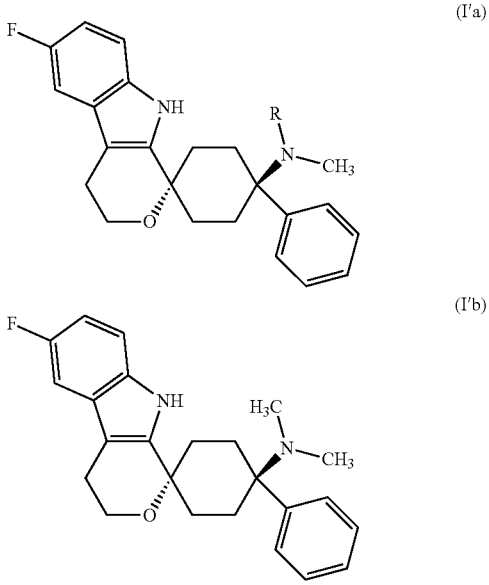

in the form of the free base or a physiologically acceptable salt thereof.

The free base according to general formula (I'a) can be systematically referred to as "1,1-(3-methylamino-3-phenyl-pentamethylene)-6-fluoro-1,3,4,9-tetrahydropyrano[3,4-b]indole (trans)" or as "(1r,4r)-6'-fluoro-N-methyl-4-phenyl-4',9'-dihydro-3'H-spiro[cyclohexane-1,1'-pyrano[3,4,b]indol]-4-amine", respectively.

The free base according to general formula (I'b) can be systematically referred to as "1,1-(3-dimethylamino-3-phenylpentamethylene)-6-fluoro-1,3,4,9-tetrahydropyrano[3,4-b]indole (trans)" or as "(1r,4r)-6'-fluoro-N,N-dimethyl-4-phenyl-4',9'-dihydro-3'H-spiro[cyclohexane-1,1'-pyrano[3,4,b]indol]-4-amine", respectively.

The definition of the pharmacologically active agent according to general formula (I) as used herein includes 6'-fluoro-(N-methyl- or N,N-dimethyl-)-4-phenyl-4',9'-dihydro-3'H-spiro-[cyclohexane-1,1'-pyrano[3,4,b]indol]-4-amine, derivatives thereof and stereoisomers thereof in any possible form, thereby particularly including solvates and polymorphs, salts, in particular acid addition salts and corresponding solvates and polymorphs.

In a preferred embodiment, the pharmacologically active agent according to general formula (I) is present as the single diastereomer according to general formula (I').

In another preferred embodiment the pharmacologically active agent according to general formula (I) is present as mixture of diastereomers. Such a mixture may contain the diastereomers in any ratio. A diastereomeric mixture could, for example, contain the diastereomers in a ratio of 60±5:40±5, 70±5:30±5, 80±5:20±5 or 90±5:10±5. Preferably, the pharmaceutical dosage form according to the invention contains the diastereomer according to general formula (I') in a diastereomeric excess (de) of at least 50% de, more preferably at least 60% de, still more preferably at least 70% de, yet more preferably at least 80% de, even more preferably at least 90% de, most preferably at least 95% de, and in particular at least 98% de, with respect to the other diastereomer (i.e. trans vs. cis and anti vs. syn, respectively).

6'-fluoro-(N-methyl- or N,N-dimethyl-)-4-phenyl-4',9'-dihydro-3'H-spiro[cyclohexane-1,1'-pyrano[3,4,b]indol]-4-amine may be present in the pharmaceutical dosage form according to the invention in form of the free base or in form of an acid addition salt, whereby any suitable acid capable of forming such an addition salt may be used.

The conversion of 6'-fluoro-(N-methyl- or N,N-dimethyl-)-4-phenyl-4',9'-dihydro-3'H-spiro-[cyclohexane-1,1'-pyrano[3,4,b]indol]-4-amine into a corresponding addition salt, for example, via reaction with a suitable acid may be effected in a manner well known to those skilled in the art. Suitable acids include but are not limited to hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid and/or aspartic acid. Salt formation is preferably effected in a solvent, for example, diethyl ether, diisopropyl ether, alkyl acetates, acetone and/or 2-butanone. Moreover, trimethylchlorosilane in aqueous solution is also suitable for the preparation of hydrochlorides.

The pharmacologically active agent according to general formula (I) is preferably contained in the pharmaceutical dosage form in a therapeutically effective amount, i.e., in an amount that is therapeutically effective with regard to a daily administration of the dosage form in the treatment of pain, particularly in the treatment of neuropathic pain, especially chronic neuropathic pain, or in the treatment of nociceptive pain, particularly acute or chronic nociceptive pain. The amount that constitutes a therapeutically effective amount varies according to the compound, the condition being treated, the severity of said condition, the patient being treated, and whether the pharmaceutical dosage form is designed for an immediate or retarded release.

In another preferred embodiment, the pharmacologically active agent according to general formula (I) is contained in the dosage form in a quantity such that single administration of the dosage form does not lead to any analgesic effect, i.e. the pharmacologically active agent according to general formula (I) is contained in the dosage form in an amount that is subtherapeutic with regard to a single administration of the dosage form. Preferably, however, once daily administration of the dosage form leads to an analgesic effect, at the latest, on the fifth day, more preferably at the latest on the fourth day and still more preferably at the latest on the third day of once daily administration.

In an especially preferred embodiment, with respect to the treatment of neuropathic pain, preferably chronic neuropathic pain, once daily administration of the dosage form leads to a sub-therapeutic plasma concentration of the pharmacologically active agent on the first day of administration, but to therapeutic plasma concentrations of the pharmacologically active agent after once daily administration of the dosage form for at least 3, or at least 4, or at least 5 subsequent days.

In one preferred embodiment, the pharmacologically active agent according to general formula (I) is contained in the dosage form in a quantity such that the dosage form is not effective in the treatment of acute pain, i.e. the pharmacologically active agent is contained in a quantity that is sub-therapeutic with regard to acute pain treatment. Preferably, the quantity is so low that even after repeated administration for several consecutive days, e.g. ≥5 days, a significant effect in the treatment of acute pain is not achieved.

In another especially preferred embodiment, with respect to the treatment of nociceptive pain, preferably acute or chronic nociceptive pain, once daily administration of the dosage form leads to a sub-therapeutic plasma concentration of the pharmacologically active agent on the first day of administration, but to therapeutic plasma concentrations of the pharmacologically active agent after once daily administration of the dosage form for at least 3, or at least 4, or at least 5 subsequent days.

Preferably, the pharmacologically active agent according to general formula (I) is contained in the dosage form in a quantity such that initial dose titration is not required.

Preferably, the pharmacologically active agent according to general formula (I) is contained in the dosage form in a quantity such that adverse events that occur during administration of the dosage form are decreased compared to a dosage form comprising a pure μ-opioid receptor agonist, such as morphine in equianalgetic doses.

In a preferred embodiment, the content of the pharmacologically active agent according to the general formula (I) in the pharmaceutical dosage form according to the invention is at most 95 wt.-%, more preferably at most 50 wt.-%, yet more preferably at most 25 wt.-%, still more preferably at most 10 wt.-%, even more preferably at most 5 wt.-%, most preferably at most 1.0 wt.-%, and in particular at most 0.5 wt.-%.

In another preferred embodiment, the content of the pharmacologically active agent according to the general formula (I) in the pharmaceutical dosage form according to the invention is at least 0.001 wt.-%, more preferably at least 0.005 wt.-%, yet more preferably at least 0.01 wt.-%, still more preferably at least 0.05 wt.-%, even more preferably at least 0.1 wt.-%, most preferably at least 0.5 wt.-%, and in particular at least 1.0 wt.-%.

In another preferred embodiment, the content of the pharmacologically active agent according to the general formula (I) in the pharmaceutical dosage form according to the invention is within the range of 0.4±0.3 wt.-%, for example, 0.4±0.2 wt.-%, or even 0.4±0.1 wt.-%.

In another preferred embodiment, the content of the pharmacologically active agent according to the general formula (I) in the pharmaceutical dosage form according to the invention is within the range of 0.5±0.3 wt.-%, for example, 0.5±0.2 wt.-%, or even 0.5±0.1 wt.-%.

In still another preferred embodiment, the content of the pharmacologically active agent according to the general formula (I) in the pharmaceutical dosage form according to the invention is within the range of 0.3±0.3 wt.-%, for example, 0.320±0.315 wt.-%, more preferably 0.320±0.310 wt.-%, still more preferably 0.320±0.305 wt.-%, yet more preferably 0.320±0.300 wt.-%, even more preferably 0.320±0.295 wt.-%, most preferably 0.320±0.290 wt.-%, and in particular 0.320±0.285 wt.-%.

In yet another preferred embodiment, the content of the pharmacologically active agent according to the general formula (I) in the pharmaceutical dosage form according to the invention is within the range of 0.04±0.035 wt.-%, more preferably 0.04±0.03 wt.-%, still more preferably 0.04±0.025 wt.-%, yet more preferably 0.04±0.02 wt.-%, even more preferably 0.04±0.015 wt.-%, most preferably 0.04±0.01 wt.-%, and in particular 0.04±0.005 wt.-%.

In another preferred embodiment, the content of the pharmacologically active agent according to the general formula (I) in the pharmaceutical dosage form according to the invention is within the range of 0.6±0.35 wt.-%, more preferably 0.6±0.3 wt.-%, still more preferably 0.6±0.25 wt.-%, yet more preferably 0.6±0.2 wt.-%, even more preferably 0.6±0.15 wt.-%, most preferably 0.6±0.1 wt.-%, and in particular 0.6±0.05 wt.-%.

Unless explicitly stated otherwise, in the meaning of the present invention the indication "wt.-%" shall mean weight of the respective ingredient per total weight of the pharmaceutical dosage form. In case that the pharmaceutical dosage form is film coated or encapsulated by an encapsulating medium which does not contain any amount of the pharmacologically active agent according to the general formula (I) and surrounds a core that in turn contains the total amount of the pharmacologically active agent according to the general formula (I), the indication "wt.-%" shall mean weight of the respective ingredient per total weight of the composition forming said core.

When the pharmaceutical dosage form is encapsulated or film coated, the pharmacologically active agent according to general formula (I) is preferably homogeneously distributed in the core of the pharmaceutical dosage form. Preferably, the encapsulating medium or film coating does not contain any pharmacologically active agent according to general formula (I).

In one preferred embodiment of the invention the dose of the pharmacologically active agent according to general formula (I) preferably is in the range of 0.1 μg to 5000 μg, more preferably in the range of 0.1 μg to 1000 μg, and most preferably in the range of 1.0 μg to 100 μg or in the range of 30 μg to 600 μg.

In a preferred embodiment, the content of the pharmacologically active agent according to general formula (I) in the pharmaceutical dosage form is within the range of 25±20 μg, more preferably 25±15 μg, still more preferably 25±10 μg, and most preferably 25±5 μg.

In another preferred embodiment, the content of the pharmacologically active agent according to general formula (I) in the pharmaceutical dosage form is within the range of 40±35 μg, more preferably 40±30 μg, still more preferably 40±25 μg, yet more preferably 40±20 μg, even more preferably 40±15 μg, most preferably 40±10 μg, and in particular 40±5 μg.

In still another preferred embodiment, the content of the pharmacologically active agent according to general formula (I) in the pharmaceutical dosage form is within the range of 50±35 μg, more preferably 50±30 μg, still more preferably 50±25 μg, yet more preferably 50±20 μg, even more preferably 50±15 μg, most preferably 50±10 μg, and in particular 50±5 μg.

In yet another preferred embodiment, the content of the pharmacologically active agent according to general formula (I) in the pharmaceutical dosage form is within the range of 60±35 µg, more preferably 60±30 µg, still more preferably 60±25 µg, yet more preferably 60±20 µg, even more preferably 60±15 µg, most preferably 60±10 µg, and in particular 60±5 µg.

In another preferred embodiment, the content of the pharmacologically active agent according to general formula (I) in the pharmaceutical dosage form is within the range of 100±90 µg, more preferably 100±80 µg, still more preferably 100±60 µg, yet more preferably 100±40 µg, even more preferably 100±20 µg, most preferably 100±10 µg, and in particular 100±5 µg.

In still another preferred embodiment, the content of the pharmacologically active agent according to general formula (I) in the pharmaceutical dosage form is within the range of 200±175 µg, more preferably 200±150 µg, still more preferably 200±125 µg, yet more preferably 200±100 µg, even more preferably 200±75 µg, most preferably 200±50 µg, and in particular 200±25 µg.

In yet another preferred embodiment, the content of the pharmacologically active agent according to general formula (I) in the pharmaceutical dosage form is within the range of 400±350 µg, more preferably 400±300 µg, still more preferably 400±250 µg, yet more preferably 400±200 µg, even more preferably 400±150 µg, most preferably 400±100 µg, and in particular 400±50 µg.

In yet another preferred embodiment, the content of the pharmacologically active agent according to general formula (I) in the pharmaceutical dosage form is within the range of 600±350 µg, more preferably 600±300 µg, still more preferably 600±250 µg, yet more preferably 600±200 µg, even more preferably 600±150 µg, most preferably 600±100 µg, and in particular 600±50 µg.

In a preferred embodiment the pharmaceutical dosage form is for use in the treatment of acute pain, where the dose of the pharmacologically active agent according to general formula (I) preferably is in the range of 50 µg to 3000 µg, more preferably in the range of 100 µg to 1000 µg, even more preferably in the range of 300 µg to 500 µg, and most preferably in the range of 350 µg to 450 µg.

In another preferred embodiment, the pharmaceutical dosage form is for use in the treatment of acute pain, where the dose of the pharmacologically active agent according to general formula (I) preferably is in the range of 200 µg to 400 µg, and in particular in the range of 250 µg to 350 µg.

For the purpose of the specification, the wording "being for use in the treatment of pain" is equivalent with "being adapted for use in the treatment of pain".

In a preferred embodiment, the pharmaceutical dosage form is for use in the treatment of acute pain, where the dose of the pharmacologically active agent according to general formula (I) preferably is in the range of 200 µg to 400 µg, and in particular in the range of 250 µg to 350 µg.

In a preferred embodiment, the pharmaceutical dosage form is for use in the treatment of acute pain, where the dose of the pharmacologically active agent according to general formula (I) preferably is in the range of 250 µg to 450 µg, and in particular in the range of 300 µg to 400 µg.

In another preferred embodiment, the pharmaceutical dosage form is for use in the treatment of acute pain, where the dose of the pharmacologically active agent according to general formula (I) preferably is in the range of 300 µg to 500 µg, and in particular in the range of 350 µg to 450 µg.

In yet another preferred embodiment, the pharmaceutical dosage form is for use in the treatment of acute pain, where the dose of the pharmacologically active agent according to general formula (I) preferably is in the range of 350 µg to 550 µg, and in particular in the range of 400 µg to 500 µg.

In even another preferred embodiment, the pharmaceutical dosage form is for use in the treatment of acute pain, where the dose of the pharmacologically active agent according to general formula (I) preferably is in the range of 400 µg to 600 µg, and in particular in the range of 450 µg to 550 µg.

In another preferred embodiment the pharmaceutical dosage form is for use in the treatment of chronic pain, where the dose of the pharmacologically active agent according to general formula (I) preferably is in the range of 0.1 µg to 500 µg, more preferably in the range of 1 µg to 250 µg, even more preferably in the range of 5 µg to 100 µg, and most preferably in the range of 10 µg to 50 µg.

In a preferred embodiment, the pharmaceutical dosage form according to the invention is for oral administration, i.e. the pharmaceutical dosage form is adapted for oral administration. Suitable alternative pathways of administration of the pharmaceutical dosage form according to the invention include but are not limited to vaginal and rectal administration.

The pharmaceutical dosage form according to the invention is for administration twice daily, once daily or less frequently, i.e. the pharmaceutical dosage form is adapted for administration twice daily, once daily or less frequently.

In a preferred embodiment, the pharmaceutical dosage form according to the invention is for administration twice daily.

For the purpose of the specification, "administration twice daily" (bid) preferably means that the pharmaceutical dosage form is adapted for being administered according to a regimen comprising the administration of a first pharmaceutical dosage form according to the invention and the subsequent administration of a second pharmaceutical dosage form according to the invention, wherein both, the first and the second pharmaceutical dosage form are administered during a time interval of about 24 hours, but wherein the second pharmaceutical dosage form is administered not earlier than 6 hours, preferably not earlier than 8 hours, more preferably not earlier than 10 hours and in particular, about 12 hours after the first pharmaceutical dosage form has been administered.

In another preferred embodiment, the pharmaceutical dosage form according to the invention is for administration once daily.

For the purpose of the specification, "administration once daily" (sid) preferably means that the pharmaceutical dosage form is adapted for being administered according to a regimen comprising the administration of a first pharmaceutical dosage form according to the invention and the subsequent administration of a second pharmaceutical dosage form according to the invention, wherein both, the first and the second pharmaceutical dosage form are administered during a time interval of about 48 hours, but wherein the second pharmaceutical dosage form is administered not earlier than 18 hours, preferably not earlier than 20 hours, more preferably not earlier than 22 hours and in particular, about 24 hours after the first pharmaceutical dosage form has been administered.

In another preferred embodiment, the pharmaceutical dosage form according to the invention is for administration once daily or less frequently.

In another preferred embodiment, the pharmaceutical dosage form according to the invention is for administration less frequently than once daily, preferably thrice during four days (¾), twice during three days (⅔), thrice during five days (⅗), once during two days (½), thrice in a week (3/7), twice during five days (²⁄₅), once during three days (⅓), twice in a week (²⁄₇), once during four days (¼), once during five days (⅕), once during six days (⅙), or once in a week (⅐). According to this embodiment, administration once during two days (½) is particularly preferred.

A skilled person is fully aware that administration regimens "twice daily, once daily, or less frequently" may be realized by administering a single pharmaceutical dosage form containing the full amount of the pharmacologically active agent according to general formula (I) to be administered at a particular point in time or, alternatively, administering a multitude of dose units, i.e. two, three or more dose units, the sum of which multitude of dose units containing the full amount of the pharmacologically active agent according to general formula (I) to be administered at said particular point in time, where the individual dose units are for simultaneous administration or administration within a short period of time, e.g. within 5, 10 or 15 minutes.

In another preferred embodiment of the invention, the dosage form according to the invention is adapted for administration once daily and contains the pharmacologically active agent according to general formula (I) in a dose of from 10 µg to 190 µg, i.e. the dosage form according to the invention contains the pharmacologically active agent according to general formula (I) in a daily dose of from 10 µg to 190 µg.

In a preferred embodiment, the dose of the pharmacologically active agent according to general formula (I) preferably is in the range of from 10 µg to 180 µg, preferably in the range of from 12.5 µg to 150 µg, more preferably in the range of from 15 µg to 120 µg, still more preferably in the range of from 17.5 µg to 100 µg, yet more preferably in the range of from 20 µg to 90 µg, most preferably in the range of from 25 µg to 80 µg, and in particular in the range of from 30 µg to 75 µg.

In a preferred embodiment, the dose of the pharmacologically active agent according to general formula (I) is in the range of from 10 µg to 50 µg.

In a preferred embodiment, the dose of the pharmacologically active agent according to general formula (I) is in the range of from 1.0 µg to 100 µg.

In a preferred embodiment, the content of the pharmacologically active agent according to general formula (I) in the pharmaceutical dosage form is within the range of 30±20 µg, more preferably 30±15 µg, most preferably 30±10 µg, and in particular 30±5 µg. In another preferred embodiment, the content of the pharmacologically active agent according to general formula (I) in the pharmaceutical dosage form is within the range of 35±25 µg, more preferably 35±20 µg, still more preferably 35±15 µg, most preferably 35±10 µg, and in particular 35±5 µg. In a preferred embodiment, the content of the pharmacologically active agent according to general formula (I) in the pharmaceutical dosage form is within the range of 40±30 µg, more preferably 40±25 µg, still more preferably 40±20 µg, yet more preferably 40±15 µg, most preferably 40±10 µg, and in particular 40±5 µg. In another preferred embodiment, the content of the pharmacologically active agent according to general formula (I) in the pharmaceutical dosage form is within the range of 45±35 µg, more preferably 45±30 µg, still more preferably 45±25 µg, yet more preferably 45±20 µg, even more preferably 45±15 µg, most preferably 45±10 µg, and in particular 45±5 µg. In still another preferred embodiment, the content of the pharmacologically active agent according to general formula (I) in the pharmaceutical dosage form is within the range of 50±35 µg, more preferably 50±30 µg, still more preferably 50±25 µg, yet more preferably 50±20 µg, even more preferably 50±15 µg, most preferably 50±10 µg, and in particular 50±5 µg. In yet another preferred embodiment, the content of the pharmacologically active agent according to general formula (I) in the pharmaceutical dosage form is within the range of 55±35 µg, more preferably 55±30 µg, still more preferably 55±25 µg, yet more preferably 55±20 µg, even more preferably 55±15 µg, most preferably 55±10 µg, and in particular 55±5 µg. In a preferred embodiment, the content of the pharmacologically active agent according to general formula (I) in the pharmaceutical dosage form is within the range of 60±40 µg or 60±35 µg, more preferably 60±30 µg, still more preferably 60±25 µg, yet more preferably 60±20 µg, even more preferably 60±15 µg, most preferably 60±10 µg, and in particular 60±5 µg. In another preferred embodiment, the content of the pharmacologically active agent according to general formula (I) in the pharmaceutical dosage form is within the range of 65±40 µg or 65±35 µg, more preferably 65±30 µg, still more preferably 65±25 µg, yet more preferably 65±20 µg, even more preferably 65±15 µg, most preferably 65±10 µg, and in particular 65±5 µg. In still another preferred embodiment, the content of the pharmacologically active agent according to general formula (I) in the pharmaceutical dosage form is within the range of 70±40 µg or 70±35 µg, more preferably 70±30 µg, still more preferably 70±25 µg, yet more preferably 70±20 µg, even more preferably 70±15 µg, most preferably 70±10 µg, and in particular 70±5 µg. In yet another preferred embodiment, the content of the pharmacologically active agent according to general formula (I) in the pharmaceutical dosage form is within the range of 75±40 µg or 75±35 µg, more preferably 75±30 µg, still more preferably 75±25 µg, yet more preferably 75±20 µg, even more preferably 75±15 µg, most preferably 75±10 µg, and in particular 75±5 µg. In a preferred embodiment, the content of the pharmacologically active agent according to general formula (I) in the pharmaceutical dosage form is within the range of 80±45 µg or 80±40 µg, more preferably 80±35 µg or 80±30 µg, still more preferably 80±25 µg, yet more preferably 80±20 µg, even more preferably 80±15 µg, most preferably 80±10 µg, and in particular 80±5 µg. In another preferred embodiment, the content of the pharmacologically active agent according to general formula (I) in the pharmaceutical dosage form is within the range of 85±45 µg or 85±40 µg, more preferably 85±35 µg or 85±30 µg, still more preferably 85±25 µg, yet more preferably 85±20 µg, even more preferably 85±15 µg, most preferably 85±10 µg, and in particular 85±5 µg. In still another preferred embodiment, the content of the pharmacologically active agent according to general formula (I) in the pharmaceutical dosage form is within the range of 90±45 µg or 90±40 µg, more preferably 90±35 µg or 90±30 µg, still more preferably 90±25 µg, yet more preferably 90±20 µg, even more preferably 90±15 µg, most preferably 90±10 µg, and in particular 90±5 µg. In yet another preferred embodiment, the content of the pharmacologically active agent according to general formula (I) in the pharmaceutical dosage form is within the range of 95±35 µg, more preferably 95±30 µg, still more preferably 95±25 µg, yet more preferably 95±20 µg, even more preferably 95±15 µg, most preferably 95±10 µg, and in particular 95±5 µg. In a preferred embodiment, the content of the pharmacologically active agent according to general formula (I) in the pharmaceutical dosage form is within the range of 100±80 µg, more preferably 100±60 µg, still more preferably 100±40 µg, even more preferably 100±20 µg, most preferably 100±10 µg, and in particular 100±5 µg. In another preferred embodiment, the content of the pharmacologically active agent according to general formula (I) in the pharmaceutical dosage form is within the range of 110±35 µg, more preferably 110±30 µg, still more preferably 110±25 µg, yet preferably 110±20 µg, even more preferably 110±15 µg, most preferably 110±10 μg, and in particular 110±5 μg. In still another preferred embodiment, the content of the pharmacologically active agent according to general formula (I) in the pharmaceutical dosage form is within the range of 120±60 μg, more preferably 120±50 μg, still more preferably 120±40 μg, yet more preferably 120±30 μg, even more preferably 120±20 μg, most preferably 120±10 μg, and in particular 120±5 μg. In still another preferred embodiment, the content of the pharmacologically active agent according to general formula (I) in the pharmaceutical dosage form is within the range of 130±60 μg, more preferably 130±50 μg, still more preferably 130±40 μg, yet more preferably 130±30 μg, even more preferably 130±20 μg, most preferably 130±10 μg, and in particular 130±5 μg. In yet another preferred embodiment, the content of the pharmacologically active agent according to general formula (I) in the pharmaceutical dosage form is within the range of 140±50 μg, more preferably 140±50 μg, still more preferably 140±40 μg, yet more preferably 140±30 μg, even more preferably 140±20 μg, most preferably 140±10 μg, and in particular 140±5 μg. In still another preferred embodiment, the content of the pharmacologically active agent according to general formula (I) in the pharmaceutical dosage form is within the range of 150±60 μg, more preferably 150±50 μg, still more preferably 150±40 μg, yet more preferably 150±30 μg, even more preferably 150±20 μg, most preferably 150±10 μg, and in particular 150±5 μg. In a preferred embodiment, the content of the pharmacologically active agent according to general formula (I) in the pharmaceutical dosage form is within the range of 160±30 μg, more preferably 160±25 μg, still more preferably 160±20 μg, yet more preferably 160±15 μg, most preferably 160±10 μg, and in particular 160±5 μg. In another preferred embodiment, the content of the pharmacologically active agent according to general formula (I) in the pharmaceutical dosage form is within the range of 170±20 μg, more preferably 170±10 μg, and in particular 170±5 μg.

In a preferred embodiment, the pharmaceutical dosage form according to the invention is adapted for oral administration. Suitable alternative pathways of administration of the pharmaceutical dosage form according to the invention include but are not limited to vaginal and rectal administration.

In one preferred embodiment, the pharmaceutical dosage form according to the invention is intended for administration once daily.

For the purpose of the specification, "administration once daily" (sid, OD) preferably means that the pharmaceutical dosage form is adapted for being administered according to a regimen comprising the administration of a first pharmaceutical dosage form according to the invention and the subsequent administration of a second pharmaceutical dosage form according to the invention, wherein both, the first and the second pharmaceutical dosage form are administered during a time interval of about 48 hours, but wherein the second pharmaceutical dosage form is administered not earlier than 18 hours, preferably not earlier than 20 hours, more preferably not earlier than 22 hours and in particular, about 24 hours after the first pharmaceutical dosage form has been administered.

A skilled person is fully aware that administration regimens "once daily" may be realized by administering a single pharmaceutical dosage form containing the full amount of the pharmacologically active agent according to general formula (I) to be administered at a particular point in time or, alternatively, administering a multitude of dose units, i.e. two, three or more dose units, the sum of which multitude of dose units containing the full amount of the pharmacologically active agent according to general formula (I) to be administered at said particular point in time, where the individual dose units are adapted for simultaneous administration or administration within a short period of time, e.g. within 5, 10 or 15 minutes.

The dosage form according to the invention is for use in the treatment of neuropathic pain, preferably chronic neuropathic pain such as diabetic neuropathic pain. Preferably, the pain is moderate, severe, or moderate to severe.

For the purpose of the specification, neuropathic pain is pain that originates from nerve damage or nerve malfunction. Preferably, the neuropathic pain is selected from acute neuropathic pain and chronic neuropathic pain. Neuropathic pain may be caused by damage or disease affecting the central or peripheral portions of the nervous system involved in bodily feelings (the somatosensory system). Preferably, the dosage form according to the invention is for use in the treatment of chronic neuropathic pain or acute neuropathic pain, peripheral neuropathic pain or central neuropathic pain, mononeuropathic pain or polyneuropathic pain. When the neuropathic pain is chronic, it may be chronic peripheral neuropathic pain or chronic central neuropathic pain, in a preferred embodiment chronic peripheral mononeuropathic pain or chronic central mononeuropathic pain, in another preferred embodiment chronic peripheral polyneuropathic pain or chronic central polyneuropathic pain. When the neuropathic pain is acute, it may be acute peripheral neuropathic pain or acute central neuropathic pain, in a preferred embodiment acute peripheral mononeuropathic pain or acute central mononeuropathic pain, in another preferred embodiment acute peripheral polyneuropathic pain or acute central polyneuropathic pain. The invention also relates to a pharmacologically active agent according to general formula (I) or a physiologically acceptable salt thereof for use in the treatment of neuropathic pain as described above, preferably by means of administering once daily the pharmaceutical dosage form according to the invention.

Central neuropathic pain is found in spinal cord injury, multiple sclerosis, and some strokes. Fibromyalgia is potentially a central pain disorder and is responsive to medications that are effective for neuropathic pain. Aside from diabetic neuropathy and other metabolic conditions, the common causes of painful peripheral neuropathies are herpes zoster infection, HIV-related neuropathies, nutritional deficiencies, toxins, remote manifestations of malignancies, genetic, and immune mediated disorders or physical trauma to a nerve trunk. Neuropathic pain is common in cancer as a direct result of cancer on peripheral nerves (e.g., compression by a tumor), or as a side effect of chemotherapy, radiation injury or surgery.

In another preferred embodiment, the pain to be treated is selected from the group consisting of pain being or being associated with panic disorder [episodic paroxysmal anxiety] [F41.0]; dissociative [conversion] disorders [F44]; persistent somatoform pain disorder [F45.4]; pain disorders exclusively related to psychological factors [F45.41]; nonorganic dyspareunia [F52.6]; other enduring personality changes [F62.8]; sadomasochism [F65.5]; elaboration of physical symptoms for psychological reasons [F68.0]; migraine [G43]; other headache syndromes [G44]; trigeminal neuralgia [G50.0]; atypical facial pain [G50.1]; phantom limb syndrome with pain [G54.6]; phantom limb syndrome without pain [G54.7]; acute and chronic pain, not elsewhere classified [G89]; ocular pain [H57.1]; otalgia [H92.0]; angina pectoris, unspecified [I20.9]; other specified disorders of nose and nasal sinuses [J34.8]; other diseases of pharynx [J39.2]; temporomandibular joint disorders [K07.6]; other specified disorders of teeth and supporting structures [K08.8]; other specified diseases of jaws [K10.8]; other and unspecified lesions of oral mucosa [K13.7]; glossodynia [K14.6]; other specified diseases of anus and rectum [K62.8]; pain in joint [M25.5]; shoulder pain [M25.51]; sacrococcygeal disorders, not elsewhere classified [M53.3]; spine pain [M54.]; radiculopathy [M54.1]; cervicalgia [M54.2]; sciatica [M54.3]; low back pain [M54.5]; pain in thoracic spine [M54.6]; other dorsalgia [M54.8]; dorsalgia, unspecified [M54.9]; other shoulder lesions [M75.8]; other soft tissue disorders, not elsewhere classified [M79]; myalgia [M79.1]; neuralgia and neuritis, unspecified [M79.2]; pain in limb [M79.6]; other specified disorders of bone [M89.8]; unspecified renal colic [N23]; other specified disorders of penis [N48.8]; other specified disorders of male genital organs [N50.8]; mastodynia [N64.4]; pain and other conditions associated with female genital organs and menstrual cycle [N94]; mittelschmerz [N94.0]; other specified conditions associated with female genital organs and menstrual cycle [N94.8]; pain in throat and chest [R07]; pain in throat [R07.0]; chest pain on breathing [R07.1]; precordial pain [R07.2]; other chest pain [R07.3]; chest pain, unspecified [R07.4]; abdominal and pelvic pain [R10]; acute abdomen pain [R10.0]; pain localized to upper abdomen [R10.1]; pelvic and perineal pain [R10.2]; pain localized to other parts of lower abdomen [R10.3]; other and unspecified abdominal pain [R10.4]; flatulence and related conditions [R14]; abdominal rigidity [R19.3]; other and unspecified disturbances of skin sensation [R20.8]; pain associated with micturition [R30]; other and unspecified symptoms and signs involving the urinary system [R39.8]; headache [R51]; pain, not elsewhere classified [R52]; acute pain [R52.0]; chronic intractable pain [R52.1]; other chronic pain [R52.2]; pain, unspecified [R52.9]; other complications of cardiac and vascular prosthetic devices, implants and grafts [T82.8]; other complications of genitourinary prosthetic devices, implants and grafts [T83.8]; other complications of internal orthopaedic prosthetic devices, implants and grafts [T84.8]; other complications of internal prosthetic devices, implants and grafts, not elsewhere classified [T85.8]; wherein the information in brackets refers to the classification according to ICD-10. The invention also relates to a pharmacologically active agent according to general formula (I) or a physiologically acceptable salt thereof for use in the treatment of pain, preferably neuropathic pain as described above, preferably by means of administering once daily the pharmaceutical dosage form according to the invention.

In accordance with another preferred embodiment, the dosage form according to the invention is adapted for administration once daily and contains the pharmacologically active agent according to general formula (I) in a dose of from 150 µg to 800 µg, preferably more than 190 µg to 800 µg, i.e. the dosage form according to the invention contains the pharmacologically active agent according to general formula (I) in a daily dose of from 150 µg to 800 µg.

In a preferred embodiment, the dose of the pharmacologically active agent according to general formula (I) preferably is in the range of from 200 µg to 800 µg, preferably in the range of from 210 µg to 750 µg, more preferably in the range of from 220 µg to 700 µg, still more preferably in the range of from 230 µg to 650 µg, yet more preferably in the range of from 240 µg to 600 µg, and most preferably in the range of from 250 µg to 550 µg.

In a preferred embodiment, the dose of the pharmacologically active agent according to general formula (I) is in the range of from 200 µg to 600 µg. In a preferred embodiment, the dose of the pharmacologically active agent according to general formula (I) is in the range of from 300 µg to 500 µg.

In a preferred embodiment, the content of the pharmacologically active agent according to general formula (I) in the pharmaceutical dosage form is within the range of 200±50 µg, more preferably 200±40 µg, most preferably 200±30 µg, and in particular 200±20 µg. In another preferred embodiment, the content of the pharmacologically active agent according to general formula (I) in the pharmaceutical dosage form is within the range of 250±100 µg, more preferably 250±80 µg, most preferably 250±60 µg, and in particular 250±50 µg. In another preferred embodiment, the content of the pharmacologically active agent according to general formula (I) in the pharmaceutical dosage form is within the range of 300±150 µg, more preferably 300±125 µg, most preferably 300±100 µg, and in particular 300±50 µg. In another preferred embodiment, the content of the pharmacologically active agent according to general formula (I) in the pharmaceutical dosage form is within the range of 350±200 µg, more preferably 350±175 µg, still more preferably 350±150 µg, most preferably 350±100 µg, and in particular 350±50 µg. In a preferred embodiment, the content of the pharmacologically active agent according to general formula (I) in the pharmaceutical dosage form is within the range of 400±250 µg, more preferably 400±225 µg, still more preferably 400±200 µg, yet more preferably 400±150 µg, most preferably 400±100 µg, and in particular 400±50 µg. In another preferred embodiment, the content of the pharmacologically active agent according to general formula (I) in the pharmaceutical dosage form is within the range of 450±300 µg, more preferably 450±275 µg, still more preferably 450±250 µg, yet more preferably 450±200 µg, even more preferably 450±150 µg, most preferably 450±100 µg, and in particular 450±50 µg. In still another preferred embodiment, the content of the pharmacologically active agent according to general formula (I) in the pharmaceutical dosage form is within the range of 500±350 µg, more preferably 500±300 µg, still more preferably 500±250 µg, yet more preferably 500±200 µg, even more preferably 500±150 µg, most preferably 500±100 µg, and in particular 500±50 µg. In yet another preferred embodiment, the content of the pharmacologically active agent according to general formula (I) in the pharmaceutical dosage form is within the range of 550±350 µg, more preferably 550±300 µg, still more preferably 550±250 µg, yet more preferably 550±200 µg, even more preferably 550±150 µg, most preferably 550±100 µg, and in particular 550±50 µg. In a preferred embodiment, the content of the pharmacologically active agent according to general formula (I) in the pharmaceutical dosage form is within the range of 600±400 µg or 600±350 µg, more preferably 600±300 µg, still more preferably 600±250 µg, yet more preferably 600±200 µg, even more preferably 600±150 µg, most preferably 600±100 µg, and in particular 600±50 µg.

In a preferred embodiment, the pharmaceutical dosage form according to the invention is adapted for oral administration. Suitable alternative pathways of administration of the pharmaceutical dosage form according to the invention include but are not limited to vaginal and rectal administration.

The pharmaceutical dosage form according to the invention is intended for administration once daily.

For the purpose of the specification, "administration once daily" (sid, OD) preferably means that the pharmaceutical dosage form is adapted for being administered according to a regimen comprising the administration of a first pharmaceutical dosage form according to the invention and the subsequent administration of a second pharmaceutical dosage form according to the invention, wherein both, the first and the second pharmaceutical dosage form are administered during a time interval of about 48 hours, but wherein the second pharmaceutical dosage form is administered not earlier than 18 hours, preferably not earlier than 20 hours, more preferably not earlier than 22 hours and in particular, about 24 hours after the first pharmaceutical dosage form has been administered.

A skilled person is fully aware that administration regimens "once daily" may be realized by administering a single pharmaceutical dosage form containing the full amount of the pharmacologically active agent according to general formula (I) to be administered at a particular point in time or, alternatively, administering a multitude of dose units, i.e. two, three or more dose units, the sum of which multitude of dose units containing the full amount of the pharmacologically active agent according to general formula (I) to be administered at said particular point in time, where the individual dose units are adapted for simultaneous administration or administration within a short period of time, e.g. within 5, 10 or 15 minutes.

The dosage form according to the invention is for use in the treatment of nociceptive pain, preferably acute or chronic nociceptive pain. Preferably, the pain is moderate, severe, or moderate to severe.

Nociceptive pain refers to the discomfort that results when a stimulus causes tissue damage to the muscles, bones, skin or internal organs. For the purpose of the specification, nociceptive pain is caused by stimulation of peripheral nerve fibers that respond only to stimuli approaching or exceeding harmful intensity (nociceptors), and may be classified according to the mode of noxious stimulation; the most common categories being "thermal" (heat or cold), "mechanical" (crushing, tearing, etc.) and "chemical" (iodine in a cut, chili powder in the eyes). Nociceptive pain may also be divided into "visceral," "deep somatic" and "superficial somatic" pain.

Visceral pain describes a type of nociceptive pain originating in the body's internal organs or their surrounding tissues. This form of pain usually results from the infiltration of harmful cells, as well as the compression or extension of healthy cells. Patients suffering from visceral pain tend to feel generally achy, as this pain tends to not be localized to a specific area. Cancer is a common source of visceral pain.

Somatic pain is nociceptive pain that results from some injury to the body. It's generally localized to the affected area and abates when the body repairs the damage to that area. Deep somatic pain is initiated by stimulation of nociceptors in ligaments, tendons, bones, blood vessels, fasciae and muscles, and is dull, aching, poorly-localized pain. Examples include sprains and broken bones. Superficial pain is initiated by activation of nociceptors in the skin or superficial tissues, and is sharp, well-defined and clearly located.

According to the invention, nociceptive pain is preferably classified chronic if it has occurred for at least 3 months. Preferably, the chronic nociceptive pain is selected from chronic visceral pain, chronic deep somatic pain and chronic superficial somatic pain.

Common causes of nociceptive pain include broken or fractured bones, bruises, burns, cuts, inflammation (from infection or arthritis), and sprains. Thus, nociceptive pain includes post-operative pain, cancer pain, low back pain, osteoarthitic pain, and inflammatory pain.

In another preferred embodiment, the pain to be treated is selected from the group consisting of pain being or being associated with panic disorder [episodic paroxysmal anxiety] [F41.0]; dissociative [conversion] disorders [F44]; persistent somatoform pain disorder [F45.4]; pain disorders exclusively related to psychological factors [F45.41]; nonorganic dyspareunia [F52.6]; other enduring personality changes [F62.8]; sadomasochism [F65.5]; elaboration of physical symptoms for psychological reasons [F68.0]; migraine [G43]; other headache syndromes [G44]; trigeminal neuralgia [G50.0]; atypical facial pain [G50.1]; phantom limb syndrome with pain [G54.6]; phantom limb syndrome without pain [G54.7]; acute and chronic pain, not elsewhere classified [G89]; ocular pain [H57.1]; otalgia [H92.0]; angina pectoris, unspecified [120.9]; other specified disorders of nose and nasal sinuses [J34.8]; other diseases of pharynx [J39.2]; temporomandibular joint disorders [K07.6]; other specified disorders of teeth and supporting structures [K08.8]; other specified diseases of jaws [K10.8]; other and unspecified lesions of oral mucosa [K13.7]; glossodynia [K14.6]; other specified diseases of anus and rectum [K62.8]; pain in joint [M25.5]; shoulder pain [M25.51]; sacrococcygeal disorders, not elsewhere classified [M53.3]; spine pain [M54.]; radiculopathy [M54.1]; cervicalgia [M54.2]; sciatica [M54.3]; low back pain [M54.5]; pain in thoracic spine [M54.6]; other dorsalgia [M54.8]; dorsalgia, unspecified [M54.9]; other shoulder lesions [M75.8]; other soft tissue disorders, not elsewhere classified [M79]; myalgia [M79.1]; neuralgia and neuritis, unspecified [M79.2]; pain in limb [M79.6]; other specified disorders of bone [M89.8]; unspecified renal colic [N23]; other specified disorders of penis [N48.8]; other specified disorders of male genital organs [N50.8]; mastodynia [N64.4]; pain and other conditions associated with female genital organs and menstrual cycle [N94]; mittelschmerz [N94.0]; other specified conditions associated with female genital organs and menstrual cycle [N94.8]; pain in throat and chest [R07]; pain in throat [R07.0]; chest pain on breathing [R07.1]; precordial pain [R07.2]; other chest pain [R07.3]; chest pain, unspecified [R07.4]; abdominal and pelvic pain [R10]; acute abdomen pain [R10.0]; pain localized to upper abdomen [R10.1]; pelvic and perineal pain [R10.2]; pain localized to other parts of lower abdomen [R10.3]; other and unspecified abdominal pain [R10.4]; flatulence and related conditions [R14]; abdominal rigidity [R19.3]; other and unspecified disturbances of skin sensation [R20.8]; pain associated with micturition [R30]; other and unspecified symptoms and signs involving the urinary system [R39.8]; headache [R51]; pain, not elsewhere classified [R52]; acute pain [R52.0]; chronic intractable pain [R52.1]; other chronic pain [R52.2]; pain, unspecified [R52.9]; other complications of cardiac and vascular prosthetic devices, implants and grafts [T82.8]; other complications of genitourinary prosthetic devices, implants and grafts [T83.8]; other complications of internal orthopaedic prosthetic devices, implants and grafts [T84.8]; other complications of internal prosthetic devices, implants and grafts, not elsewhere classified [T85.8]; wherein the information in brackets refers to the classification according to ICD-10. The invention also relates to a pharmacologically active agent according to general formula (I) or a physiologically acceptable salt thereof for use in the treatment of pain, preferably neuropathic pain as described above, preferably by means of administering once daily the pharmaceutical dosage form according to the invention.

Preferably, the pharmaceutical dosage form according to the invention provides immediate release of the pharmacologically active agent according to general formula (I). Preferably, the pharmaceutical dosage form is specifically designed to provide immediate release of the pharmacologically active agent according to general formula (I) in vitro in accordance with Ph. Eur. When the pharmaceutical dosage form is coated, e.g., with a coating that is soluble in gastric juice, the release kinetic is preferably monitored after such coating has been dissolved.

For the purpose of specification, the term "immediate release" refers to any release profile that fulfills at least one, preferably both, of the following requirements. First, the pharmaceutical dosage form disintegrates in 10 minutes or less following exposure to a disintegrating medium. Methods to determine the disintegration time are known to a person skilled in the art. For instance, they can be determined according to the USP XXIV disintegration test procedure, using, for example, an Erweka ZT-71 disintegration tester. Second, the pharmaceutical dosage form releases at least 70 wt.-% of the drug within 15 minutes following exposure to a dissolution medium. Preferably, the in vitro release properties of the pharmaceutical dosage form according to the invention are determined according to the paddle method with sinker at 50, 75 or 100 rpm, preferably under in vitro conditions at 37±0.5° C. in 900 mL artificial gastric juice at pH 1.2, or under the same conditions in non-artificial gastric juice.

In a preferred embodiment, the pharmaceutical dosage form releases under in vitro conditions in 900 mL artificial gastric juice at pH 1.2 and 37±0.5° C. after 30 minutes according to the paddle method with sinker at 100 rpm at least 50 wt.-%, more preferably at least 60 wt.-%, still more preferably at least 70 wt.-%, yet more preferably at least 80 wt.-%, most preferably at least 90 wt.-%, and in particular at least 95 wt.-% of the pharmacologically active agent according to general formula (I), based on the total amount of the pharmacologically active agent according to general formula (I) originally contained in the pharmaceutical dosage form.

The pharmaceutical dosage form according to the invention exhibits excellent shelf-life and storage stability, i.e. neither the chemical composition, nor the physical characteristics, nor the dissolution profile of the pharmaceutical dosage form are altered significantly upon storage.

In a preferred embodiment, the pharmaceutical dosage form according to the invention provides sufficient stability to the pharmacologically active agent according to general formula (I) contained therein, so that after storage of the pharmaceutical dosage form at 40±2° C. at 75% RH±5% for a minimum time period of 6 weeks, preferably 3 months, the concentrations of undesirable degradants and impurities, respectively, preferably resulting from a degradation or decomposition of the pharmacologically active agent according to general formula (I) as such, is at most 1.0 wt.-%, more preferably at most 0.8 wt.-%, still more preferably at most 0.6 wt.-%, yet more preferably at most 0.4 wt.-%, even more preferably at most 0.2 wt.-%, most preferably at most 0.1 wt.-%, and in particular at most 0.05 wt.-%, relative to the original content of the pharmacologically active agent according to general formula (I) in the pharmaceutical dosage form, i.e. its content before subjecting the pharmaceutical dosage form to storage.

It has been found that the pharmacologically active agent according to general formula (I) may be decomposed by elimination of the group —NRCH₃ thereby yielding 6'-fluoro-4-phenyl-4',9'-dihydro-3'H-spiro[cyclohex-3-ene-1,1-pyrano[3,4-b]indole] which appears to be pharmacologically inactive. Preferably, after storage of the pharmaceutical dosage form at 40±2° C. and 75% RH±5%, or at 25±2° C. and 60% RH±5%, for a minimum time period of 6 weeks, preferably 3 months, the concentration of 6'-fluoro-4-phenyl-4', 9'-dihydro-3'H-spiro[cyclohex-3-ene-1,1-pyrano[3,4-b]indole] is at most 1.0 wt.-%, more preferably at most 0.8 wt.-%, still more preferably at most 0.6 wt.-%, yet more preferably at most 0.4 wt.-%, even more preferably at most 0.2 wt.-%, most preferably at most 0.1 wt.-%, and in particular at most 0.05 wt.-%, relative to the original content of the pharmacologically active agent according to general formula (I) in the pharmaceutical dosage form, i.e. its content before subjecting the pharmaceutical dosage form to storage.

A generally accepted accelerated test for the determination of a drug's stability according to ICH and FDA guidelines relates to the storage of a pharmaceutical formulation containing the drug (e.g., in its container and packaging). According to the ICH guidelines, a so-called accelerated storage testing should be conducted for pharmaceutical formulations at 40±2° C. at 75% RH±5% for a minimum time period of 6 months. Additionally, a so-called long-term storage testing should be conducted for pharmaceutical formulations at 25±2° C. at not less than 60% RH±5% for a minimum time period of 12 months. In case that all criteria have been met for the accelerated storage testing and long-term storage testing conditions during the 6-months period, the long-time storage testing may be shortened to 6 months and the corresponding data doubled to obtain estimated data for the 12-month period.

During the storage, samples of the pharmaceutical formulation are withdrawn at specified time intervals and analyzed in terms of their drug content, presence of impurities, their release profile and if applicable other parameters. According to the ICH guidelines, in all samples the purity of the drug should be ≥98%, the drug content should be 95-105% (FDA guideline: 90-110%). Furthermore, the pharmaceutical formulation should release >80% of the drug within 30 minutes.

In case of dosages forms such as tablets and capsules that contain less than 50 mg of a drug, a content uniformity test should additionally be conducted for 10 randomly chosen dosage forms. The pharmaceutical formulation complies if none individual content is outside the limits of 85% to 115% of the average content. In case that an individual content is outside these limits, another 30 dosage forms have to be analyzed. The preparation fails to comply with the test if more than 3 individual contents are outside the limits of 85 to 115% of the average content or if one or more individual contents are outside the limits of 75% to 125% of the average content.

In a preferred embodiment, after storage of the pharmaceutical dosage form for 6 months under long-term storage conditions (25° C. and 60% relative humidity) in a sealed glass container, the degradation of the pharmacologically active agent according to general formula (I) does not exceed 2.0%, more preferably 1.5%, still more preferably 1.0%, and most preferably 0.5%.

In another preferred embodiment, after storage of the pharmaceutical dosage form for 6 months under accelerated storage conditions (40° C. and 75% relative humidity) in a sealed glass container, the degradation of the pharmacologically active agent according to general formula (I) does not exceed 4%, more preferably 3%, still more preferably 2%, yet more preferably 1%, and most preferably 0.5%.

Preferably, after storage of the pharmaceutical dosage form for 6 months under long-term storage conditions (25° C. and 60% relative humidity), the pharmaceutical dosage form releases under in vitro conditions in 900 mL artificial gastric juice at pH 1.2 and 37±0.5° C. after 30 minutes according to the paddle method with sinker at 100 rpm at least 50 wt.-%, more preferably at least 60 wt.-%, still more preferably at least 70 wt.-%, and most preferably at least 80 wt.-% of the pharmacologically active agent according to general formula (I), based on the total amount of the pharmacologically active agent according to general formula (I) originally contained in the pharmaceutical dosage form.

Preferably, after storage of the pharmaceutical dosage form for 6 months under accelerated storage conditions (40° C. and 75% relative humidity), the pharmaceutical dosage form releases under in vitro conditions in 900 mL artificial gastric juice at pH 1.2 and 37±0.5° C. after 30 minutes according to the paddle method with sinker at 100 rpm at least 50 wt.-%, more preferably at least 60 wt.-%, still more preferably at least 70 wt.-%, and most preferably at least 80 wt.-% of the pharmacologically active agent according to general formula (I), based on the total amount of the pharmacologically active agent according to general formula (I) originally contained in the pharmaceutical dosage form.

The absorption properties of a pharmacologically active agent administered by a pharmaceutical dosage form can be described by the pharmacokinetic parameters $C_{max}$, $t_{max}$ and $AUC_{0-t}$. The determination of $C_{max}$ and $t_{max}$, as well as the calculation of an AUC are well known to a person skilled in the art and described, for example, in Bauer, Frömming, Führer, "Lehrbuch der Pharmazeutischen Technologie," 6th Edition (1999), and in Shargel, Wu-Pong, Yu, "Applied Biopharmaceuticals & Pharmacokinetics", $5^{th}$ Edition (2005). Unless expressly stated otherwise, all pharmacokinetic parameters are expressed as mean values over a population of subjects.

There is experimental evidence indicating that $AUC_{0-t}$ and $C_{max}$ of the pharmacologically active agent according to general formula (I) are proportional to the dose.

For the purpose of the specification, $C_{max}$ is the highest plasma concentration of the pharmacologically active agent reached after single administration of the pharmaceutical dosage form.

For the purpose of the specification, $t_{max}$ is the time needed in order to reach $C_{max}$. Preferably, unless expressly stated otherwise, $t_{max}$ and $C_{max}$ refer to the pharmacokinetic parameters that are observed after a single administration of the dosage form according to the invention to a subject that has not been treated with the pharmacologically active agent according to general formula (I) before (i.e. $C_{max}=C_{max,\ 1\ day}$ and $t_{max}=t_{max,\ 1\ day}$).

For the purpose of the specification, $C_{max,\ n\ days}$ is the highest plasma concentration of the pharmacologically active agent reached after once daily administration of the pharmaceutical dosage form for n consecutive days, wherein n can be e.g. 1, 2, 3, 4, 5, 6, etc.

For the purpose of the specification, $C_{max,\ \geq 5\ days}$ is the highest plasma concentration of the pharmacologically active agent reached after once daily administration of the pharmaceutical dosage form for at least 5 consecutive days. In a preferred embodiment, steady state conditions are reached after 5, 6, 7, 8, 9, 10, 11, 12, 13, 14, 15, 16 or more days, i.e. continuing administration of the dosage form according to the invention on additional consecutive days does not substantially increase $C_{max}$ any further.

For the purpose of the specification, $t_{max,\ n\ days}$ is the time needed to reach $C_{max,\ n\ days}$ (post-dose), wherein n can be e.g. 1, 2, 3, 4, 5, 6, etc.

For the purpose of the specification, $t_{max,\ \geq 5\ days}$ is the time needed to reach $C_{max,\ \geq 5\ days}$ (post-dose).

For the purpose of the specification, $AUC_{0-t}$ is the area under the curve after single administration to the time t of the last sample that contained an analytically quantifiable concentration of the pharmacologically active agent.

For the purpose of the specification, $AUC_{0-72h}$ is the area under the curve baseline after single administration to 72 hours thereafter.

In accordance with one advantageous embodiment of the invention the ratio $C_{max}$/dose is preferably within the range of from 0.01 to 3.00 m$^{-3}$, yet more preferably within the range of from 0.02 to 2.50 m$^{-3}$, more preferably within the range of from 0.04 to 2.00 m$^{-3}$, and most preferably within the range of from 0.06 to 1.69 m$^{-3}$. In a preferred embodiment, the ratio $C_{max}$/dose is within the range of 0.40±0.35 m$^{-3}$, more preferably 0.40±0.30 m$^{-3}$, still more preferably 0.40±0.25 m$^{-3}$, yet more preferably 0.40±0.20 m$^{-3}$, even more preferably 0.40±0.15 m$^{-3}$, most preferably 0.40±0.10 m$^{-3}$, and in particular 0.40±0.05 m$^{-3}$. In another preferred embodiment, the ratio $C_{max}$/dose is within the range of 0.80±0.70 m$^{-3}$, more preferably 0.80±0.60 m$^{-3}$, still more preferably 0.80±0.50 m$^{-3}$, yet more preferably 0.80±0.40 m$^{-3}$, even more preferably 0.80±0.30 m$^{-3}$, most preferably 0.80±0.20 m$^{-3}$, and in particular 0.80±0.10 m$^{-3}$. In still another preferred embodiment, the ratio $C_{max}$/dose is within the range of 1.20±1.05 m$^{-3}$, more preferably 1.20±0.90 m$^{-3}$, still more preferably 1.20±0.75 m$^{-3}$, yet more preferably 1.20±0.60 m$^{-3}$, even more preferably 1.20±0.45 m$^{-3}$, most preferably 1.20±0.30 m$^{-3}$, and in particular 1.20±0.15 m$^{-3}$.

Preferably, $t_{max}$ is within the range of from 15 minutes to 24 h, still more preferably within the range of from 20 minutes to 20 h, yet more preferably within the range of from 0.5 to 16 h, most preferably within the range of from 1 to 12 h, and in particular within the range of from 2 to 10 h. In a preferred embodiment, $t_{max}$ is within the range of 4±3.5 h, more preferably 4±3 h, still more preferably 4±2.5 h, yet more preferably 4±2 h, even more preferably 4±1.5 h, most preferably 4±1 h, and in particular 4±0.5 h. In another preferred embodiment, $t_{max}$ is within the range of 8±7 h, more preferably 8±6 h, still more preferably 8±5 h, yet more preferably 8±4 h, even more preferably 8±3 h, most preferably 8±2 h, and in particular 8±1 h. In still another preferred embodiment, $t_{max}$ is within the range of 12±11 h, more preferably 12±9 h, still more preferably 12±7 h, yet more preferably 12±5 h, even more preferably 12±3 h, most preferably 12±2 h, and in particular 12±1 h.

Preferably, the ratio $AUC_{0-t}$/dose is within the range from 0.3 to 20 h/m$^3$, more preferably within the range of from 0.4 to 18 h/m$^3$, still more preferably within the range of from 0.5 to 16.5 h/m$^3$ and most preferably within the range of from 0.55 to 12.5 h/m$^3$. In a preferred embodiment, the ratio $AUC_{0-t}$/dose is within the range of 3±2.5 h/m$^3$, more preferably 3±2 h/m$^3$, still more preferably 3±1.5 h/m$^3$, yet more preferably 3±1 h/m$^3$, even more preferably 3±0.75 h/m$^3$, most preferably 3±0.5 h/m$^3$, and in particular 3±0.25 h/m$^3$. In another preferred embodiment, the ratio $AUC_{0-t}$/dose is within the range of 6±5 h/m$^3$, more preferably 6±4 h/m$^3$, still more preferably 6±3 h/m$^3$, yet more preferably 6±2 h/m$^3$, even more preferably 6±1.5 h/m$^3$, most preferably 6±1 h/m$^3$, and in particular 6±0.5 h/m$^3$. In still another preferred embodiment, the ratio $AUC_{0-t}$/dose is within the range of 9±8 h/m$^3$, more preferably 9±7 h/m$^3$, still more preferably 9±5 h/m$^3$, yet more preferably 9±4 h/m$^3$, even more preferably 9±3 h/m$^3$, most preferably 9±2 h/m$^3$, and in particular 9±1 h/m$^3$.

In accordance with another preferred embodiment, $C_{max}$ may advantageously be within the range of from 1 to 250 µg/m$^3$, more preferably within the range of from 5 to 200 µg/m$^3$, still more preferably within the range of from 10 to 150 µg/m$^3$, most preferably within the range of from 15 to 120 µg/m$^3$, and in particular within the range of from 20 to 100 µg/m$^3$.

In a preferred embodiment, $C_{max}$ is within the range of 20±17.5 µg/m$^3$, more preferably within the range of 20±15 µg/m$^3$, still more preferably within the range of 20±12.5 µg/m$^3$, yet more preferably within the range of 20±10 µg/m$^3$, and most preferably within the range of 20±5 µg/m$^3$. In another preferred embodiment, $C_{max}$ is within the range of 25±20 µg/m$^3$, more preferably within the range of 25±17.5 µg/m$^3$, still more preferably within the range of 25±15 µg/m$^3$, yet more preferably within the range of 25±12.5 µg/m$^3$, most preferably within the range of 25±10 µg/m$^3$, and in particular within the range of 25±5 µg/m$^3$. In still another preferred embodiment, $C_{max}$ is within the range of 30±20 µg/m$^3$, more preferably within the range of 30±17.5 µg/m³, still more preferably within the range of 30±15 µg/m³, yet more preferably within the range of 30±12.5 µg/m³, most preferably within the range of 30±10 µg/m³, and in particular within the range of 30±5 µg/m³. In yet another preferred embodiment, $C_{max}$ is within the range of 35±20 µg/m³, more preferably within the range of 35±17.5 µg/m³, still more preferably within the range of 35±15 µg/m³, yet more preferably within the range of 35±12.5 µg/m³, most preferably within the range of 35±10 µg/m³, and in particular within the range of 35±5 µg/m³. In a preferred embodiment, $C_{max}$ is within the range of 40±35 µg/m³, more preferably within the range of 40±30 µg/m³, still more preferably within the range of 40±25 µg/m³, yet more preferably within the range of 40±20 µg/m³, most preferably within the range of 40±15 µg/m³, and in particular within the range of 40±10 µg/m³. In another preferred embodiment, $C_{max}$ is within the range of 50±40 µg/m³, more preferably within the range of 50±30 µg/m³, still more preferably within the range of 50±25 µg/m³, yet more preferably within the range of 50±20 µg/m³, most preferably within the range of 50±15 µg/m³, and in particular within the range of 50±10 µg/m³. In still another preferred embodiment, $C_{max}$ is within the range of 60±40 µg/m³, more preferably within the range of 60±30 µg/m³, still more preferably within the range of 60±25 µg/m³, yet more preferably within the range of 60±20 µg/m³, most preferably within the range of 60±15 µg/m³, and in particular within the range of 60±10 µg/m³. In yet another preferred embodiment, $C_{max}$ is within the range of 70±45 µg/m³, more preferably within the range of 70±40 µg/m³, still more preferably within the range of 70±30 µg/m³, yet more preferably within the range of 70±25 µg/m³, even more preferably within the range of 70±20 µg/m³, most preferably within the range of 70±15 µg/m³, and in particular within the range of 70±10 µg/m³. In another preferred embodiment, $C_{max}$ is within the range of 80±50 µg/m³, more preferably within the range of 80±40 µg/m³, still more preferably within the range of 80±30 µg/m³, yet more preferably within the range of 80±25 µg/m³, even more preferably within the range of 80±20 µg/m³, most preferably within the range of 80±15 µg/m³, and in particular within the range of 80±10 µg/m³. In a preferred embodiment, $C_{max}$ is within the range of 90±50 µg/m³, more preferably within the range of 90±30 µg/m³, still more preferably within the range of 90±25 µg/m³, yet more preferably within the range of 90±20 µg/m³, most preferably within the range of 90±15 µg/m³, and in particular within the range of 90±10 µg/m³. In another preferred embodiment, $C_{max}$ is within the range of 100±50 µg/m³, more preferably within the range of 100±30 µg/m³, still more preferably within the range of 100±25 µg/m³, yet more preferably within the range of 100±20 µg/m³, most preferably within the range of 100±15 µg/m³, and in particular within the range of 100±10 µg/m³. In still another preferred embodiment, $C_{max}$ is within the range of 120±50 µg/m³, more preferably within the range of 120±30 µg/m³, still more preferably within the range of 120±25 µg/m³, yet more preferably within the range of 120±20 µg/m³, most preferably within the range of 120±15 µg/m³, and in particular within the range of 120±10 µg/m³.

Preferably, the ratio $C_{max}$/dose is within the range of from 0.01 to 3.00 m⁻³, yet more preferably within the range of from 0.02 to 2.50 m⁻³, more preferably within the range of from 0.04 to 2.00 m⁻³, and most preferably within the range of from 0.06 to 1.69 m⁻³.

In a preferred embodiment, the ratio $C_{max}$/dose is within the range of 0.30±0.25 m⁻³, more preferably 0.30±0.20 m⁻³, still more preferably 0.30±0.15 m⁻³, most preferably 0.30±0.10 m⁻³, and in particular 0.30±0.05 m⁻³. In another preferred embodiment, the ratio $C_{max}$/dose is within the range of 0.40±0.35 m⁻³, more preferably 0.40±0.30 m⁻³, still more preferably 0.40±0.25 m⁻³, yet more preferably 0.40±0.20 m⁻³, even more preferably 0.40±0.15 m⁻³, most preferably 0.40±0.10 m⁻³, and in particular 0.40±0.05 m⁻³. In still another preferred embodiment, the ratio $C_{max}$/dose is within the range of 0.50±0.35 m⁻³, more preferably 0.50±0.30 m⁻³, still more preferably 0.50±0.25 m⁻³, yet more preferably 0.50±0.20 m⁻³, even more preferably 0.50±0.15 m⁻³, most preferably 0.50±0.10 m⁻³, and in particular 0.50±0.05 m⁻³. In yet another preferred embodiment, the ratio $C_{max}$/dose is within the range of 0.60±0.40 m⁻³, more preferably 0.60±0.30 m⁻³, still more preferably 0.60±0.25 m⁻³, yet more preferably 0.60±0.20 m⁻³, most preferably 0.60±0.15 m⁻³, and in particular 0.60±0.10 m⁻³. In even another preferred embodiment, the ratio $C_{max}$/dose is within the range of 0.70±0.40 m⁻³, more preferably 0.70±0.35 m⁻³, still more preferably 0.70±0.30 m⁻³, yet more preferably 0.70±0.25 m⁻³, even more preferably 0.70±0.20 m⁻³, most preferably 0.70±0.15 m⁻³, and in particular 0.70±0.10 m⁻³. In a preferred embodiment, the ratio $C_{max}$/dose is within the range of 0.80±0.70 m⁻³, more preferably 0.80±0.60 m⁻³, still more preferably 0.80±0.50 m⁻³, yet more preferably 0.80±0.40 m⁻³, even more preferably 0.80±0.30 m⁻³, most preferably 0.80±0.20 m⁻³, and in particular 0.80±0.10 m⁻³. In another preferred embodiment, the ratio $C_{max}$/dose is within the range of 0.90±0.70 m⁻³, more preferably 0.90±0.60 m⁻³, still more preferably 0.90±0.50 m⁻³, yet more preferably 0.90±0.40 m⁻³, even more preferably 0.90±0.30 m⁻³, most preferably 0.90±0.20 m⁻³, and in particular 0.90±0.10 m⁻³. In still another preferred embodiment, the ratio $C_{max}$/dose is within the range of 1.00±0.70 m⁻³, more preferably 1.00±0.60 m⁻³, still more preferably 1.00±0.50 m⁻³, yet more preferably 1.00±0.40 m⁻³, even more preferably 1.00±0.30 m⁻³, most preferably 1.00±0.20 m⁻³, and in particular 1.00±0.10 m⁻³. In another preferred embodiment, the ratio $C_{max}$/dose is within the range of 1.10±0.70 m⁻³, more preferably 1.10±0.60 m⁻³, still more preferably 1.10±0.50 m⁻³, yet more preferably 1.10±0.40 m⁻³, even more preferably 1.10±0.30 m⁻³, most preferably 1.10±0.20 m⁻³, and in particular 1.10±0.10 m⁻³. In yet another preferred embodiment, the ratio $C_{max}$/dose is within the range of 1.20±1.05 m⁻³, more preferably 1.20±0.90 m⁻³, still more preferably 1.20±0.75 m⁻³, yet more preferably 1.20±0.60 m⁻³, even more preferably 1.20±0.45 m⁻³, most preferably 1.20±0.30 m⁻³, and in particular 1.20±0.15 m⁻³.

In a preferred embodiment, $C_{max, \geq 5\ days}$ is within the range of from 1 to 150 µg/m³, more preferably within the range of from 10 to 120 µg/m³, still more preferably within the range of from 15 to 100 µg/m³, yet more preferably within the range of from 20 to 80 µg/m³, most preferably within the range of from 20 to 70 µg/m³, and in particular within the range of from 25 to 60 µg/m³

In a preferred embodiment, $C_{max, \geq 5\ days}$ is within the range of 25±20 µg/m³, more preferably within the range of 25±15 µg/m³, still more preferably within the range of 25±12.5 µg/m³, yet more preferably within the range of 25±10 µg/m³, most preferably within the range of 25±7.5 µg/m³, and in particular within the range of 25±5 µg/m³. In another preferred embodiment, $C_{max, \geq 5\ days}$ is within the range of 30±20 µg/m³, more preferably within the range of 30±15 µg/m³, still more preferably within the range of 30±12.5 µg/m³, yet more preferably within the range of 30±10 µg/m³, most preferably within the range of 30±7.5 µg/m³, and in particular within the range of 30±5 µg/m³. In still another preferred embodiment, $C_{max, \geq 5\ days}$ is within the range of 35±20 µg/m³, more preferably within the range of 35±15 µg/m³, still more preferably within the range of 35±12.5 µg/m³, yet more preferably within the range of 35±10 μg/m³, most preferably within the range of 35±7.5 μg/m³, and in particular within the range of 35±5 μg/m³. In yet another preferred embodiment, $C_{max, \geq 5\ days}$ is within the range of 40±20 μg/m³, more preferably within the range of 40±15 μg/m³, still more preferably within the range of 40±12.5 μg/m³, yet more preferably within the range of 40±10 μg/m³, most preferably within the range of 40±7.5 μg/m³, and in particular within the range of 40±5 μg/m³. In a preferred embodiment, $C_{max, \geq 5\ days}$ is within the range of 45±30 μg/m³, more preferably within the range of 45±25 μg/m³, still more preferably within the range of 45±20 μg/m³, yet more preferably within the range of 45±15 μg/m³, most preferably within the range of 45±10 μg/m³, and in particular within the range of 45±5 μg/m³. In another preferred embodiment, $C_{max, \geq 5\ days}$ is within the range of 50±30 μg/m³, more preferably within the range of 50±25 μg/m³, still more preferably within the range of 50±20 μg/m³, yet more preferably within the range of 50±15 μg/m³, most preferably within the range of 50±10 μg/m³, and in particular within the range of 50±5 μg/m³. In still another preferred embodiment, $C_{max, \geq 5\ days}$ is within the range of 55±30 μg/m³, more preferably within the range of 55±25 μg/m³, still more preferably within the range of 55±20 μg/m³, yet more preferably within the range of 55±15 μg/m³, most preferably within the range of 55±10 μg/m³, and in particular within the range of 55±5 μg/m³. In yet another preferred embodiment, $C_{max, \geq 5\ days}$ is within the range of 60±30 μg/m³, more preferably within the range of 60±25 μg/m³, still more preferably within the range of 60±20 μg/m³, yet more preferably within the range of 60±15 μg/m³, most preferably within the range of 60±10 μg/m³, and in particular within the range of 60±5 μg/m³. In a preferred embodiment, $C_{max, \geq 5\ days}$ is within the range of 65±30 μg/m³, more preferably within the range of 65±25 μg/m³, still more preferably within the range of 65±20 μg/m³, yet more preferably within the range of 65±15 μg/m³, most preferably within the range of 65±10 μg/m³, and in particular within the range of 65±5 μg/m³. In another preferred embodiment, $C_{max, \geq 5\ days}$ is within the range of 70±30 μg/m³, more preferably within the range of 70±25 μg/m³, still more preferably within the range of 70±20 μg/m³, yet more preferably within the range of 70±15 μg/m³, most preferably within the range of 70±10 μg/m³, and in particular within the range of 70±5 μg/m³. In still another preferred embodiment, $C_{max, \geq 5\ days}$ is within the range of 75±30 μg/m³, more preferably within the range of 75±25 μg/m³, still more preferably within the range of 75±20 μg/m³, yet more preferably within the range of 75±15 μg/m³, most preferably within the range of 75±10 μg/m³, and in particular within the range of 75±5 μg/m³. In yet another preferred embodiment, $C_{max, \geq 5\ days}$ is within the range of 80±30 μg/m³, more preferably within the range of 80±25 μg/m³, still more preferably within the range of 80±20 μg/m³, yet more preferably within the range of 80±15 μg/m³, most preferably within the range of 80±10 μg/m³, and in particular within the range of 80±5 μg/m³. In a preferred embodiment, $C_{max, \geq 5\ days}$ is within the range of 85±50 μg/m³, more preferably within the range of 85±40 μg/m³, still more preferably within the range of 85±30 μg/m³, yet more preferably within the range of 85±20 μg/m³, most preferably within the range of 85±10 μg/m³, and in particular within the range of 85±5 μg/m³. In another preferred embodiment, $C_{max, \geq 5\ days}$ is within the range of 90±50 μg/m³, more preferably within the range of 90±40 μg/m³, still more preferably within the range of 90±30 μg/m³, yet more preferably within the range of 90±20 μg/m³, most preferably within the range of 90±10 μg/m³, and in particular within the range of 90±5 μg/m³. In still another preferred embodiment, $C_{max, \geq 5\ days}$ is within the range of 100±50 μg/m³, more preferably within the range of 100±40 μg/m³, still more preferably within the range of 100±30 μg/m³, yet more preferably within the range of 100±20 μg/m³, most preferably within the range of 100±10 μg/m³, and in particular within the range of 100±5 μg/m³. In yet another preferred embodiment, $C_{max, \geq 5\ days}$ is within the range of 120±30 μg/m³, more preferably within the range of 120±25 μg/m³, still more preferably within the range of 120±20 μg/m³, yet more preferably within the range of 120±15 μg/m³, most preferably within the range of 120±10 μg/m³, and in particular within the range of 120±5 μg/m³.

Preferably, the ratio $C_{max, \geq 5\ days}$/dose is within the range of from 0.25 to 1.50 m⁻³, more preferably within the range of from 0.40 to 1.10 m⁻³, still more preferably within the range of from 0.45 to 1.00 m⁻³, yet more preferably within the range of from 0.50 to 0.95 m⁻³, most preferably within the range of from 0.55 to 0.90 m⁻³, and in particular within the range of from 0.60 to 0.85 m⁻³.

Preferably, the ratio $C_{max,\ 5\ days}/C_{max,\ 1\ day}$ is ≥1.00, more preferably ≥1.00.

In a preferred embodiment, the ratio $C_{max,\ 5\ days}/C_{max,\ 1\ day}$ is ≥1.00, more preferably ≥1.10, still more preferably ≥1.20, yet more preferably ≥1.30, most preferably ≥1.40, and in particular ≥1.50. In another preferred embodiment, the ratio $C_{max,\ 5\ days}/C_{max,\ 1\ day}$ is ≥1.60, more preferably ≥1.70, still more preferably ≥1.80, yet more preferably ≥1.90, most preferably ≥2.00, and in particular ≥2.10.

In a preferred embodiment, the ratio $C_{max,\ 5\ days}/C_{max,\ 1\ day}$ is ≤3.10, more preferably ≤3.00, still more preferably ≤2.90, yet more preferably ≤2.80, most preferably ≤2.70, and in particular ≤2.60. In another preferred embodiment, the ratio $C_{max,\ 5\ days}/C_{max,\ 1\ day}$ is ≤2.50, more preferably ≤2.40, still more preferably ≤2.30, yet more preferably ≤2.20, most preferably ≤2.10, and in particular ≤2.00.

For the purpose of the specification, $C_{0-3h}$ is the highest plasma concentration of the pharmacologically active agent reached after a single administration of the pharmaceutical dosage form within the first 3 hours after administration. Accordingly, for the purpose of the specification, $C_{0-3h,\ 1\ day}$ is the highest plasma concentration of the pharmacologically active agent reached within the first 3 hours after once daily administration of the pharmaceutical dosage form on the very first day of an administration interval, whereas $C_{0-3h,\ 5\ day}$ is the highest plasma concentration of the pharmacologically active agent reached within the first 3 hours after once daily administration of the pharmaceutical dosage form on the fifths day of said administration interval comprising 5 consecutive days where the dosage form is administered once daily.

In a preferred embodiment, the pharmaceutical dosage form contains the pharmacologically active agent in a quantity so that $C_{0-3h,\ 5d} \leq C_{0-3h,\ 1d}$. In another preferred embodiment, the pharmaceutical dosage form contains the pharmacologically active agent in a quantity so that $C_{0-3h,\ 5d} \geq C_{0-3h,\ 1d}$. In a preferred embodiment, the quotient $(C_{0-3h,\ 5d})/(C_{0-3h,\ 1d})$ is at most 2.5 or 2.4 or 2.3, more preferably at most 2.2 or 2.1 or 2.0, still more preferably at most 1.9 or 1.8 or 1.7, yet more preferably at most 1.6 or 1.5 or 1.4, most preferably at most 1.3 or 1.2 or 1.1, and in particular at most 1.0 or 0.9 or 0.8. In another preferred embodiment, the quotient $(C_{0-3h,\ 5d})/(C_{0-3h,\ 1d})$ is at least 0.8 or 0.9 or 1.0, more preferably at least 1.1 or 1.2 or 1.3, still more preferably at least 1.4 or 1.5 or 1.6, yet more preferably at least 1.7 or 1.8 or 1.9, most preferably at least 2.0 or 2.1 or 2.2, and in particular at least 2.3 or 2.4 or 2.5.

In a preferred embodiment, the highest plasma concentration of the pharmacologically active agent reached on day 5 of a 5 day long period of once daily administration of the pharmaceutical dosage form is higher than the highest plasma concentrations reached on the first and/or second and/or third and/or fourth day of said period.

In a preferred embodiment, the daily mean plasma concentration of the pharmacologically active agent is steadily increased during the first 5 days of at least 5 day long period of once daily administration of the pharmaceutical dosage form.

Preferably, the plasma concentration of the pharmacologically active agent measured 10 days after single administration of the pharmaceutical dosage form is still at least 0.5 pg/mL, more preferably at least 1.0 pg/mL, still more preferably 1.25 pg/mL, yet more preferably at least 1.5 pg/mL, most preferably at least 1.75 pg/mL, and in particular at least 2.0 pg/mL.

Preferably, the plasma concentration of the pharmacologically active agent measured 10 drug-free days after once daily administration of the pharmaceutical dosage form for at least 5 consecutive days is still at least 0.5 pg/mL, more preferably at least 1.0 pg/mL, still more preferably 1.25 pg/mL, yet more preferably at least 1.5 pg/mL, most preferably at least 1.75 pg/mL, and in particular at least 2.0 pg/mL.

According to the invention, the pharmacokinetic parameter $t_{max}$ is within the range of from 0.5 to 16 h. Preferably, $t_{max}$ is within the range of from 1 to 12 h, and in particular within the range of from 2 to 10 h.

In a preferred embodiment, $t_{max}$ is within the range of 4±3.5 h, more preferably 4±3 h, still more preferably 4±2.5 h, yet more preferably 4±2 h, even more preferably 4±1.5 h, most preferably 4±1 h, and in particular 4±0.5 h. In another preferred embodiment, $t_{max}$ is within the range of 5±3.5 h, more preferably 5±3 h, still more preferably 5±2.5 h, yet more preferably 5±2 h, even more preferably 5±1.5 h, most preferably 5±1 h, and in particular 5±0.5 h. In still another preferred embodiment, $t_{max}$ is within the range of 6±4 h, more preferably 6±3 h, still more preferably 6±2.5 h, yet more preferably 6±2 h, even more preferably 6±1.5 h, most preferably 6±1 h, and in particular 6±0.5 h. In yet another preferred embodiment, $t_{max}$ is within the range of 8±7 h, more preferably 8±6 h, still more preferably 8±5 h, yet more preferably 8±4 h, even more preferably 8±3 h, most preferably 8±2 h, and in particular 8±1 h. In even another preferred embodiment, $t_{max}$ is within the range of 12±3 h, more preferably 12±2 h, and most preferably 12±1 h.

In a preferred embodiment, $t_{max, \geq 5\ days}$ is within the range of from 1 to 12 h, more preferably within the range of from 1.5 to 10 h, still more preferably within the range of from 2 to 9 h, yet more preferably within the range of from 2.5 to 8 h, most preferably within the range of from 3 to 7 h, and in particular within the range of from 4 to 6 h.

In a preferred embodiment, $t_{max, \geq 5\ days}$ is within the range of 4±3.5 h, more preferably 4±3 h, still more preferably 4±2.5 h, yet more preferably 4±2 h, even more preferably 4±1.5 h, most preferably 4±1 h, and in particular 4±0.5 h. In another preferred embodiment, $t_{max, \geq 5\ days}$ is within the range of 5±3.5 h, more preferably 5±3 h, still more preferably 5±2.5 h, yet more preferably 5±2 h, even more preferably 5±1.5 h, most preferably 5±1 h, and in particular 5±0.5 h. In still another preferred embodiment, $t_{max, \geq 5\ days}$ is within the range of 6±4 h, more preferably 6±3 h, still more preferably 6±2.5 h, yet more preferably 6±2 h, even more preferably 6±1.5 h, most preferably 6±1 h, and in particular 6±0.5 h.

Preferably, the ratio $AUC_{0-t}$/dose is within the range from 0.3 to 20 h/m³, more preferably within the range of from 0.4 to 18 h/m³, still more preferably within the range of from 0.5 to 16.5 h/m³ and most preferably within the range of from 0.55 to 12.5 h/m³. In a preferred embodiment, the ratio $AUC_{0-t}$/dose is within the range of 3±2.5 h/m³, more preferably 3±2 h/m³, still more preferably 3±1.5 h/m³, yet more preferably 3±1 h/m³, even more preferably 3±0.75 h/m³, most preferably 3±0.5 h/m³, and in particular 3±0.25 h/m³. In another preferred embodiment, the ratio $AUC_{0-t}$/dose is within the range of 6±5 h/m³, more preferably 6±4 h/m³, still more preferably 6±3 h/m³, yet more preferably 6±2 h/m³, even more preferably 6±1.5 h/m³, most preferably 6±1 h/m³, and in particular 6±0.5 h/m³. In still another preferred embodiment, the ratio $AUC_{0-t}$/dose is within the range of 7.5±7 h/m³, more preferably 7.5±6 h/m³, still more preferably 7.5±5 h/m³, yet more preferably 7.5±4 h/m³, even more preferably 7.5±3 h/m³, most preferably 7.5±2 h/m³, and in particular 7.5±1 h/m³. In yet another preferred embodiment, the ratio $AUC_{0-t}$/dose is within the range of 9±8 h/m³, more preferably 9±7 h/m³, still more preferably 9±5 h/m³, yet more preferably 9±4 h/m³, even more preferably 9±3 h/m³, most preferably 9±2 h/m³, and in particular 9±1 h/m³. In another preferred embodiment, the ratio $AUC_{0-72h}$/dose is within the range of 10±7 h/m³, more preferably 10±6 h/m³, still more preferably 10±5 h/m³, yet more preferably 10±4 h/m³, even more preferably 10±3 h/m³, most preferably 10±2 h/m³, and in particular 10±1 h/m³.

Preferably, the ratio $AUC_{0-72h}$/dose is within the range from 0.3 to 20 h/m³, more preferably within the range of from 0.4 to 18 h/m³, still more preferably within the range of from 0.5 to 16.5 h/m³ and most preferably within the range of from 0.55 to 12.5 h/m³. In a preferred embodiment, the ratio $AUC_{0-72h}$/dose is within the range of 3±2.5 h/m³, more preferably 3±2 h/m³, still more preferably 3±1.5 h/m³, yet more preferably 3±1 h/m³, even more preferably 3±0.75 h/m³, most preferably 3±0.5 h/m³, and in particular 3±0.25 h/m³. In another preferred embodiment, the ratio $AUC_{0-72h}$/dose is within the range of 6±5 h/m³, more preferably 6±4 h/m³, still more preferably 6±3 h/m³, yet more preferably 6±2 h/m³, even more preferably 6±1.5 h/m³, most preferably 6±1 h/m³, and in particular 6±0.5 h/m³. In still another preferred embodiment, the ratio $AUC_{0-72h}$/dose is within the range of 7.5±7 h/m³, more preferably 7.5±6 h/m³, still more preferably 7.5±5 h/m³, yet more preferably 7.5±4 h/m³, even more preferably 7.5±3 h/m³, most preferably 7.5±2 h/m³, and in particular 7.5±1 h/m³. In yet another preferred embodiment, the ratio $AUC_{0-72h}$/dose is within the range of 9±8 h/m³, more preferably 9±7 h/m³, still more preferably 9±5 h/m³, yet more preferably 9±4 h/m³, even more preferably 9±3 h/m³, most preferably 9±2 h/m³, and in particular 9±1 h/m³.

In a preferred embodiment, the pharmaceutical dosage form according to the invention is administered once daily during an administration interval comprising an initial phase, during which the plasma concentration time profile substantially changes from day to day, and a steady state phase, during which the plasma concentration time profile does not substantially change from day to day. In this regard, during the steady state phase the plasma concentration time profile may still change during a day, i.e. the plasma concentration measured e.g. 1 hour after administration may substantially differ from the plasma concentration measured e.g. 2, 3, 4, 6, 12 or 20 hours after the same administration on the same day. However, during the steady state phase, the plasma concentration measured X hours after administration on day N does not substantially differ from the plasma concentration measured X hours after the following administration on the following day N+1. Preferably, the initial phase lasts 1, 2, 3, 4 or 5 consecutive days until the steady state phase commences. In a preferred embodiment, during the steady state phase, the pharmaceutical dosage form provides and maintains upon administration once daily pharmacologically effective plasma concentrations of the pharmacologically active agent according to general formula (I) for at least 12 h, preferably at least 18 h, more preferably at least 20 h, yet more preferably at least 22 h, and in particular all 24 h of at least 1.0 pg/mL, at least 2.0 pg/mL, or at least 3.0 pg/mL, more preferably at least 4.0 pg/mL, at least 5.0 pg/mL, or at least 6.0 pg/mL, still more preferably at least 7.0 pg/mL, at least 8.0 pg/mL, or at least 9.0 pg/mL, yet more preferably at least 10 pg/mL, at least 12.5 pg/mL, or at least 15 pg/mL, even more preferably at least 17.5 pg/mL, at least 20 pg/mL, or at least 22.5 pg/mL, most preferably at least 25 pg/mL, at least 27.5 pg/mL, or at least 30 pg/mL, and in particular at least 35 pg/mL, at least 40 pg/mL, or at least 50 pg/mL.

In accordance with yet another advantageous embodiment of the invention the dosage form according to the invention is adapted for administration once daily and contains the pharmacologically active agent according to general formula (I) in a dose of from 150 µg to 800 µg, preferably more than 190 µg to 800 µg, i.e. the dosage form according to the invention contains the pharmacologically active agent according to general formula (I) in a daily dose of from 150 µg to 800 µg.

In a preferred embodiment, the dose of the pharmacologically active agent according to general formula (I) preferably is in the range of from 200 µg to 800 µg, preferably in the range of from 210 µg to 750 µg, more preferably in the range of from 220 µg to 700 µg, still more preferably in the range of from 230 µg to 650 µg, yet more preferably in the range of from 240 µg to 600 µg, and most preferably in the range of from 250 µg to 550 µg.

In a preferred embodiment, the dose of the pharmacologically active agent according to general formula (I) is in the range of from 200 µg to 600 µg. In a preferred embodiment, the dose of the pharmacologically active agent according to general formula (I) is in the range of from 300 µg to 500 µg.

In a preferred embodiment, the content of the pharmacologically active agent according to general formula (I) in the pharmaceutical dosage form is within the range of 200±50 µg, more preferably 200±40 µg, most preferably 200±30 µg, and in particular 200±20 µg. In another preferred embodiment, the content of the pharmacologically active agent according to general formula (I) in the pharmaceutical dosage form is within the range of 250±100 µg, more preferably 250±80 µg, most preferably 250±60 µg, and in particular 250±50 µg. In another preferred embodiment, the content of the pharmacologically active agent according to general formula (I) in the pharmaceutical dosage form is within the range of 300±150 µg, more preferably 300±125 µg, most preferably 300±100 µg, and in particular 300±50 µg. In another preferred embodiment, the content of the pharmacologically active agent according to general formula (I) in the pharmaceutical dosage form is within the range of 350±200 µg, more preferably 350±175 µg, still more preferably 350±150 µg, most preferably 350±100 µg, and in particular 350±50 µg. In a preferred embodiment, the content of the pharmacologically active agent according to general formula (I) in the pharmaceutical dosage form is within the range of 400±250 µg, more preferably 400±225 µg, still more preferably 400±200 µg, yet more preferably 400±150 µg, most preferably 400±100 µg, and in particular 400±50 µg. In another preferred embodiment, the content of the pharmacologically active agent according to general formula (I) in the pharmaceutical dosage form is within the range of 450±300 µg, more preferably 450±275 µg, still more preferably 450±250 µg, yet more preferably 450±200 µg, even more preferably 450±150 µg, most preferably 450±100 µg, and in particular 450±50 µg. In still another preferred embodiment, the content of the pharmacologically active agent according to general formula (I) in the pharmaceutical dosage form is within the range of 500±350 µg, more preferably 500±300 µg, still more preferably 500±250 µg, yet more preferably 500±200 µg, even more preferably 500±150 µg, most preferably 500±100 µg, and in particular 500±50 µg. In yet another preferred embodiment, the content of the pharmacologically active agent according to general formula (I) in the pharmaceutical dosage form is within the range of 550±350 µg, more preferably 550±300 µg, still more preferably 550±250 µg, yet more preferably 550±200 µg, even more preferably 550±150 µg, most preferably 550±100 µg, and in particular 550±50 µg. In a preferred embodiment, the content of the pharmacologically active agent according to general formula (I) in the pharmaceutical dosage form is within the range of 600±400 µg or 600±350 µg, more preferably 600±300 µg, still more preferably 600±250 µg, yet more preferably 600±200 µg, even more preferably 600±150 µg, most preferably 600±100 µg, and in particular 600±50 µg.

In a preferred embodiment, the pharmaceutical dosage form according to the invention is adapted for oral administration. Suitable alternative pathways of administration of the pharmaceutical dosage form according to the invention include but are not limited to vaginal and rectal administration.

The pharmaceutical dosage form according to the invention is intended for administration once daily.

For the purpose of the specification, "administration once daily" (sid, OD) preferably means that the pharmaceutical dosage form is adapted for being administered according to a regimen comprising the administration of a first pharmaceutical dosage form according to the invention and the subsequent administration of a second pharmaceutical dosage form according to the invention, wherein both, the first and the second pharmaceutical dosage form are administered during a time interval of about 48 hours, but wherein the second pharmaceutical dosage form is administered not earlier than 18 hours, preferably not earlier than 20 hours, more preferably not earlier than 22 hours and in particular, about 24 hours after the first pharmaceutical dosage form has been administered.

A skilled person is fully aware that administration regimens "once daily" may be realized by administering a single pharmaceutical dosage form containing the full amount of the pharmacologically active agent according to general formula (I) to be administered at a particular point in time or, alternatively, administering a multitude of dose units, i.e. two, three or more dose units, the sum of which multitude of dose units containing the full amount of the pharmacologically active agent according to general formula (I) to be administered at said particular point in time, where the individual dose units are adapted for simultaneous administration or administration within a short period of time, e.g. within 5, 10 or 15 minutes.

The dosage form according to the invention is for use in the treatment of nociceptive pain, preferably acute or chronic nociceptive pain. Preferably, the pain is moderate, severe, or moderate to severe.

Nociceptive pain refers to the discomfort that results when a stimulus causes tissue damage to the muscles, bones, skin or internal organs. For the purpose of the specification, nociceptive pain is caused by stimulation of peripheral nerve fibers that respond only to stimuli approaching or exceeding harmful intensity (nociceptors), and may be classified according to the mode of noxious stimulation; the most common categories being "thermal" (heat or cold), "mechanical" (crushing, tearing, etc.) and "chemical" (iodine in a cut, chili powder in the eyes). Nociceptive pain may also be divided into "visceral," "deep somatic" and "superficial somatic" pain.

Visceral pain describes a type of nociceptive pain originating in the body's internal organs or their surrounding tissues. This form of pain usually results from the infiltration of harmful cells, as well as the compression or extension of healthy cells. Patients suffering from visceral pain tend to feel generally achy, as this pain tends to not be localized to a specific area. Cancer is a common source of visceral pain.

Somatic pain is nociceptive pain that results from some injury to the body. It's generally localized to the affected area and abates when the body repairs the damage to that area. Deep somatic pain is initiated by stimulation of nociceptors in ligaments, tendons, bones, blood vessels, fasciae and muscles, and is dull, aching, poorly-localized pain. Examples include sprains and broken bones. Superficial pain is initiated by activation of nociceptors in the skin or superficial tissues, and is sharp, well-defined and clearly located.

According to the invention, nociceptive pain is preferably classified chronic if it has occurred for at least 3 months. Preferably, the chronic nociceptive pain is selected from chronic visceral pain, chronic deep somatic pain and chronic superficial somatic pain.

Preferred causes of nociceptive pain according to the invention include broken or fractured bones, bruises, burns, cuts, inflammation (from infection or arthritis), and sprains. Thus, nociceptive pain includes post-operative pain, cancer pain, low back pain, and inflammatory pain.

In another preferred embodiment, the pain to be treated is selected from the group consisting of pain being or being associated with panic disorder [episodic paroxysmal anxiety] [F41.0]; dissociative [conversion] disorders [F44]; persistent somatoform pain disorder [F45.4]; pain disorders exclusively related to psychological factors [F45.41]; nonorganic dyspareunia [F52.6]; other enduring personality changes [F62.8]; sadomasochism [F65.5]; elaboration of physical symptoms for psychological reasons [F68.0]; migraine [G43]; other headache syndromes [G44]; trigeminal neuralgia [G50.0]; atypical facial pain [G50.1]; phantom limb syndrome with pain [G54.6]; phantom limb syndrome without pain [G54.7]; acute and chronic pain, not elsewhere classified [G89]; ocular pain [H57.1]; otalgia [H92.0]; angina pectoris, unspecified [I20.9]; other specified disorders of nose and nasal sinuses [J34.8]; other diseases of pharynx [J39.2]; temporomandibular joint disorders [K07.6]; other specified disorders of teeth and supporting structures [K08.8]; other specified diseases of jaws [K10.8]; other and unspecified lesions of oral mucosa [K13.7]; glossodynia [K14.6]; other specified diseases of anus and rectum [K62.8]; pain in joint [M25.5]; shoulder pain [M25.51]; sacrococcygeal disorders, not elsewhere classified [M53.3]; spine pain [M54.]; radiculopathy [M54.1]; cervicalgia [M54.2]; sciatica [M54.3]; low back pain [M54.5]; pain in thoracic spine [M54.6]; other dorsalgia [M54.8]; dorsalgia, unspecified [M54.9]; other shoulder lesions [M75.8]; other soft tissue disorders, not elsewhere classified [M79]; myalgia [M79.1]; neuralgia and neuritis, unspecified [M79.2]; pain in limb [M79.6]; other specified disorders of bone [M89.8]; unspecified renal colic [N23]; other specified disorders of penis [N48.8]; other specified disorders of male genital organs [N50.8]; mastodynia [N64.4]; pain and other conditions associated with female genital organs and menstrual cycle [N94]; mittelschmerz [N94.0]; other specified conditions associated with female genital organs and menstrual cycle [N94.8]; pain in throat and chest [R07]; pain in throat [R07.0]; chest pain on breathing [R07.1]; precordial pain [R07.2]; other chest pain [R07.3]; chest pain, unspecified [R07.4]; abdominal and pelvic pain [R10]; acute abdomen pain [R10.0]; pain localized to upper abdomen [R10.1]; pelvic and perineal pain [R10.2]; pain localized to other parts of lower abdomen [R10.3]; other and unspecified abdominal pain [R10.4]; flatulence and related conditions [R14]; abdominal rigidity [R19.3]; other and unspecified disturbances of skin sensation [R20.8]; pain associated with micturition [R30]; other and unspecified symptoms and signs involving the urinary system [R39.8]; headache [R51]; pain, not elsewhere classified [R52]; acute pain [R52.0]; chronic intractable pain [R52.1]; other chronic pain [R52.2]; pain, unspecified [R52.9]; other complications of cardiac and vascular prosthetic devices, implants and grafts [T82.8]; other complications of genitourinary prosthetic devices, implants and grafts [T83.8]; other complications of internal orthopaedic prosthetic devices, implants and grafts [T84.8]; other complications of internal prosthetic devices, implants and grafts, not elsewhere classified [T85.8]; wherein the information in brackets refers to the classification according to ICD-10. The invention also relates to a pharmacologically active agent according to general formula (I) or a physiologically acceptable salt thereof for use in the treatment of pain, preferably neuropathic pain as described above, preferably by means of administering once daily the pharmaceutical dosage form according to the invention.

In accordance with yet another preferred embodiment of the invention, $C_{max}$ is preferably within the range of from 1 to 250 µg/m$^3$, more preferably within the range of from 10 to 220 µg/m$^3$, still more preferably within the range of from 40 to 200 µg/m$^3$, most preferably within the range of from 60 to 170 µg/m$^3$, and in particular within the range of from 80 to 150 µg/m$^3$.

In a preferred embodiment, $C_{max}$ is within the range of 90±80 µg/m$^3$, more preferably within the range of 90±70 µg/m$^3$, still more preferably within the range of 90±60 µg/m$^3$, yet more preferably within the range of 90±50 µg/m$^3$, even more preferably within the range of 90±40 µg/m$^3$, most preferably within the range of 90±30 µg/m$^3$, and in particular within the range of 90±20 µg/m$^3$. In another preferred embodiment, $C_{max}$ is within the range of 100±80 µg/m$^3$, more preferably within the range of 100±70 µg/m$^3$, still more preferably within the range of 100±60 µg/m$^3$, yet more preferably within the range of 100±50 µg/m$^3$, even more preferably within the range of 100±40 µg/m$^3$, most preferably within the range of 100±30 µg/m$^3$, and in particular within the range of 100±20 µg/m$^3$. In still another preferred embodiment, $C_{max}$ is within the range of 110±80 µg/m$^3$, more preferably within the range of 110±70 µg/m$^3$, still more preferably within the range of 110±60 µg/m$^3$, yet more preferably within the range of 110±50 µg/m$^3$, even more preferably within the range of 110±40 µg/m$^3$, most preferably within the range of 110±30 µg/m$^3$, and in particular within the range of 110±20 µg/m$^3$. In yet another preferred embodiment, $C_{max}$ is within the range of 120±80 µg/m$^3$, more preferably within the range of 120±70 µg/m$^3$, still more preferably within the range of 120±60 µg/m$^3$, yet more preferably within the range of 120±50 µg/m$^3$, even more preferably within the range of 120±40 µg/m$^3$, most preferably within the range of 120±30 µg/m$^3$, and in particular within the range of 120±20 µg/m$^3$. In a preferred embodiment, $C_{max}$ is within the range of 130±80 µg/m$^3$, more preferably within the range of 130±70 µg/m$^3$, still more preferably within the range of 130±60 µg/m$^3$, yet more preferably within the range of 130±50 µg/m$^3$, even more preferably within the range of 130±40 µg/m$^3$, most preferably within the range of 130±30 µg/m$^3$, and in particular within the range of 130±20 µg/m$^3$. In another preferred embodiment, $C_{max}$ is within the range of 140±80 µg/m$^3$, more preferably within the range of 140±70 µg/m$^3$, still more preferably within the range of 140±60 μg/m³, yet more preferably within the range of 140±50 μg/m³, even more preferably within the range of 140±40 μg/m³, most preferably within the range of 140±30 μg/m³, and in particular within the range of 140±20 μg/m³. In still another preferred embodiment, $C_{max}$ is within the range of 150±80 μg/m³, more preferably within the range of 150±70 μg/m³, still more preferably within the range of 150±60 μg/m³, yet more preferably within the range of 150±50 μg/m³, even more preferably within the range of 150±40 μg/m³, most preferably within the range of 150±30 μg/m³, and in particular within the range of 150±20 μg/m³. In yet another preferred embodiment, $C_{max}$ is within the range of 160±80 μg/m³, more preferably within the range of 160±70 μg/m³, still more preferably within the range of 160±60 μg/m³, yet more preferably within the range of 160±50 μg/m³, even more preferably within the range of 160±40 μg/m³, most preferably within the range of 160±30 μg/m³, and in particular within the range of 160±20 μg/m³. In a preferred embodiment, $C_{max}$ is within the range of 170±80 μg/m³, more preferably within the range of 170±70 μg/m³, still more preferably within the range of 170±60 μg/m³, yet more preferably within the range of 170±50 μg/m³, even more preferably within the range of 170±40 μg/m³, most preferably within the range of 170±30 μg/m³, and in particular within the range of 170±20 μg/m³.

Preferably, the ratio $C_{max}$/dose is within the range of from 0.01 to 3.00 m⁻³, yet more preferably within the range of from 0.02 to 2.50 m⁻³, more preferably within the range of from 0.04 to 2.00 m⁻³, and most preferably within the range of from 0.06 to 1.69 m⁻³.

In a preferred embodiment, the ratio $C_{max}$/dose is within the range of 0.25±0.20 m⁻³, more preferably 0.25±0.15 m⁻³, still more preferably 0.25±0.10 m⁻³, and most preferably 0.25±0.15 m⁻³. In a preferred embodiment, the ratio $C_{max}$/dose is within the range of 0.30±0.25 m⁻³, more preferably 0.30±0.20 m⁻³, still more preferably 0.30±0.15 m⁻³, most preferably 0.30±0.10 m⁻³, and in particular 0.30±0.05 m⁻³. In another preferred embodiment, the ratio $C_{max}$/dose is within the range of 0.40±0.35 m⁻³, more preferably 0.40±0.30 m⁻³, still more preferably 0.40±0.25 m⁻³, yet more preferably 0.40±0.20 m⁻³, even more preferably 0.40±0.15 m⁻³, most preferably 0.40±0.10 m⁻³, and in particular 0.40±0.05 m⁻³. In still another preferred embodiment, the ratio $C_{max}$/dose is within the range of 0.50±0.35 m⁻³, more preferably 0.50±0.30 m⁻³, still more preferably 0.50±0.25 m⁻³, yet more preferably 0.50±0.20 m⁻³, even more preferably 0.50±0.15 m⁻³, most preferably 0.50±0.10 m⁻³, and in particular 0.50±0.05 m⁻³. In yet another preferred embodiment, the ratio $C_{max}$/dose is within the range of 0.60±0.40 m⁻³, more preferably 0.60±0.30 m⁻³, still more preferably 0.60±0.25 m⁻³, yet more preferably 0.60±0.20 m⁻³, most preferably 0.60±0.15 m⁻³, and in particular 0.60±0.10 m⁻³. In even another preferred embodiment, the ratio $C_{max}$/dose is within the range of 0.70±0.40 m⁻³, more preferably 0.70±0.35 m⁻³, still more preferably 0.70±0.30 m⁻³, yet more preferably 0.70±0.25 m⁻³, even more preferably 0.70±0.20 m⁻³, most preferably 0.70±0.15 m⁻³, and in particular 0.70±0.10 m⁻³. In a preferred embodiment, the ratio $C_{max}$/dose is within the range of 0.80±0.70 m⁻³, more preferably 0.80±0.60 m⁻³, still more preferably 0.80±0.50 m⁻³, yet more preferably 0.80±0.40 m⁻³, even more preferably 0.80±0.30 m⁻³, most preferably 0.80±0.20 m⁻³, and in particular 0.80±0.10 m⁻³. In another preferred embodiment, the ratio $C_{max}$/dose is within the range of 0.90±0.70 m⁻³, more preferably 0.90±0.60 m⁻³, still more preferably 0.90±0.50 m⁻³, yet more preferably 0.90±0.40 m⁻³, even more preferably 0.90±0.30 m⁻³, most preferably 0.90±0.20 m⁻³, and in particular 0.90±0.10 m⁻³. In still another preferred embodiment, the ratio $C_{max}$/dose is within the range of 1.00±0.70 m⁻³, more preferably 1.00±0.60 m⁻³, still more preferably 1.00±0.50 m⁻³, yet more preferably 1.00±0.40 m⁻³, even more preferably 1.00±0.30 m⁻³, most preferably 1.00±0.20 m⁻³, and in particular 1.00±0.10 m⁻³. In another preferred embodiment, the ratio $C_{max}$/dose is within the range of 1.10±0.70 m⁻³, more preferably 1.10±0.60 m⁻³, still more preferably 1.10±0.50 m⁻³, yet more preferably 1.10±0.40 m⁻³, even more preferably 1.10±0.30 m⁻³, most preferably 1.10±0.20 m⁻³, and in particular 1.10±0.10 m⁻³. In yet another preferred embodiment, the ratio $C_{max}$/dose is within the range of 1.20±1.05 m⁻³, more preferably 1.20±0.90 m⁻³, still more preferably 1.20±0.75 m⁻³, yet more preferably 1.20±0.60 m⁻³, even more preferably 1.20±0.45 m⁻³, most preferably 1.20±0.30 m⁻³, and in particular 1.20±0.15 m⁻³.

In a preferred embodiment, the highest plasma concentration of the pharmacologically active agent reached on day 5 of a 5 day long period of once daily administration of the pharmaceutical dosage form is higher than the highest plasma concentrations reached on the first and/or second and/or third and/or fourth day of said period.

In a preferred embodiment, the daily mean plasma concentration of the pharmacologically active agent is steadily increased during the first 5 days of at least 5 day long period of once daily administration of the pharmaceutical dosage form.

Preferably, the plasma concentration of the pharmacologically active agent measured 10 days after single administration of the pharmaceutical dosage form is still at least 0.5 pg/mL, more preferably at least 1.0 pg/mL, still more preferably 1.25 pg/mL, yet more preferably at least 1.5 pg/mL, most preferably at least 1.75 pg/mL, and in particular at least 2.0 pg/mL.

Preferably, the plasma concentration of the pharmacologically active agent measured 10 drug-free days after once daily administration of the pharmaceutical dosage form for at least 5 consecutive days is still at least 0.5 pg/mL, more preferably at least 1.0 pg/mL, still more preferably 1.25 pg/mL, yet more preferably at least 1.5 pg/mL, most preferably at least 1.75 pg/mL, and in particular at least 2.0 pg/mL.

According to the invention, the pharmacokinetic parameter $t_{max}$ is within the range of from 0.5 to 16 h. Preferably, $t_{max}$ is within the range of from 1 to 12 h, and in particular within the range of from 2 to 10 h.

In a preferred embodiment, $t_{max}$ is within the range of 4±3.5 h, more preferably 4±3 h, still more preferably 4±2.5 h, yet more preferably 4±2 h, even more preferably 4±1.5 h, most preferably 4±1 h, and in particular 4±0.5 h. In another preferred embodiment, $t_{max}$ is within the range of 5±3.5 h, more preferably 5±3 h, still more preferably 5±2.5 h, yet more preferably 5±2 h, even more preferably 5±1.5 h, most preferably 5±1 h, and in particular 5±0.5 h. In still another preferred embodiment, $t_{max}$ is within the range of 6±4 h, more preferably 6±3 h, still more preferably 6±2.5 h, yet more preferably 6±2 h, even more preferably 6±1.5 h, most preferably 6±1 h, and in particular 6±0.5 h. In yet another preferred embodiment, $t_{max}$ is within the range of 7±6 h, more preferably 7±5 h, still more preferably 7±4 h, yet more preferably 7±3 h, even more preferably 7±2 h, most preferably 7±1 h, and in particular 7±0.5 h. In yet another preferred embodiment, $t_{max}$ is within the range of 8±7 h, more preferably 8±6 h, still more preferably 8±5 h, yet more preferably 8±4 h, even more preferably 8±3 h, most preferably 8±2 h, and in particular 8±1 h. In even another preferred embodiment, $t_{max}$ is within the range of 12±3 h, more preferably 12±2 h, and most preferably 12±1 h.

Preferably, the ratio $AUC_{0-t}$/dose is within the range from 0.3 to 20 h/m$^3$, more preferably within the range of from 0.4 to 18 h/m$^3$, still more preferably within the range of from 0.5 to 16.5 h/m$^3$ and most preferably within the range of from 0.55 to 12.5 h/m$^3$. In a preferred embodiment, the ratio $AUC_{0-t}$/dose is within the range of 3±2.5 h/m$^3$, more preferably 3±2 h/m$^3$, still more preferably 3±1.5 h/m$^3$, yet more preferably 3±1 h/m$^3$, even more preferably 3±0.75 h/m$^3$, most preferably 3±0.5 h/m$^3$, and in particular 3±0.25 h/m$^3$. In another preferred embodiment, the ratio $AUC_{0-t}$/dose is within the range of 6±5 h/m$^3$, more preferably 6±4 h/m$^3$, still more preferably 6±3 h/m$^3$, yet more preferably 6±2 h/m$^3$, even more preferably 6±1.5 h/m$^3$, most preferably 6±1 h/m$^3$, and in particular 6±0.5 h/m$^3$. In still another preferred embodiment, the ratio $AUC_{0-t}$/dose is within the range of 7.5±7 h/m$^3$, more preferably 7.5±6 h/m$^3$, still more preferably 7.5±5 h/m$^3$, yet more preferably 7.5±4 h/m$^3$, even more preferably 7.5±3 h/m$^3$, most preferably 7.5±2 h/m$^3$, and in particular 7.5±1 h/m$^3$. In yet another preferred embodiment, the ratio $AUC_{0-t}$/dose is within the range of 9±8 h/m$^3$, more preferably 9±7 h/m$^3$, still more preferably 9±5 h/m$^3$, yet more preferably 9±4 h/m$^3$, even more preferably 9±3 h/m$^3$, most preferably 9±2 h/m$^3$, and in particular 9±1 h/m$^3$. In another preferred embodiment, the ratio $AUC_{0-72h}$/dose is within the range of 10±7 h/m$^3$, more preferably 10±6 h/m$^3$, still more preferably 10±5 h/m$^3$, yet more preferably 10±4 h/m$^3$, even more preferably 10±3 h/m$^3$, most preferably 10±2 h/m$^3$, and in particular 10±1 h/m$^3$.

In a preferred embodiment, $AUC_{0-t}$ is within the range of 3750±3500 h·pg/mL, more preferably 3750±3000 h·pg/mL, still more preferably 3750±2500 h·pg/mL, yet more preferably 3750±2000 h·pg/mL, even more preferably 3750±1500 h·pg/mL, most preferably 3750±1000 h·pg/mL, and in particular 3750±500 h·pg/mL.

Preferably, the ratio $AUC_{0-72h}$/dose is within the range from 0.3 to 20 h/m$^3$, more preferably within the range of from 0.4 to 18 h/m$^3$, still more preferably within the range of from 0.5 to 16.5 h/m$^3$ and most preferably within the range of from 0.55 to 12.5 h/m$^3$. In a preferred embodiment, the ratio $AUC_{0-72h}$/dose is within the range of 3±2.5 h/m$^3$, more preferably 3±2 h/m$^3$, still more preferably 3±1.5 h/m$^3$, yet more preferably 3±1 h/m$^3$, even more preferably 3±0.75 h/m$^3$, most preferably 3±0.5 h/m$^3$, and in particular 3±0.25 h/m$^3$. In another preferred embodiment, the ratio $AUC_{0-72h}$/dose is within the range of 6±5 h/m$^3$, more preferably 6±4 h/m$^3$, still more preferably 6±3 h/m$^3$, yet more preferably 6±2 h/m$^3$, even more preferably 6±1.5 h/m$^3$, most preferably 6±1 h/m$^3$, and in particular 6±0.5 h/m$^3$. In still another preferred embodiment, the ratio $AUC_{0-72h}$/dose is within the range of 7.5±7 h/m$^3$, more preferably 7.5±6 h/m$^3$, still more preferably 7.5±5 h/m$^3$, yet more preferably 7.5±4 h/m$^3$, even more preferably 7.5±3 h/m$^3$, most preferably 7.5±2 h/m$^3$, and in particular 7.5±1 h/m$^3$. In yet another preferred embodiment, the ratio $AUC_{0-72h}$/dose is within the range of 9±8 h/m$^3$, more preferably 9±7 h/m$^3$, still more preferably 9±5 h/m$^3$, yet more preferably 9±4 h/m$^3$, even more preferably 9±3 h/m$^3$, most preferably 9±2 h/m$^3$, and in particular 9±1 h/m$^3$.

In a preferred embodiment, $AUC_{0-72}$ is within the range of 2800±2500 h·pg/mL, more preferably 2800±2250 h·pg/mL, still more preferably 2800±2000 h·pg/mL, yet more preferably 2800±1750 h·pg/mL, even more preferably 2800±1500 h·pg/mL, most preferably 2800±1000 h·pg/mL, and in particular 2800±500 h·pg/mL.

In a preferred embodiment, the pharmaceutical dosage form according to the invention is administered once daily during an administration interval comprising an initial phase, during which the plasma concentration time profile substantially changes from day to day, and a steady state phase, during which the plasma concentration time profile does not substantially change from day to day. In this regard, during the steady state phase the plasma concentration time profile may still change during a day, i.e. the plasma concentration measured e.g. 1 hour after administration may substantially differ from the plasma concentration measured e.g. 2, 3, 4, 6, 12 or 20 hours after the same administration on the same day. However, during the steady state phase, the plasma concentration measured X hours after administration on day N does not substantially differ from the plasma concentration measured X hours after the following administration on the following day N+1. Preferably, the initial phase lasts 1, 2, 3, 4 or 5 consecutive days until the steady state phase commences. In a preferred embodiment, during the steady state phase, the pharmaceutical dosage form provides and maintains upon administration once daily pharmacologically effective plasma concentrations of the pharmacologically active agent according to general formula (I) for at least 12 h, preferably at least 18 h, more preferably at least 20 h, yet more preferably at least 22 h and in particular all 24 h of at least 25 pg/mL, at least 30 pg/mL, or at least 35 pg/mL, more preferably at least 40 pg/mL, at least 45 pg/mL, or at least 50 pg/mL, still more preferably at least 60 pg/mL, at least 70 pg/mL, or at least 80 pg/mL, yet more preferably at least 90 pg/mL, at least 100 pg/mL, or at least 110 pg/mL, even more preferably at least 120 pg/mL, at least 130 pg/mL, or at least 140 pg/mL, most preferably at least 150 pg/mL, at least 160 pg/mL, or at least 170 pg/mL, and in particular at least 180 pg/mL, at least 190 pg/mL, or at least 200 pg/mL. In another preferred embodiment, during the steady state phase, the ratio of the maximum plasma concentration $C_{max}$ to the plasma concentration measured 3 h after administration $C_{3h}$, i.e. $C_{max}/C_{3h}$, is not more than 3.9, not more than 3.8, or not more than not more than 3.7, preferably not more than 3.6, not more than 3.5, or not more than not more than 3.4, more preferably not more than 3.3, not more than 3.2, or not more than not more than 3.1, still more preferably not more than 3.0, not more than 2.9, or not more than not more than 2.8, yet more preferably not more than 2.7, not more than 2.6, or not more than not more than 2.5, even more preferably not more than 2.4, not more than 2.3, or not more than not more than 2.2, most preferably not more than 2.1, not more than 2.0, or not more than not more than 1.9, and in particular preferably not more than 1.8, not more than 1.7, or not more than not more than 1.6.

In a preferred embodiment, the pharmaceutical dosage form according to the invention is monolithic.

In another preferred embodiment, the pharmaceutical dosage form according to the invention comprises a core that is surrounded by a coating or by an encapsulating material. In a preferred embodiment, the core is liquid and the pharmacologically active agent according to general formula (I) is dispersed, preferably dissolved in the liquid.

In another preferred embodiment the pharmaceutical dosage form according to the invention provides the pharmacologically active agent according to general formula (I) in form of self- (micro) emulsifying drug delivery systems, solid solutions, nanoparticles, cyclodextrin complexes, liposomes, micelles, micronized and/or amorphous states.

In general terms, the options for formulation of poorly water-soluble drugs include crystalline solid, amorphous and lipid formulations.

The dissolution rate of the pharmacologically active agent from crystalline formulations can be increased by particle size reduction, thereby increasing the surface area for dissolution, e.g. by conventional micronisation of the pharmacologically active agent to particle sizes of about 2-5 μm. In some cases, this is not sufficient and nanocrystal technology is applied. Nanocrystals show a particle size of 100-250 nm, which can be obtained by ball-milling or by dense gas or supercritical fluid technology.

Solid solutions provide and sustain the pharmacologically active agent in an amorphous or semi-amorphous state immobilized in a polymer. Amorphous solutions may contain surfactants and polymers, thereby providing surface-activity during dispersion upon contact with water. Solid solutions can be formed using a variety of technologies such as spray drying and melt extrusion.

Lipid formulations exhibiting different characteristics can be used to disperse and form micellar solutions, including simple solutions and self-emulsifying drug delivery systems (SEDDS). Depending on the excipients, some require digestion (e.g. simple oily liquids), others can easily be absorbed without digestion. Lipid formulations have been classified according to the lipid formulation classification system (LFCS) as follows:

|  | Content of formulation (wt.-%) | | | | |
| --- | --- | --- | --- | --- | --- |
| Excipients in formulation | Type I | Type II | Type IIIA | Type IIIB | Type IV |
| Oil: triglycerides or mixed mono- and diglycerides | 100 | 40-80 | 40-80 | <20 | — |
| Water-insoluble surfactants (HLB < 12) | — | 20-60 | — | — | 0-20 |
| Water-soluble surfactants (HLB > 12) | — | — | 20-40 | 20-50 | 30-80 |
| Hydrophilic co-solvent | — | — | 0-40 | 20-50 | 0-50 |

Another option is the formation of cyclodextrin complexes, in which the pharmacologically active agent is located in the cavity of the cyclodextrin and is thereby molecularly present in a more soluble form in presence of aqueous media. The success of the fitting strongly depends on the quality of the cyclodextrins as well as on the physicochemical properties and size of the pharmacologically active agent.

In a preferred embodiment, the pharmaceutical dosage form according to the invention can be regarded as a self emulsifying drug delivery system (SEDDS).

For that purpose, the pharmacologically active agent according to general formula (I) is preferably embedded in a self-emulsifying formulation. A so called self emulsifying drug delivery system (SEDDS) is a drug delivery system that uses an emulsion achieved by chemical rather than mechanical means. That is, by an intrinsic property of the drug formulation, rather than by special mixing and handling. Said formulation dilutes in aqueous media and results in an emulsion. In case that the average droplet size is smaller than or equal to 50 nm, the self emulsifying drug delivery system (SEDDS) is referred to as self-micro emulsifying drug delivery system (SMEDDS). According to the lipid formulation classification system, these formulations are typically assigned to the group of type III formulations.

A preferred sub-group of SEDDSs are self-emulsifying oily formulations (SEOF). SEOFs typically comprise a natural or synthetic oil, surfactant and hydrophilic solvent and sometimes co-solvents. The principal characteristic of SEOFs is their ability to form fine oil-in-water emulsions or micro emulsions upon mild agitation following dilution by aqueous phases.

These formulations can disperse in the gastrointestinal lumen to form micro emulsions or fine emulsions, upon dilution with gastrointestinal fluids.

In another preferred embodiment, the pharmaceutical dosage form contains the pharmacologically active agent according to general formula (I) in form of a solid solution, i.e. molecularly dispersed in a solid matrix, so that preferably the pharmaceutical dosage form as such has an amorphous or semi-amorphous nature. The solid solution preferably comprises the pharmacologically active agent according to general formula (I) in a molecular disperse form and an amorphous polymer matrix having a comparatively large specific surface. The pharmacologically active agent according to general formula (I) is preferably present in a molecular disperse form, i.e. the compound is truly solved and evenly spread in the solidified solution. The particle size of the compound is neither microcrystalline nor fine crystalline. The typical particle size is preferably from 0.1-1 μm.

In still another preferred embodiment, the pharmacologically active agent according to general formula (I) is provided by means of a nanotechnological formulation with an average size of the nanoparticles of preferably less than 1 μm. The pharmacologically active agent according to general formula (I) is preferably blended with the nanoparticles and thus adsorbed to the surface of the nanoparticles. The nanoparticles are preferably selected from organic nanoparticles and inorganic nanoparticles.

Organic nanoparticles preferably contain small proteins which are present as a cluster or an agglomerate of small proteins, oligopeptides or lipids.

Inorganic nanoparticles preferably contain crystalline silicates. These silicates are from mineral origin or artificial silicates like metallosilicates (e.g. zeolites). In a preferred embodiment, the nanoparticles are modified in a way that they bear an electrostatic charge. The nanoparticles are preferably ultra finely grounded silicates and the pharmacologically active agent according to general formula (I) is preferably bounded to the micro porous surface of the nanoparticles.

The formation of nanoparticles is known to a person skilled in the art. One method is to produce colloidal nanoparticles as carriers for oral drug release by spraying the pharmacologically active agent according to general formula (I) under pressure at a defined temperature, together with a suitable carrier material like protamine, through jets, which are equipped with perforated strainers, into strongly cooled towers. The result of the fast cooling is an amorphous phase consisting of nanoparticles. Another method is to blend the pharmacologically active agent according to general formula (I) with suitable macromolecules in solution. By adding hydrophobic compounds, solvent molecules are removed from the solution and desolvation occurs. For this reason the formation of very tiny particles takes place wherein the pharmacologically active agent according to general formula (I) is integrated. For a hardening of the formed nanoparticles a crosslinker may be added to the solution.

To produce for example a solid lipid nanoparticle the method of high-pressure-homogenization and subsequent spray-cooling can be used. Preferably, the pharmacologically active agent according to general formula (I) is dissolved in a suitable solvent or in form of sub-micro particles. If applicable, a lipid vehicle and a surfactant may be added to the solution. Finally fine filler materials as outer phase as well as glidants and further surfactants may be added to fill the obtained formulation into e.g. capsules such as hard gelatin capsules.

In yet another preferred embodiment, the pharmacologically active agent according to general formula (I) are provided as cyclodextrin (inclusion) complexes.

Cyclodextrins are composed of sugar molecules forming a ring and typically comprising 5 or more α-D-glycopyranoside units which are linked via the 1-4 position. The typical number of connected sugar monomers ranges from 6 to 8 units. A six membered sugar ring molecule is called α-cyclodextrin. A seven membered sugar ring molecule is called β-cyclodextrin and an eight membered sugar ring molecule is called γ-cyclodextrin. The shape of these compounds is a toroid with the larger and the smaller openings exposed to the solvent. Due to this formation the inner part of the toroid is not hydrophobic, but considerably less hydrophilic than the aqueous environment and thus able to host hydrophobic molecules. The outer part of the toroid is sufficiently hydrophilic to render cyclodextrins water solubility.

The inclusion of the pharmacologically active ingredient according to general formula (I) in cyclodextrins greatly modifies the physical and chemical properties. In most cases the mechanism of controlled degradation of such complexes and resultant drug release is based on pH change of aqueous solutions, leading to the cleavage of hydrogen or ionic bonds between the cyclodextrins and the included molecules. Alternative means for the disruption of the complexes take advantage of heating or action of enzymes able to cleave α-1-4 linkages between α-D-glycopyranosides.

In another preferred embodiment, the pharmacologically active agent according to general formula (I) is provided in form of liposomes. A liposome is preferably composed of phospholipids and is preferably of spherical shape. The shell of this shape is preferably a lamellar or bilayer structure. Another type of phospholipids arrangement is a monolayer.

Phospholipids comprise molecules with an amphiphilic character i.e. the molecules have a hydrophobic (lipophilic) and a hydrophilic (lipophobic) part. In the presence of water, the hydrophilic part is attracted to the water and forms a surface facing to the water, while the hydrophobic part is repelled by the water and forms a surface away from the water. Hence the amphiphilic molecules arrange themselves in one of the mentioned types.

The bilayer structures preferably arrange in a spherical shape wherein the inner part is filled with an aqueous solution. This type is called "liposome". The hydrophobic parts of the molecules face each other in the middle of the layer and the hydrophilic parts of the molecules face the water molecules outside of the liposome. The aqueous solution inside the liposome is the same as it is outside of the liposome. Ingredients solved in this aqueous solution, e.g. the pharmacologically active agents according to general formula (I), are in this way inside of the liposome. A typical diameter of the liposomes is between 25 nm and 1 μm. The smaller ones (25 nm-200 nm) are made of one single bilayer while the bigger ones (200 nm-1 μm) comprise more bilayer shells on the top of each other.

The monolayer structures also arrange in spherical shapes. Due to the amphiphilic character of the molecules and the spherical shape of the monolayer structures, the inner part of the spherical structures is filled with/formed by the hydrophobic parts of the molecules. These types are called micelles. There is no solvent inside the structure. In a preferred embodiment, the inner parts of the micelles contain the pharmacologically active agents according to general formula (I).

In another preferred embodiment the pharmacologically active agent according to general formula (I) is provided in a micronized state. By means of micronization technique particles of the pharmacologically active agent according to general formula (I) with a diameter in nanometer scale can be prepared. Said particles have a large surface to volume ratio.

Milling and grinding is a useful method to obtain particles in nanometer scale. Sophisticated techniques for the micronization include RESS (rapid expansion of supercritical solutions), SAS (supercritical anti solvent) and the PGSS (particles from gas saturated solutions).

The RESS method uses a supercritical fluid wherein the pharmacologically active agent according to general formula (I) is dissolved under high pressure and temperature thereby yielding a homogenous supercritical phase. After expanding the solution through a nozzle, small particles are formed. Due to the expansion at the end of the nozzle the solved pharmacologically active agent according to general formula (I) precipitates as crystals and encloses small amounts of the solvent. The solvent changes from the supercritical fluid state to the normal state, preferred the gas phase, and breaks the crystals from inside-out. In this way and due to the fact that the crystals collide with each other, particles with a diameter in nanometer scale are formed.

In the SAS method the pharmacologically active agent according to general formula (I) is dissolved in a preferably organic solvent. A supercritical fluid is added to the solution under pressure and thus forced to also dissolve in the solvent. In consequence, the volume of the complete system is increased and the solubility of the pharmacologically active agent according to general formula (I) is decreased. Due to its decreased solubility, the compound according to general formula (I) precipitates and forms particles having a small diameter.

The PGSS method is similar to the SAS method. Here, the pharmacologically active agent according to general formula (I) is melted and a supercritical fluid is dissolved in the melt. Due to the expansion through a nozzle, the pharmacologically active agent according to general formula (I) precipitates and forms particles in a nanometer scale.

In a preferred embodiment, the pharmaceutical dosage form according to the invention contains a non-ionic surfactant (e.g. Cremophor® EL, Cremophor® RH 40, Cremophor® RH 60, d-alpha-tocopherol polyethylene glycol 1000 succinate, polysorbate 20, polysorbate 80, Solutol® HS 15, sorbitan monooleate, poloxamer 407, Labrafil® M-1944CS, Labrafil® M-2125CS, Labrasol®, Gelucire® 44/14, Softigen® 767, and mono- and di-fatty acid esters of PEG 300, 400 or 1750); and/or an anionic surfactant (e.g., Konakion® MM, Cernevit® sodium lauryl sulfate (sodium dodecyl sulfate, e.g. Texapon® K12), sodium cetyl sulfate (e.g. Lanette E®), sodium cetylstearyl sulfate, sodium stearyl sulfate, sodium dioctylsulfosuccinate (docusate sodium); and/or a water insoluble lipid (e.g. castor oil, corn oil cottonseed oil, olive oil, peanut oil, peppermint oil, safflower oil, sesame oil, soybean oil, hydrogenated vegetable oils, hydrogenated soybean oil, and medium chain triglycerides of coconut oil and palm seed oil); and/or an organic liquid/semi-solid (e.g. beeswax, d-alpha-tocopherol, oleic acid, medium chain mono- and diglycerides); and/or a cyclodextrin (e.g. alpha-cyclodextrin, beta-cyclodextrin, hydroxypropyl-beta-cyclodextrin, and sulfobutylether-beta-cyclodextrin); and/or a phospholipid (e.g. hydrogenated soy phosphatidylcholine, distearoylphosphatidylglycerol, L-alpha-dimyristoylphosphatidylcholine, and L-alpha-dimyristoylphosphatidylglycerol).

Preferably, the pharmacologically active agent according to general formula (I) is molecularly dispersed in a matrix.

In a preferred embodiment, the pharmacologically active agent according to general formula (I) is molecularly dispersed in a non-crystalline matrix.

In another preferred embodiment, the pharmacologically active agent according to general formula (I) is molecularly dispersed in a non-amorphous matrix.

Preferably, the pharmacologically active agent according to general formula (I) is homogeneously distributed in the pharmaceutical dosage form according to the invention. The content of the pharmacologically active agent according to general formula (I) of two segments of the pharmaceutical dosage form having a volume of 1.0 mm$^3$ each, deviate from one another by preferably not more than ±10%, more preferably not more than more than ±7.5%, still more preferably not more than ±5.0%, most preferably not more than ±2.5%, and in particular not more than ±1.0%. When the pharmaceutical dosage form is encapsulated or film-coated, said two segments of the pharmaceutical dosage form having a volume of 1.0 mm$^3$ each are preferably segments of the core, i.e. do not contain any encapsulating medium or film coating, respectively.

Preferably, the pharmaceutical dosage form according to the invention is characterized by a comparatively homogeneous distribution of density. Preferably, the densities of two segments of the pharmaceutical dosage form having a volume of 1.0 mm$^3$ each, deviate from one another by not more than ±10%, more preferably not more than more than ±7.5%, still more preferably not more than ±5.0%, most preferably not more than ±2.5%, and in particular not more than ±1.0%. When the pharmaceutical dosage form is encapsulated, said two segments of the pharmaceutical dosage form having a volume of 1.0 mm$^3$ each are preferably segments of the core, i.e. do not contain any encapsulating medium or film coating.

In a preferred embodiment, the pharmaceutical dosage form further contains a surfactant.

For the purpose of the specification, the term "surfactant" refers to any compound that contains at least one hydrophobic group and at least one hydrophilic group. Preferably, the surfactant contains at least one terminal hydrophobic group (tail) and at least one terminal hydrophilic group (head).

The hydrophobic group is preferably selected from the group consisting of hydrocarbon, alkyl ether, fluorocarbon and siloxan groups.

In a preferred embodiment, the surfactant contains at least one aliphatic group comprising at least 3 carbon atoms, more preferably at least 4 carbon atoms, still more preferably at least 6 carbon atoms, yet more preferably 6 to 30 carbon atoms, and most preferably 8 to 24 carbon atoms. The aliphatic group may be a saturated or unsaturated, branched or unbranched (linear), terminal or internal aliphatic group.

Preferably, the surfactant contains at least one group derivable from a saturated or unsaturated fatty acid or from a saturated or unsaturated fatty alcohol, which group is preferably an ether, carboxylic acid ester or sulfuric acid ester group. Preferably, the saturated or unsaturated fatty acid or fatty alcohol contains at least 6 carbon atoms, yet more preferably 6 to 30 carbon atoms, and most preferably 8 to 24 carbon atoms.

In a preferred embodiment, the surfactant contains at least one group derivable from a saturated or unsaturated fatty acid, preferably $C_6$ to $C_{30}$ fatty acid, more preferably $C_8$ to $C_{24}$ fatty acid, and most preferably $C_{12}$ to $C_{22}$ fatty acid. Examples for suitable fatty acids are lauric acid, myristic acid, palmitic acid, stearic acid, arachidic acid, behenic acid, lignoceric acid, 12-hydroxystearic acid, oleic acid and ricinoleic acid.

In another preferred embodiment, the surfactant contains at least one group derivable from a saturated or unsaturated fatty alcohol, preferably $C_6$ to $C_{30}$ fatty alcohol, more preferably $C_8$ to $C_{24}$ fatty alcohol, and most preferably $C_{12}$ to $C_{22}$ fatty alcohol. Examples for suitable fatty alcohols are cetyl alcohol, stearyl alcohol, 2-octyldodecane-1-ol and 2-hexyldecane-1-ol.

Preferably, the surfactant has a molecular weight of at most 20,000 g/mol, more preferably at most 15,000 g/mol, still more preferably at most 10,000 g/mol, yet more preferably at most 5,000 g/mol, even more preferably at most 4,000 g/mol, most preferably at most 3,000 g/mol, and in particular within the range of from 100 g/mol to 2,500 g/mol.

Preferably, the surfactant is contained in a matrix in which the pharmacologically active agent according to general formula (I) is dispersed, preferably molecularly.

In a preferred embodiment, the pharmacologically active agent according to general formula (I) and the surfactant are intimately homogeneously distributed in a matrix so that the matrix does not contain any segments where either the pharmacologically active agent according to general formula (I) is present in the absence of the surfactant or where the surfactant is present in the absence of the pharmacologically active agent according to general formula (I).

In a preferred embodiment, the pharmaceutical dosage form contains a surfactant. In another preferred embodiment, the pharmaceutical dosage form contains a mixture of two or more surfactants.

In a preferred embodiment, the surfactant acts as an oil-in-water (O/W) emulsifier. In another preferred embodiment, the surfactant acts as a water-in-oil (W/O) emulsifier.

Preferably, the pharmaceutical dosage form contains a surfactant having a hydrophiliclipophilic balance (HLB) of at least 10 or at least 11. More preferably, the hydrophilic-lipophilic balance (HLB) is at least 12 or at least 13. Most preferably, the hydrophilic-lipophilic balance (HLB) ranges within 14 and 16.

Preferably, the hydrophilic-lipophilic balance (HLB) of the surfactant is at most 30, more preferably at most 28, still more preferably at most 26, yet more preferably at most 24, even more preferably at most 22, most preferably at most 20 and in particular at most 18.

In another preferred embodiment, the hydrophilic-lipophilic balance (HLB) of the surfactant is at least 27, more preferably at least 29, still more preferably at least 31, yet more preferably at least 33, even more preferably at least 35, most preferably at least 37 and in particular at least 39. An especially preferred surfactant of this type is sodium lauryl sulfave having an HLB value of about 40.

In a preferred embodiment, the HLB value of the surfactant is within the range of 10±3.5, more preferably 10±3, still more preferably 10±2.5, yet more preferably 10±2, even more preferably 10±1.5, most preferably 10±1, and in particular 10±0.5. In another preferred embodiment, the HLB value of the surfactant is within the range of 12±3.5, more preferably 12±3, still more preferably 12±2.5, yet more preferably 12±2, even more preferably 12±1.5, most preferably 12±1, and in particular 12±0.5. In still another preferred embodiment, the HLB value of the surfactant is within the range of 14±3.5, more preferably 14±3, still more preferably 14±2.5, yet more preferably 14±2, even more preferably 14±1.5, most preferably 14±1, and in particular 14±0.5. In another preferred embodiment, the HLB value of the surfactant is within the range of 15±3.5, more preferably 15±3, still more preferably 15±2.5, yet more preferably 15±2, even more preferably 15±1.5, most preferably 15±1, and in particular 15±0.5. In yet another preferred embodiment, the HLB value of the surfactant is within the range of 16±3.5, more preferably 16±3, still more preferably 16±2.5, yet more preferably 16±2, even more preferably 16±1.5, most preferably 16±1, and in particular 16±0.5. In another preferred embodiment, the HLB value of the surfactant is within the range of 18±3.5, more preferably 18±3, still more preferably 18±2.5, yet more preferably 18±2, even more preferably 18±1.5, most preferably 18±1, and in particular 18±0.5.

In another preferred embodiment, the HLB value of the surfactant is within the range of 30±3.5, more preferably 30±3, still more preferably 30±2.5, yet more preferably 30±2, even more preferably 30±1.5, most preferably 30±1, and in particular 30±0.5. In another preferred embodiment, the HLB value of the surfactant is within the range of 32±3.5, more preferably 32±3, still more preferably 32±2.5, yet more preferably 32±2, even more preferably 32±1.5, most preferably 32±1, and in particular 32±0.5. In still another preferred embodiment, the HLB value of the surfactant is within the range of 34±3.5, more preferably 34±3, still more preferably 34±2.5, yet more preferably 34±2, even more preferably 34±1.5, most preferably 34±1, and in particular 34±0.5. In another preferred embodiment, the HLB value of the surfactant is within the range of 36±3.5, more preferably 36±3, still more preferably 36±2.5, yet more preferably 36±2, even more preferably 36±1.5, most preferably 36±1, and in particular 36±0.5. In yet another preferred embodiment, the HLB value of the surfactant is within the range of 38±3.5, more preferably 38±3, still more preferably 38±2.5, yet more preferably 38±2, even more preferably 38±1.5, most preferably 38±1, and in particular 38±0.5. In another preferred embodiment, the HLB value of the surfactant is within the range of 40±3.5, more preferably 40±3, still more preferably 40±2.5, yet more preferably 40±2, even more preferably 40±1.5, most preferably 40±1, and in particular 40±0.5.

The surfactant can be ionic, amphoteric or non-ionic.

Suitable amphoteric surfactants include phospholipids, in particular lecithins such as soya bean lecithins.

In a preferred embodiment, the pharmaceutical dosage form contains an ionic surfactant, in particular an anionic surfactant.

Suitable anionic surfactants include but are not limited to sulfuric acid esters such as sodium lauryl sulfate (sodium dodecyl sulfate, e.g. Texapon® K12), sodium cetyl sulfate (e.g. Lanette E®), sodium cetylstearyl sulfate, sodium stearyl sulfate, sodium dioctylsulfosuccinate (docusate sodium), di-[2-ethylhexyl]-succinate; and the corresponding potassium or calcium salts thereof.

Preferably, the anionic surfactant has the general formula (II-a)

$$C_nH_{2n+1}O-SO_3^-M^+ \qquad (II\text{-}a),$$

wherein n is an integer of from 8 to 30, preferably 10 to 24, more preferably 12 to 18; and M is selected from Li$^+$, Na$^+$, K$^+$, NH$_4^+$ ½Mg$^{2+}$ and ½Ca$^{2+}$.

Further suitable anionic surfactants include salts of cholic acid including sodium glycocholate (e.g. Konakion® MM, Cernevit®), sodium taurocholate and the corresponding potassium or ammonium salts.

In another preferred embodiment, the pharmaceutical dosage form contains a non-ionic surfactant. Suitable non-ionic surfactants include but are not limited to
fatty alcohols that may be linear or branched, such as cetylalcohol, stearylalcohol, cetylstearyl alcohol, 2-octyldodecane-1-ol and 2-hexyldecane-1-ol;
sterols, such as cholesterole;
partial fatty acid esters of sorbitan such as sorbitanmonolaurate, sorbitanmonopalmitate, sorbitanmonostearate, sorbitantristearate, sorbitanmonooleate, sorbitansesquioleate and sorbitantrioleate;
partial fatty acid esters of polyoxyethylene sorbitan (polyoxyethylene-sorbitan-fatty acid esters), preferably a fatty acid monoester of polyoxyethylene sorbitan, a fatty acid diester of polyoxyethylene sorbitan, or a fatty acid triester of polyoxyethylene sorbitan; e.g. mono- and trilauryl, palmityl, stearyl and °leyl esters, such as the type known under the name "polysorbat" and commercially available under the trade name "Tween" including Tween® 20 [polyoxyethylene(20)sorbitan monolaurate], Tween® 21 [polyoxyethylene(4)sorbitan monolaurate], Tween® 40 [polyoxyethylene(20)sorbitan monopalmitate], Tween® 60 [polyoxyethylene(20)sorbitan monostearate], Tween® 65 [polyoxyethylene(20) sorbitan tristearate], Tween® 80 [polyoxyethylene(20) sorbitan monooleate], Tween 81 [polyoxyethylene(5) sorbitan monooleate], and Tween® 85 [polyoxyethylene(20)sorbitan trioleate]; preferably a fatty acid monoester of polyoxyethylenesorbitan according to general formula (II-b)

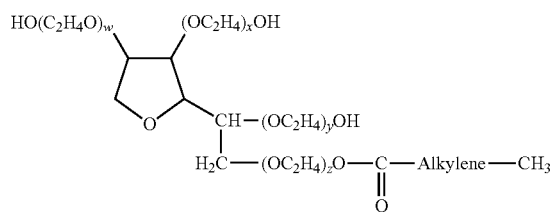

(II-b)

wherein (w+x+y+z) is within the range of from 15 to 100, preferably 16 to 80, more preferably 17 to 60, still more preferably 18 to 40 and most preferably 19 to 21; and alkylene is an optionally unsaturated alkylene group comprising 6 to 30 carbon atoms, more preferably 8 to 24 carbon atoms and most preferably 10 to 16 carbon atoms;
polyoxyethyleneglycerole fatty acid esters such as mixtures of mono-, di- and triesters of glycerol and di- and monoesters of macrogols having molecular weights within the range of from 200 to 4000 g/mol, e.g., macrogolglycerolcaprylocaprate, macrogolglycerollaurate, macrogolglycerolococoate, macrogolglycerollinoleate, macrogol-20-glycerolmonostearate, macrogol-6-glycerolcaprylocaprate, macrogolglyceroloeate; macrogolglycerolstearate, macrogolglycerolhydroxystearate (e.g. Cremophor® RH 40), and macrogolglycerolrizinoleate (e.g. Cremophor® EL);
polyoxyethylene fatty acid esters, the fatty acid preferably having from about 8 to about 18 carbon atoms, e.g. macrogololeate, macrogolstearate, macrogol-15-hydroxystearate, polyoxyethylene esters of 12-hydroxystearic acid, such as the type known and commercially available under the trade name "Solutol HS 15"; preferably according to general formula (II-c)

$$CH_3CH_2-(OCH_2CH_3)_n-O-CO-(CH_2)_mCH_3 \qquad (II\text{-}c)$$

wherein n is an integer of from 6 to 500, preferably 7 to 250, more preferably 8 to 100, still more preferably 9 to 75, yet more preferably 10 to 50, even more preferably 11 to 30, most preferably 12 to 25, and in particular 13 to 20; and
wherein m is an integer of from 6 to 28; more preferably 6 to 26, still more preferably 8 to 24, yet more preferably 10 to 22, even more preferably 12 to 20, most preferably 14 to 18 and in particular 16;

polyoxyethylene fatty alcohol ethers, e.g. macrogolcetylstearylether, macrogollarylether, macrogololeylether, macrogolstearylether;

polyoxypropylene-polyoxyethylene block copolymers (poloxamers);

fatty acid esters of saccharose; e.g. saccharose distearate, saccharose dioleate, saccharose dipalmitate, saccharose monostearate, saccharose monooleate, saccharose monopalmitate, saccharose monomyristate and saccharose monolaurate;

fatty acid esters of polyglycerol, e.g. polyglycerololeate;

polyoxyethylene esters of alpha-tocopheryl succinate, e.g. D-alpha-tocopheryl-PEG-1000-succinate (TPGS);

polyglycolyzed glycerides, such as the types known and commercially available under the trade names "Gelucire 44/14", "Gelucire 50/13 and "Labrasol";

reaction products of a natural or hydrogenated castor oil and ethylene oxide such as the various liquid surfactants known and commercially available under the trade name "Cremophor"; and partial fatty acid esters of multifunctional alcohols, such as glycerol fatty acid esters, e.g. mono- and tri-lauryl, palmityl, stearyl and ° leyl esters, for example glycerol monostearate, glycerol monooleate, e.g. glyceryl monooleate 40, known and commercially available under the trade name "Peceol"; glycerole dibehenate, glycerole distearate, glycerole monolinoleate; ethyleneglycol monostearate, ethyleneglycol monopalmitostearate, pentaerythritol monostearate.

In a particularly preferred embodiment, the pharmaceutical dosage form according to the invention comprises a surfactant or mixture of different surfactants obtainable by (i) esterifying saturated or unsaturated $C_{12}$-$C_{18}$-fatty acids, optionally bearing a hydroxyl group, with a polyethylene glycol and optionally, glycerol; wherein the polyethylene glycol preferably comprises 10 to 40 ethylene oxide units (—$CH_2CH_2O$—); and/or (ii) etherifying triglycerides of saturated or unsaturated $C_{12}$-$C_{18}$-fatty acids bearing a hydroxyl group with ethylene oxide so that a polyethylene glycol moiety is linked to the hydroxyl group of the $C_{12}$-$C_{18}$-fatty acids via an ether bond; wherein the polyethylene glycol moiety preferably comprises 30 to 50 ethylene oxide units (—$CH_2CH_2O$—).

Preferably, the surfactant is selected from the group consisting of macrogolhydroxystearate, macrogolglycerylhydroxystearate and macrogolglyceryllaurate, wherein the macrogol moiety preferably comprises 15 to 45 ethylene oxide units.

Especially preferred surfactants of this class that are contained in the pharmaceutical dosage form according to the invention are non-ionic surfactants having a hydrophilic-lipophilic balance (HLB) of at least 10, in particular non-ionic surfactants having an HLB value of at least 12, more in particular non-ionic surfactant's having an HLB value within 14 and 16. Examples for this type of surfactants are the above-listed surfactants "polysorbate 80" (Tween® 80) and "Solutol® HS 15".

Solutol® HS-15 is a mixture of polyethyleneglycol 660 12-hydroxystearate and polyethylene glycol. It is a white paste at room temperature that becomes liquid at about 30° C. and has an HLB of about 15.

Tween® 80 [polyoxyethylene(20)sorbitan monooleate] is liquid at room temperature, has a viscosity of 375-480 mPa s and has an HLB of about 15.

In another preferred embodiment the pharmaceutical dosage form according to the invention contains a mixture of at least one surfactant having a HLB value of at least 10 (hydrophilic surfactant) and at least one surfactant having a HLB value below 10 (lipophilic surfactant). For example, the dosage form may contain macrogol-glycerolhydroxystearat 40 (e.g., Cremophor® RH 40) as the hydrophilic surfactant component and glyceryl monooleate 40 (e.g., Peceol®) as the lipophilic surfactant component.

Preferably, the relative weight ratio of the surfactant having a HLB value of at least 10 (hydrophilic surfactant) and the surfactant having a HLB value below 10 (lipophilic surfactant) is within the range of 15:1 to 1:20, more preferably 10:1 to 1:15, still more preferably 8:1 to 1:12, yet more preferably 6:1 to 1:10, even more preferably 5:1 to 1:7, most preferably 4:1 to 1:4 and in particular 2:1 to 1:2.

In a preferred embodiment, the content of the surfactant is at least 0.001 wt.-% or at least 0.005 wt.-%, more preferably at least 0.01 wt.-% or at least 0.05 wt.-%, still more preferably at least 0.1 wt.-%, at least 0.2 wt.-%, or at least 0.3 wt.-%, yet more preferably at least 0.4 wt.-%, at least 0.5 wt.-%, or at least 0.6 wt.-%, and in particular at least 0.7 wt.-%, at least 0.8 wt.-%, at least 0.9 wt.-%, or at least 1.0 wt.-%, based on the total weight of the pharmaceutical dosage form.

In another preferred embodiment, particularly when the pharmaceutical dosage form contains an encapsulated core, the content of the surfactant is at least 10 wt.-%, more preferably at least 15 wt.-%, still more preferably at least 20 wt.-%, yet more preferably at least 25 wt.-% and in particular at least 30 wt.-%, based on the total weight of the composition forming the core. In a preferred embodiment, the content of the surfactant ranges preferably from 0.1 wt.-% to 95 wt.-%, more preferably from 1 wt.-% to 95 wt.-%, still more preferably from 5 wt.-% to 90 wt.-%, yet more preferably from 10 wt.-% to 80 wt.-%, most preferably from 20 wt.-% to 70 wt.-%, and in particular from 30 wt.-% to 75 wt.-%, based on the total weight of the composition forming the core.

In a preferred embodiment, the pharmaceutical dosage form contains a core that is encapsulated by an encapsulating medium. The core can be liquid, semi-liquid or solid.

Preferably, said encapsulating medium is a soft gelatin capsule or a hard gelatin capsule, in particular a hard gelatin capsule.

In one preferred embodiment, the pharmaceutical dosage form comprises a liquid core encapsulated by a solid material, wherein the pharmacologically active agent according to general formula (I) is dispersed in the liquid core. Preferably, the solid material is a hard gelatin capsule.

In another preferred embodiment, the pharmaceutical dosage form according to the invention contains a self-emulsifying formulation in which the pharmacologically active agent according to general formula (I) is preferably embedded. Preferably, the pharmacologically active agent according to general formula (I) is molecularly dispersed in the other ingredients of liquid core. For the purpose of the specification, "molecularly dispersed in a liquid core", e.g. in the other ingredients of the liquid core, means that a substantial portion of the overall content of the pharmacologically active agent according to general formula (I) is present in non-crystalline form, i.e. does not provide X-ray reflexes. Preferably, the pharmacologically active agent according to general formula (I) is dissolved in the other ingredients of the core. Preferably, the content of non-crystalline pharmacologically active agent according to general formula (I) is at least 60 wt.-%, more preferably at least 65 wt.-%, still more preferably at least 70 wt.-%, yet more preferably at least 75 wt.-%, even more preferably at least 80 wt.-%, most preferably at least 85 wt.-%, and in particular at least 90 wt.-%, based on the total content of pharmacologically active agent according to general formula (I).

In a preferred embodiment, the self-emulsifying formulation contains the surfactant and an oil.

In another preferred embodiment, the self-emulsifying formulation is a self-emulsifying oily formulation (SEOF), i.e. it comprises the surfactant, the oil and additionally a hydrophilic solvent.

For the purpose of the specification, an oil is preferably to be regarded as any substance that is liquid at ambient temperatures or has a melting point below 70° C. and is hydrophobic but soluble in organic solvents.

Preferably, the oil is a $C_{12}$-$C_{18}$-fatty acid ester of a monoalcohol (e.g. $C_1$-$C_{12}$-alkylalcohols), a di-$C_{12}$-$C_{18}$-fatty acid ester of a dialcohol (e.g. ethylene glycol) or tri-$C_{12}$-$C_{18}$-fatty acid ester of a trialcohol (e.g. glycerol).

Preferably, the oil has a melting point below 60° C., more preferably below 55° C., still more preferably below 50° C., yet more preferably below 45° C., even more preferably below 40° C., most preferably below 35° C. and in particular below 30° C.

Preferably, the pure oil has a density within the range of 0.94±0.07 g/cm³, more preferably 0.94±0.06 g/cm³, still more preferably 0.94±0.05 g/cm³, yet more preferably 0.94±0.04 g/cm³, even more preferably 0.94±0.03 g/cm³, most preferably 0.94±0.02 g/cm³, and in particular 0.94±0.01 g/cm³.

Preferably, the pure oil has a viscosity at 20° C. measured in accordance with Ph. Eur. 2.2.8, within the range of 30±9 mPas, more preferably 30±8 mPas, still more preferably 30±7 mPas, yet more preferably 30±6 mPas, even more preferably 30±5 mPas, most preferably 30±4 mPas, and in particular 30±3 mPas.

In a preferred embodiment, the oil is selected from the group consisting of
- saturated $C_8$ to $C_{14}$ fatty acids, such as myristic acid;
- unsaturated $C_8$ to $C_{18}$ fatty acids and their esters, such as oleic acid and ethyl oleate;
- mixtures of saturated and unsaturated $C_8$ to $C_{18}$ fatty acids, such as soybean oil and peanut oil; and
- triglycerides of fatty acids, preferably of $C_6$ to $C_{12}$ fatty acids, more preferably of $C_6$ to $C_{10}$ fatty acids, such as the caprylic/capric triglyceride mixtures, most preferably medium-chain triglycerides according to Ph. Eur. or USP, e.g. known and commercially available under the trade names "Captex 355" and Miglyol 812"; and
- propylene glycol fatty acid esters such as propylene glycol monocaprylate (known and commercially available under the trade names "Capryol 90").

Especially preferred are medium-chain triglycerides according to Ph. Eur. or USP such as said caprylic/capric triglyceride mixtures.

In a preferred embodiment, the content of the oil in the pharmaceutical dosage form is within the range of from 1 wt.-% to 90 wt.-%, preferably from 2 wt.-% to 80 wt.-%, more preferably from 5 wt.-% to 60 wt.-%, still more preferably from 10 wt.-% to 50 wt.-% and most preferably from 15 wt.-% to 30 wt.-%, preferably based on the total weight of the core.

In a preferred embodiment, the relative weight ratio of the surfactant to the oil is within the range of from 20:1 to 1:20, more preferably 10:1 to 1:10, still more preferably 7.5:1 to 1:5, yet more preferably 7:1 to 1:1, most preferably 5:1 to 1.5:1 and in particular 4:1 to 2:1.

In another preferred embodiment, particularly when the pharmaceutical dosage form is a tablet, the content of the surfactant ranges preferably from 0.001 wt.-% to 95 wt.-%, more preferably from 0.01 wt.-% to 50 wt.-%, still more preferably from 0.1 wt.-% to 20 wt.-%, yet more preferably from 0.15 wt.-% to 15 wt.-%, most preferably from 0.2 wt.-% to 10 wt.-%, and in particular from 0.25 wt.-% to 5 wt.-%, based on the total weight of the dosage form. In a preferred embodiment, the content of the surfactant is at most 25 wt.-%, more preferably at most 20 wt.-%, still more preferably at most 15 wt.-%, yet more preferably at most 10 wt.-% and in particular at most 5 wt.-%, based on the total weight of the pharmaceutical dosage form. In case that the dosage form is coated, the indication "wt.-%" preferably refers to the weight of the surfactant per total weight of the composition forming the core, i.e. the pharmaceutical dosage form without its coating.

In a preferred embodiment, the content of the surfactant is within the range of 1±0.7 wt.-%, more preferably 1±0.6 wt.-%, still more preferably 1±0.5 wt.-%, yet more preferably 1±0.4 wt.-%, even more preferably 1±0.3 wt.-%, most preferably 1±0.2 wt.-%, and in particular 1±0.1 wt.-%

Preferably, the self-emulsifying formulation is present as the liquid core, encapsulated by a hard gelatin capsule.

In a preferred embodiment, the self-emulsifying formulation further contains a hydrophilic solvent.

Preferably, the hydrophilic solvent is an organic alcohol such as an organic monoalcohol, organic dialcohol or organic trialcohol.

Preferably, the pure hydrophilic solvent has a boiling point at ambient pressure within the range of 78±22° C., more preferably 78±18° C., still more preferably 78±15° C., yet more preferably 78±12° C., even more preferably 78±8° C., most preferably 78±5° C., and in particular 78±2° C.

Preferably, the hydrophilic solvent is selected from the group ethanol, isopropanol, glycerol and propylene glycol; especially preferred is ethanol. Preferably, the content of the hydrophilic solvent is within the range of from about 1 wt.-% to about 90 wt.-%, preferably from about 2 wt.-% to about 80 wt.-%, more preferably from about 5 wt.-% to about 60 wt.-%, still more preferably from about 10 wt.-% to about 50 wt.-%, most preferably from about 15 wt.-% to about 30 wt.-%, preferably based on the total weight of the core.

In a preferred embodiment, the pharmaceutical dosage form contains a liquid core comprising the pharmacologically active agent according to general formula (I), a surfactant, an oil and a hydrophilic solvent, wherein the relative weight ratio of surfactant:oil:hydrophilic solvent is within the range of 60:20±17.5:20±17.5, more preferably 60:20±15:20±15, still more preferably 60:20±12.5:20±12.5, yet more preferably 60:20±10:20±10, even more preferably 60:20±7.5:20±7.5, most preferably 60:20±5:20±5, and in particular 60:20±2.5:20±2.5.

In another preferred embodiment, the pharmaceutical dosage form contains a liquid core comprising the pharmacologically active agent according to general formula (I), a surfactant having a HLB value of at least 10 (hydrophilic surfactant), an oil and a surfactant having a HLB value below 10 (lipophilic surfactant), wherein the relative weight ratio of hydrophilic:oil:lipophilic solvent is within the range of 60:20±17.5:20±17.5, more preferably 60:20±15; 20±15, still more preferably 60:20±12.5:20±12.5, yet more preferably 60:20±10:20±10, even more preferably 60:20±7.5:20±7.5, most preferably 60:20±5:20±5, and in particular 60:20±2.5:20±2.5.

In another preferred embodiment, the pharmaceutical dosage form contains a liquid core comprising the pharmacologically active agent according to general formula (I), a surfactant having a HLB value of at least 10 (hydrophilic surfactant), an oil and a surfactant having a HLB value below 10 (lipophilic surfactant), wherein the relative weight ratio of hydrophilic:oil; lipophilic solvent is within the range of 40:40±35:20±17.5, more preferably 40:40±30; 20±15, still more preferably 40:40±25:20±12.5, yet more preferably 40:40±20:20±10, even more preferably 40:40±15:20±7.5, most preferably 40:40±10:20±5, and in particular 40:40±5: 20±2.5.

Preferred embodiments $A^1$ to $A^{20}$ of the liquid core of the pharmaceutical dosage form according to the invention, i.e. of the liquid core that is encapsulated by an encapsulating material, are summarized in the following Table 1:

TABLE 1

| embodiment | $A^1$ | | $A^2$ | | $A^3$ | | $A^4$ | |
|---|---|---|---|---|---|---|---|---|
| ingredient | nature | cont. | nature | cont. | nature | cont. | nature | cont. |
| pharmacologically active agent according to general formula (I) | $W^1$ | 0.50 ± 0.49 | $W^1$ | 0.50 ± 0.49 | $W^1$ | 0.50 ± 0.49 | $W^1$ | 0.50 ± 0.49 |
| surfactant | $X^1$ | 30 ± 25 | $X^1$ | 45 ± 30 | $X^1$ | 60 ± 40 | $X^1$ | 60 ± 40 |
| oil | $Y^1$ | 40 ± 35 | $Y^1$ | 40 ± 30 | $Y^1$ | 15 ± 10 | $Y^1$ | 25 ± 20 |
| additional component | $Z^1$ | 30 ± 25 | $Z^1$ | 15 ± 10 | $Z^1$ | 25 ± 20 | $Z^1$ | 15 ± 10 |

| embodiment | $A^5$ | | $A^6$ | | $A^7$ | | $A^8$ | |
|---|---|---|---|---|---|---|---|---|
| ingredient | nature | cont. | nature | cont. | nature | cont. | nature | cont. |
| pharmacologically active agent according to general formula (I) | $W^1$ | 0.50 ± 0.49 | $W^1$ | 0.25 ± 0.24 | $W^2$ | 0.25 ± 0.24 | $W^2$ | 0.25 ± 0.24 |
| surfactant | $X^1$ | 60 ± 40 | $X^2$ | 40 ± 15 | $X^2$ | 60 ± 20 | $X^2$ | 60 ± 20 |
| oil | $Y^1$ | 20 ± 15 | $Y^2$ | 30 ± 15 | $Y^2$ | 10 ± 5 | $Y^2$ | 30 ± 15 |
| additional component | $Z^1$ | 20 ± 15 | $Z^2$ | 30 ± 15 | $Z^2$ | 30 ± 15 | $Z^2$ | 10 ± 5 |

| embodiment | $A^9$ | | $A^{10}$ | | $A^{11}$ | | $A^{12}$ | |
|---|---|---|---|---|---|---|---|---|
| ingredient | nature | cont. | nature | cont. | nature | cont. | nature | cont. |
| pharmacologically active agent according to general formula (I) | $W^2$ | 0.25 ± 0.24 | $W^2$ | 0.25 ± 0.24 | $W^2$ | 0.10 ± 0.09 | $W^2$ | 0.10 ± 0.09 |
| surfactant | $X^2$ | 50 ± 15 | $X^2$ | 60 ± 15 | $X^3$ | 40 ± 10 | $X^3$ | 50 ± 10 |
| oil | $Y^2$ | 25 ± 7.5 | $Y^2$ | 20 ± 7.5 | $Y^3$ | 30 ± 10 | $Y^3$ | 30 ± 10 |
| additional component | $Z^2$ | 25 ± 7.5 | $Z^2$ | 20 ± 7.5 | $Z^3$ | 30 ± 10 | $Z^3$ | 20 ± 7.5 |

| embodiment | $A^{13}$ | | $A^{14}$ | | $A^{15}$ | | $A^{16}$ | |
|---|---|---|---|---|---|---|---|---|
| ingredient | nature | cont. | nature | cont. | nature | cont. | nature | cont. |
| pharmacologically active agent according to general formula (I) | $W^2$ | 0.10 ± 0.09 | $W^3$ | 0.10 ± 0.09 | $W^3$ | 0.10 ± 0.05 | $W^3$ | 0.02 ± 0.01 |
| surfactant | $X^3$ | 60 ± 10 | $X^3$ | 70 ± 10 | $X^4$ | 50 ± 5 | $X^4$ | 50 ± 5 |
| oil | $Y^3$ | 20 ± 10 | $Y^3$ | 15 ± 5 | $Y^4$ | 25 ± 2.5 | $Y^4$ | 25 ± 2.5 |
| additional component | $Z^3$ | 20 ± 20 | $Z^3$ | 15 ± 5 | $Z^4$ | 25 ± 2.5 | $Z^4$ | 25 ± 2.5 |

| embodiment | $A^{17}$ | | $A^{18}$ | | $A^{19}$ | | $A^{20}$ | |
|---|---|---|---|---|---|---|---|---|
| ingredient | nature | cont. | nature | cont. | nature | cont. | nature | cont. |
| pharmacologically active agent according to general formula (I) | $W^3$ | 0.10 ± 0.05 | $W^3$ | 0.02 ± 0.01 | $W^3$ | 0.10 ± 0.05 | $W^3$ | 0.02 ± 0.01 |
| surfactant | $X^4$ | 60 ± 5 | $X^4$ | 60 ± 5 | $X^4$ | 60 ± 5 | $X^4$ | 60 ± 5 |
| oil | $Y^4$ | 25 ± 2.5 | $Y^4$ | 25 ± 2.5 | $Y^4$ | 20 ± 2.5 | $Y^4$ | 20 ± 2.5 |
| additional component | $Z^4$ | 15 ± 2.5 | $Z^4$ | 15 ± 2.5 | $Z^4$ | 20 ± 2.5 | $Z^4$ | 20 ± 2.5 | wherein
nature refers to the chemical nature of the ingredient;
cont. refers to the content of the ingredient in wt.-% based on the total weight of the core;
$W^1$ means pharmacologically active agent according to general formula (I) or a physiologically acceptable salt thereof;
$W^2$ means pharmacologically active agent according to general formula (I') or a physiologically acceptable salt thereof;
$W^3$ means (1r,4r)-6'-fluoro-N,N-dimethyl-4-phenyl-4',9'-dihydro-3'H-spiro[cyclohexane-1,1'-pyrano[3,4,b]indol]-4-amine, or (1r,4r)-6'-fluoro-N-methyl-4-phenyl-4',9'-dihydro-3'H-spiro[cyclohexane-1,1'-pyrano[3,4,b]indol]-4-amine, or a physiologically acceptable salt thereof;
$X^1$ means surfactant having a HLB value of at least 10;
$X^2$ means non-ionic surfactant having a HLB value of between 14 and 16;
$X^3$ means polyglycolyzed glyceride;
$X^4$ means polyoxyethylene fatty acid ester, the fatty acid preferably having from about 8 to about 18 carbon atoms;
$Y^1$ means mono-, di- or triester of the $C_6$ to $C_{18}$ fatty acids;
$Y^2$ means triglycerides of $C_6$ to $C_{12}$ fatty acids (medium-chain triglycerides);
$Y^3$ means propylene glycol fatty acid ester;
$Y^4$ caprylic/capric triglyceride mixture;
$Z^1$ means hydrophilic solvent
$Z^2$ means hydrophilic solvent selected from organic monoalcohol, dialcohol or trialcohol;
$Z^3$ means surfactant having a HLB value of below 10;
$Z^4$ means ethanol.

For example, according to the above table, embodiment $A^9$ relates to a pharmaceutical dosage according to the invention, which contains a pharmacologically active agent according to general formula (I') or a physiologically acceptable salt thereof in an amount of 0.25±0.24 wt.-%, a non-ionic surfactant having a HLB value of between 14 and 16 in an amount of 50±15 wt.-%, triglycerides of the $C_6$ to $C_{12}$ fatty acids in an amount of 25±7.5% and a hydrophilic solvent selected from organic monoalcohol, dialcohol or trialcohol in an amount of 25±7.5%, based on the total weight of the liquid core.

Preferably, the self-emulsifying formulation is a lipid formulation of type IIIA or type IIIB, according to the lipid formulation classification system (LFCS).

Preferably, the self emulsifying formulation gives emulsions with an average droplet size smaller than or equal to 10 micrometers, more preferably smaller than or equal to 1000 nanometers, most preferably smaller than or equal to 100 nanometers, when exposed to aqueous media.

In another preferred embodiment, the self-emulsifying formulation is a self-micro emulsifying drug delivery system (SMEDDS), i.e. when exposed to aqueous media, the formulation gives microemulsions with an average droplet size smaller than or equal to 50 nanometers, which contain the pharmacologically active agent according to general formula (I). In another preferred embodiment, the average droplet size is smaller than or equal to 10 nanometers In a preferred embodiment, the average droplet size is within the range of 50±70 nm, more preferably 50±60 nm, still more preferably 50±50 nm, yet more preferably 50±40 nm, even more preferably 50±30 nm, most preferably 50±20 nm, and in particular 50±10 nm.

In a preferred embodiment, the average droplet size is within the range of 75±70 nm, more preferably 75±60 nm, still more preferably 75±50 nm, yet more preferably 75±40 nm, even more preferably 75±30 nm, most preferably 75±20 nm, and in particular 75±10 nm.

In a preferred embodiment, the average droplet size is within the range of 100±70 nm, more preferably 100±60 nm, still more preferably 100±50 nm, yet more preferably 100±40 nm, even more preferably 100±30 nm, most preferably 100±20 nm, and in particular 100±10 nm.

In a preferred embodiment, the average droplet size is within the range of 125±70 nm, more preferably 125±60 nm, still more preferably 125±50 nm, yet more preferably 125±40 nm, even more preferably 125±30 nm, most preferably 125±20 nm, and in particular 125±10 nm. In a preferred embodiment, the average droplet size is within the range of 150±70 nm, more preferably 150±60 nm, still more preferably 150±50 nm, yet more preferably 150±40 nm, even more preferably 150±30 nm, most preferably 150±20 nm, and in particular 150±10 nm.

In a particular preferred embodiment,
the pharmaceutical dosage form contains a surfactant having a HLB value of at least 10 in an amount of at least 0.001 wt.-%, based on the total weight of the pharmaceutical dosage form; and/or
the pharmaceutical dosage form contains 0.01% to 95% of the pharmacologically active agent (A); and/or
the pharmaceutical dosage form has a weight within the range of from 0.1 mg to 2,000 mg; and/or
the pharmaceutical dosage form contains a polymer with a molecular weight within the range of from 1,000 g/mol to 15 million g/mol; and/or
the pharmaceutical dosage form is for oral administration; and/or
the pharmaceutical dosage form contains the pharmacologically active agent according to general formula (I) in a dose of from 10 µg to 50 µg or of from 300 µg to 500 µg; and/or
the pharmaceutical dosage form provides immediate release of the pharmacologically active agent according to general formula (I) in vitro in accordance with Ph. Eur.; and/or the pharmaceutical dosage form, wherein the active agent according to general formula (I) is molecularly dispersed; and/or
the pharmaceutical dosage form contains a self emulsifying formulation or a self-micro emulsifying formulation; and/or
the pharmaceutical dosage form comprises a liquid core encapsulated by a solid material, wherein the pharmacologically active agent according to general formula (I) is dispersed in the liquid core; and/or
the pharmaceutical dosage form, wherein said liquid core further contains an oil; and/or
the content of said oil is at least 5 wt.-%, based on the total weight of the liquid core; and/or
the pharmaceutical dosage form contains a coating, preferably a coating that is soluble in gastric juice; and/or
$t_{max}$ is within the range of from 0.5 to 16 h; and/or
the ratio $AUC_{0-t}$/dose is within the range of from 0.5 to 16.5 h/m³; and/or
ratio $C_{max}$/dose is within the range of from 0.06 to 1.69 m⁻³.

In a particular preferred embodiment,
the pharmaceutical dosage form contains a surfactant having a HLB value of at least 10 in an amount of at least 0.001 wt.-%, based on the total weight of the pharmaceutical dosage form; and/or
the pharmaceutical dosage form contains 0.01% to 95% of the pharmacologically active agent (A); and/or
the pharmaceutical dosage form has a weight within the range of from 0.1 mg to 2,000 mg; and/or
the pharmaceutical dosage form contains a polymer with a molecular weight within the range of from 1,000 g/mol to 15 million g/mol; and/or
the pharmaceutical dosage form is for oral administration; and/or
the pharmaceutical dosage form contains the pharmacologically active agent according to general formula (I) in a dose of from 10 µg to 50 µg or of from 300 µg to 500 µg; and/or
the pharmaceutical dosage form provides immediate release of the pharmacologically active agent according to general formula (I) in vitro in accordance with Ph. Eur.; and/or
$t_{max}$ is within the range of from 0.5 to 16 h; and/or
the ratio $AUC_{0-t}$/dose is within the range of from 0.5 to 16.5 h/m³; and/or
ratio $C_{max}$/dose is within the range of from 0.06 to 1.69 m⁻³.

In a preferred embodiment the pharmaceutical dosage form according to the invention, particularly when it contains the pharmacologically active agent according to general formula (I) in form of a solid solution, i.e. molecularly dispersed in a solid matrix, may further contain at least one matrix material. Preferably, said matrix material comprises a polymer selected from the group consisting of polyvinylpyrrolidone, vinylpyrrolidone-polyvinylacetate copolymers, cellulose derivatives, preferably cellulose esters or cellulose ethers, such as for example hydroxypropyl methylcellulose, hydroxypropyl methylcellulose acetate succinate, hydroxypropyl methylcellulose phthalate, ethylcellulose, polymethacrylates, polyethylene oxides, polyethylene glycols and any combinations thereof. Preferred examples of polyvinylpyrrolidone are commercialized as Kollidon® 90 and examples of vinylpyrrolidone-polyvinyl acetate copolymer are commercialized as Kollidon® VA64.

For the purpose of the specification, "molecularly dispersed in a solid matrix", e.g. in a polymer, means that a substantial portion of the overall content of the pharmacologically active agent according to general formula (I) is present in non-crystalline form, i.e. does not provide X-ray reflexes. Preferably, the content of non-crystalline pharmacologically active agent according to general formula (I) is at least 60 wt.-%, more preferably at least 65 wt.-%, still more preferably at least 70 wt.-%, yet more preferably at least 75 wt.-%, even more preferably at least 80 wt.-%, most preferably at least 85 wt.-%, and in particular at least 90 wt.-%, based on the total content of pharmacologically active agent corresponding to formula (I).

In a preferred embodiment the pharmaceutical dosage form according to the invention contains a polymer with a weight average molecular weight of preferably at least 50,000 g/mol, more preferably at least 100,000 g/mol, yet more preferably at least 250,000 g/mol, still more preferably at least 500,000 g/mol, most preferably at least 750,000 g/mol and in particularly at least 800,000 g/mol.

In another preferred embodiment the pharmaceutical dosage form according to the invention contains a polymer with a weight average molecular weight of preferably at least 5000 g/mol, more preferably at least 10,000 g/mol, yet more preferably at least 20,000 g/mol, still more preferably at least 30,000 g/mol, even more preferably at least 40,000 g/mol, most preferably at least 50,000 g/mol and in particular within the range of from 50,000 g/mol to 250,000 g/mol.

In a preferred embodiment, the pharmaceutical dosage form according to the invention contains the pharmacologically active agent according to general formula (I) in form of a solid solution, i.e. molecularly dispersed in a solid matrix, wherein the matrix comprises one or more polymers and wherein the content of the polymer(s) is within the range of 25±22.5 wt.-%, more preferably 25±20 wt.-%, still more preferably 25±17.5 wt.-%, yet more preferably 25±15 wt.-%, even more preferably 25±12.5 wt.-%, most preferably 25±10 wt.-% and in particular 25±7.5 wt.-%, based on the total weight of the pharmaceutical dosage form.

In another preferred embodiment, the pharmaceutical dosage form according to the invention contains the pharmacologically active agent according to general formula (I) in form of a solid solution, i.e. molecularly dispersed in a solid matrix, wherein the matrix comprises one or more polymers and wherein the content of the polymer(s) is within the range of 50±22.5 wt.-%, more preferably 50±20 wt.-%, still more preferably 50±17.5 wt.-%, yet more preferably 50±15 wt.-%, even more preferably 50±12.5 wt.-%, most preferably 50±10 wt.-% and in particular 50±7.5 wt.-%, based on the total weight of the pharmaceutical dosage form.

In still another preferred embodiment, the pharmaceutical dosage form according to the invention contains the pharmacologically active agent according to general formula (I) in form of a solid solution, i.e. molecularly dispersed in a solid matrix, wherein the matrix comprises one or more polymers and wherein the content of the polymer(s) is within the range of 75±22.5 wt.-%, more preferably 75±20 wt.-%, still more preferably 75±17.5 wt.-%, yet more preferably 75±15 wt.-%, even more preferably 75±12.5 wt.-%, most preferably 75±10 wt.-% and in particular 75±7.5 wt.-%, based on the total weight of the pharmaceutical dosage form.

In a preferred embodiment, the pharmaceutical dosage form according to the invention contains a polymer which comprises repeating units derived from vinylpyrrolidones. In another preferred embodiment the polymer comprises monomer units derived from vinyl acetates. Preferably, the polymer is a copolymer comprising repeating units derived from vinylpyrrolidones and repeating units derived from vinyl acetates, wherein the weight ratio of repeating units derived from vinylpyrrolidones:repeating units derived from vinyl acetates is preferably at most 10:1, more preferably at most 4.5:1, still more preferably at most 4:1, most preferably at most 2:1 and in particular at most 1.5:1.

In a preferred embodiment, the relative weight ratio of the polymer related to the pharmacologically active agent according to general formula (I) in the pharmaceutical dosage form according to the invention ranges from 1:1 to 70:1, more preferably from 2:1 to 50:1, still more preferably from 3:1 to 40:1, most preferably from 3.5:1 to 30:1 and in particular from 4:1 to 19:1. Preferably, the relative weight ratio of the polymer related to the pharmacologically active agent according to general formula (I) in the pharmaceutical dosage form according to the invention is at least 3:1 or at least 4:1, more preferably at least 5:1 or at least 6:1, still more preferably at least 7:1 or at least 8:1, yet more preferably at least 9:1 or at least 10:1, even more preferably at least 11:1 or at least 12:1, most preferably at least 13:1 or at least 14:1 and in particular at least 15:1 or at least 16:1.

In a preferred embodiment the relative weight ratio of the polymer, especially of polyvinylpyrrolidone, related to the pharmacologically active agent according to general formula (I) in the pharmaceutical dosage form according to the invention ranges from 1:1 to 70:1, more preferably from 2:1 to 45:1, still more preferably from 3:1 to 20:1, most preferably from 3.5:1 to 10:1 and in particular from 4:1 to 5:1.

In another preferred embodiment the relative weight ratio of the polymer, especially of vinylpyrrolidone-vinyl acetate copolymer, related to the pharmacologically active agent according to general formula (I) in the pharmaceutical dosage form according to the invention ranges from 1:1 to 70:1, more preferably from 2:1 to 55:1, still more preferably from 4:1 to 40:1, most preferably from 10:1 to 25:1 and in particular from 15:1 to 25:1.

In a preferred embodiment the pharmaceutical dosage form according to the invention, particularly when it contains the pharmacologically active agent according to general formula (I) in form of a solid solution, i.e. molecularly dispersed in a solid matrix, may further contain at least one surfactant selected from the group containing partial fatty acid esters of polyoxyethylene sorbitan (polyoxyethylene-sorbitan-fatty acid esters), preferably a fatty acid monoester of polyoxyethylene sorbitan, a fatty acid diester of polyoxyethylene sorbitan, or a fatty acid triester of polyoxyethylene sorbitan; sulfuric acid esters, or the alkali or earthalkali salts thereof; and poloxamers.

In a preferred embodiment the pharmaceutical dosage form according to the invention contains a surfactant with a weight average molecular weight of preferably at least 500 g/mol, more preferably at least 1,000 g/mol, yet more preferably at least 2,500 g/mol, still more preferably at least 5,000 g/mol, most preferably at least 7,000 g/mol and in particularly at least 8,000 g/mol.

In another preferred embodiment the pharmaceutical dosage form according to the invention contains a surfactant with a weight average molecular weight of preferably at least 100 g/mol, more preferably at least 250 g/mol, yet more preferably at least 500 g/mol, still more preferably at least 750 g/mol, most preferably at least 1,000 g/mol and in particularly at least 1,250 g/mol.

In another preferred embodiment the dosage form according to the invention contains a surfactant, preferably [polyoxyethylene(20)sorbitan monooleate] or polyoxyethylene-polyoxypropylene block co-polymer, in a content of preferably 0.5 wt-% to 80 wt-%, more preferably 1.5 wt-% to 60 wt-%, still more preferably 2.5 wt-% to 50 wt-%, yet more preferably 3.0 wt-% to 40 wt-%, most preferably 3.5 wt-% to 20 wt-%, and in particular 4 wt-% to 10 wt-%, based on the total weight of the pharmaceutical dosage form.

Preferred embodiment $A^1$ to $A^{20}$ of the pharmaceutical dosage form according to the invention are summarized in the following Table 2:

TABLE 2

| embodiment | $A^1$ | | $A^2$ | | $A^3$ | | $A^4$ | | $A^5$ | |
|---|---|---|---|---|---|---|---|---|---|---|
| ingredient | nature | ratio | nature | ratio | nature | Ratio | nature | ratio | nature | ratio |
| pharmacologically active agent according to general formula (I) | $X^1$ | 1 | $X^1$ | 1 | $X^2$ | 1 | $X^2$ | 1 | $X^3$ | 1 |
| polymer | $Y^1$ | 19 ± 17 | $Y^1$ | 19 ± 11 | $Y^2$ | 19 ± 7 | $Y^2$ | 19 ± 5 | $Y^3$ | 19 ± 3 |
| surfactant | $Z^1$ | 5 ± 4 | $Z^1$ | 5 ± 3 | $Z^2$ | 5 ± 2 | $Z^2$ | 5 ± 1 | $Z^3$ | 5 ± 0.5 |

| embodiment | $A^6$ | | $A^7$ | | $A^8$ | | $A^9$ | | $A^{10}$ | |
|---|---|---|---|---|---|---|---|---|---|---|
| ingredient | nature | ratio | nature | ratio | nature | Ratio | nature | ratio | nature | ratio |
| pharmacologically active agent according to general formula (I) | $X^1$ | 2 | $X^1$ | 2 | $X^2$ | 2 | $X^2$ | 2 | $X^3$ | 2 |
| polymer | $Y^1$ | 38 ± 34 | $Y^1$ | 38 ± 22 | $Y^2$ | 38 ± 14 | $Y^2$ | 38 ± 10 | $Y^3$ | 38 ± 06 |
| surfactant | $Z^1$ | 5 ± 4 | $Z^1$ | 5 ± 3 | $Z^2$ | 5 ± 2 | $Z^2$ | 5 ± 1 | $Z^3$ | 5 ± 0.5 |

| embodiment | $A^{11}$ | | $A^{12}$ | | $A^{13}$ | | $A^{14}$ | | $A^{15}$ | |
|---|---|---|---|---|---|---|---|---|---|---|
| ingredient | nature | ratio | nature | ratio | nature | ratio | nature | ratio | nature | ratio |
| pharmacologically active agent according to general formula (I) | $X^1$ | 3 | $X^1$ | 3 | $X^2$ | 3 | $X^2$ | 3 | $X^3$ | 3 |
| polymer | $Y^1$ | 57 ± 51 | $Y^1$ | 57 ± 33 | $Y^2$ | 57 ± 21 | $Y^2$ | 57 ± 15 | $Y^3$ | 57 ± 9 |
| surfactant | $Z^1$ | 5 ± 4 | $Z^1$ | 5 ± 3 | $Z^2$ | 5 ± 2 | $Z^2$ | 5 ± 1 | $Z^3$ | 5 ± 0.5 |

| embodiment | $A^{16}$ | | $A^{17}$ | | $A^{18}$ | | $A^{19}$ | | $A^{20}$ | |
|---|---|---|---|---|---|---|---|---|---|---|
| ingredient | nature | ratio | nature | ratio | nature | ratio | nature | ratio | nature | ratio |
| pharmacologically active agent according to general formula (I) | $X^1$ | 4 | $X^1$ | 4 | $X^2$ | 4 | $X^2$ | 4 | $X^3$ | 4 |
| polymer | $Y^1$ | 76 ± 68 | $Y^1$ | 76 ± 44 | $Y^2$ | 76 ± 28 | $Y^2$ | 76 ± 20 | $Y^3$ | 76 ± 12 |
| surfactant | $Z^1$ | 5 ± 4 | $Z^1$ | 5 ± 3 | $Z^2$ | 5 ± 2 | $Z^2$ | 5 ± 1 | $Z^3$ | 5 ± 0.5 | wherein
nature refers to the chemical nature of the ingredient;
ratio refers to the relative weight proportion of the ingredient with respect to the other two ingredients;
$X^1$ means the pharmacologically active agent according to general formula (I) or a physiologically acceptable salt thereof;
$X^2$ means the pharmacologically active agent according to general formula (I') or a physiologically acceptable salt thereof;
$X^3$ means (1r,4r)-6'-fluoro-N,N-dimethyl-4-phenyl-4',9'-dihydro-3H-spirocyclohexane-1,1-pyrano[3,4,b]indol-4-amine, or (1r,4r)-6'-fluoro-N-methyl-4-phenyl-4',9'-dihydro-3'H-spiro-[cyclohexane-1,1'-pyrano3,4,b]indol-4-amine, or a physiologically acceptable salt thereof;
$Y^1$ means a polymer selected from the group consisting of polyvinylpyrrolidone, vinylpyrrolidone-vinylacetate copolymers, cellulose derivatives, preferably cellulose esters or cellulose ethers, polymethacrylates, polyethylene oxides, polyethylene glycols and any combinations thereof;
$Y^2$ means vinylpyrrolidone-vinylacetate copolymer;
$Y^3$ means vinylpyrrolidone-vinylacetate copolymers having a weight average molecular weight within the range of from 40,000 to 250,000 g/mol;
$Z^1$ means a nonionic surfactan with a HLB value of 10-20;
$Z^2$ means a surfactant selected from the group of partial fatty acid esters of polyoxyethylene sorbitan;
$Z^3$ means a surfactant according to general forumla (II-b).

For example, according to the above foregoing Table 2, embodiment $A^9$ relates to a pharmacologically active agent according to general formula (I') or a physiologically acceptable salt thereof, a vinylpyrrolidone-polyvinylacetate copolymer and a surfactant selected from the group of polysorbitanes, wherein the weight ratio is 2:38:5.

In a preferred embodiment, the content of the surfactant is within the range of 1.00±0.70 wt.-%, more preferably 1.00±0.60 wt.-%, still more preferably 1.00±0.50 wt.-%, yet more preferably 1.00±0.40 wt.-%, even more preferably 1.00±0.30 wt.-%, most preferably 1.00±0.20 wt.-%, and in particular 1.00±0.10 wt.-%

Preferred embodiments $A^1$ to $A^{29}$ of the pharmaceutical dosage form according to the invention are summarized in the following Table 3:

TABLE 3

| embodiment | $A^1$ | | $A^2$ | | $A^3$ | | $A^4$ | |
|---|---|---|---|---|---|---|---|---|
| Ingredient | nature | content | nature | content | nature | content | nature | content |
| pharmacologically active agent according to general formula (I) | $Y^1$ | 0.04 ± 0.035 | $Y^1$ | 0.04 ± 0.025 | $Y^2$ | 0.04 ± 0.02 | $Y^3$ | 0.04 ± 0.01 |
| Surfactant | $Z^1$ | 2.75 ± 2.50 | $Z^2$ | 1.00 ± 0.50 | $Z^3$ | 1.00 ± 0.20 | $Z^4$ | 1.00 ± 0.10 |

TABLE 3-continued

| embodiment | $A^5$ | | $A^6$ | | $A^7$ | | $A^8$ | |
|---|---|---|---|---|---|---|---|---|
| Ingredient | nature | content | nature | content | nature | content | nature | content |
| pharmacologically active agent according to general formula (I) | $Y^1$ | 0.32 ± 0.30 | $Y^1$ | 0.32 ± 0.25 | $Y^2$ | 0.32 ± 0.20 | $Y^3$ | 0.32 ± 0.10 |
| Surfactant | $Z^1$ | 2.75 ± 2.50 | $Z^2$ | 1.00 ± 0.50 | $Z^3$ | 1.00 ± 0.20 | $Z^4$ | 1.00 ± 0.10 |

| embodiment | $A^9$ | | $A^{10}$ | | $A^{11}$ | | $A^{12}$ | |
|---|---|---|---|---|---|---|---|---|
| Ingredient | nature | content | nature | content | nature | content | nature | content |
| pharmacologically active agent according to general formula (I) | $Y^1$ | 0.50 ± 0.45 | $Y^1$ | 0.50 ± 0.30 | $Y^2$ | 0.50 ± 0.20 | $Y^3$ | 0.50 ± 0.10 |
| surfactant | $Z^1$ | 2.75 ± 2.50 | $Z^2$ | 1.00 ± 0.50 | $Z^3$ | 1.00 ± 0.20 | $Z^4$ | 1.00 ± 0.10 |

| embodiment | $A^{13}$ | | $A^{14}$ | | $A^{15}$ | | $A^{16}$ | |
|---|---|---|---|---|---|---|---|---|
| ingredient | nature | content | nature | content | nature | content | nature | content |
| pharmacologically active agent according to general formula (I) | $Y^1$ | 0.60 ± 0.55 | $Y^1$ | 0.60 ± 0.40 | $Y^2$ | 0.60 ± 0.20 | $Y^3$ | 0.60 ± 0.10 |
| surfactant | $Z^1$ | 2.75 ± 2.50 | $Z^2$ | 1.00 ± 0.50 | $Z^3$ | 1.00 ± 0.20 | $Z^4$ | 1.00 ± 0.10 | wherein
nature refers to the chemical nature of the ingredient;
content refers to the content of the ingredient in wt.-% based on the total weight of the dosage form;
$Y^1$ means pharmacologically active agent according to general formula (I) or a physiologically acceptable salt thereof;
$Y^2$ means pharmacologically active agent according to general formula (I') or a physiologically acceptable salt thereof;
$Y^3$ means (1r,4r)-6'-fluoro-N,N-dimethyl-4-phenyl-4',9'-dihydro-3'H-spiro[cyclohexane-1,1'-pyrano[3,4,b]indol]-4-amine, or (1r,4r)-6'-fluoro-N-methyl-4-phenyl-4',9'-dihydro-3'H-spiro-[cyclohexane-1,1'-pyrano[3,4,b]indol]-4-amine, or a physiologically acceptable salt thereof;
$Z^1$ means surfactant having a HLB value of at least 10;
$Z^2$ means anionic surfactant having a HLB value of at least 30;
$Z^3$ means anionic surfactant selected from the group consisting of sodium lauryl sulfate (sodium dodecyl sulfate, e.g. Texapon ® K12), sodium cetyl sulfate (e.g. Lanette E ®), sodium cetylstearyl sulfate, sodium stearyl sulfate, sodium dioctylsulfosuccinate (docusate sodium),di-[2-ethylhexyl]-succinate; and the corresponding potassium or calcium salts thereof;
$Z^4$ means sodium lauryl sulfate.

For example, according to the foregoing Table 3, embodiment $A^9$ relates to a pharmaceutical dosage according to the invention, which contains the pharmacologically active agent according to general formula (I) in an amount of 0.50±0.45 wt.-% and a surfactant having a HLB value of at least 10 in an amount of 2.75±2.50 wt.-%, based on the total weight of the dosage form.

In a particular preferred embodiment,
the pharmaceutical dosage form contains a surfactant having a HLB value of at least 10 in an amount of at least 0.001 wt.-%, based on the total weight of the pharmaceutical dosage form; and/or
the pharmaceutical dosage form is for oral administration; and/or
the pharmaceutical dosage form contains 0.01% to 95% of the pharmacologically active agent (A); and/or
the pharmaceutical dosage form has a weight within the range of from 0.1 mg to 2,000 mg; and/or
the pharmaceutical dosage form contains a polymer with a molecular weight within the range of from 1,000 g/mol to 15 million g/mol; and/or
the pharmaceutical dosage form is a tablet; and/or
the pharmaceutical dosage form is prepared by means of wet granulation or direct tabletting; and/or
the pharmaceutical dosage form contains the pharmacologically active agent according to general formula (I) in a dose of from 10 µg to 50 µg or of from 300 µg to 500 µg; and/or
the pharmaceutical dosage form provides immediate release of the pharmacologically active agent according to general formula (I) in vitro in accordance with Ph. Eur.; and/or $t_{max}$ is within the range of from 0.5 to 16 h; and/or
the ratio $AUC_{0-t}$/dose is within the range of from 0.5 to 16.5 h/m³; and/or
ratio $C_{max}$/dose is within the range of from 0.06 to 1.69 m$^{-3}$.

In a preferred embodiment, the pharmaceutical dosage form according to the invention is a tablet, chewable tablet, chewing gum, coated tablet or powder, optionally filled into a capsule, but particularly preferably a tablet.

In another preferred embodiment, the pharmaceutical dosage form according to the invention is present in multi-particulate form, preferably in form of a micro-tablet, microcapsule, granulate, pellet or active-substance crystal, particularly preferably in form of a micro-tablet, granulate or pellet, optionally filled into a capsule or compressed to form a tablet.

In some especially preferred embodiments, the pharmaceutical dosage form according to the invention is a tablet. The tablet can be of any desired size. In some preferred embodiments, the tablet has a diameter of 6±3 mm, more preferably of 6±2.5 mm, even more preferably of 6±2 mm, still more preferably of 6±1.5 mm, most preferably of 6±1 mm, and in particular of 6±0.5 mm.

The pharmaceutical dosage form according to the invention may contain pharmaceutical excipients including conventional antiadherents, binders, disintegrants, fillers, diluents, glidants, lubricants and preservatives, known to a person skilled in the art.

One suitable antiadherent that may be contained in the pharmaceutical dosage form is magnesium stearate. In a preferred embodiment, the content of the antiadherent is within the range of from 0.001 to 5.0 wt.-%, for example 0.01 to 5 wt.-%, 0.1 to 5 wt.-%, 0.1 to 3 wt.-%, 0.1 to 2 wt.-%, or even 0.5 to 1.5 wt.-%.

In a preferred embodiment, the pharmaceutical dosage form according to the invention further contains a binder. Suitable binders include but are not limited to gelatin, cellulose, modified cellulose such as microcrystalline cellulose, methyl cellulose, polyvinyl pyrrolidone, starch, sucrose and polyethylene glycol; especially preferred are polyvinyl pyrrolidone and/or microcrystalline cellulose. In a preferred embodiment, the content of antiadherent is within the range of from 0.001 to 30 wt.-%, more preferably 0.1 to 25 wt.-%. In some embodiments, the dosage form comprises 1 to 20 wt.-%, 5 to 20 wt.-%, or 10 to 20 wt.-% of binder(s).

In a preferred embodiment, the pharmaceutical dosage form according to the invention further contains a filler and/or diluent, preferably selected from the group consisting of but are not limited to cellulose, calcium diphosphate, lactose, sucrose, glucose, mannitol, sorbitol, and calcium carbonate; especially preferred are micro-crystalline cellulose and lactose. In a preferred embodiment, the content of filler and/or diluent is within the range of from 0.001 to 90 wt.-%, 0.01 to 85 wt.-%, more preferably 0.1 to 80 wt.-%, most preferably 10 to 75 wt.-%.

In a preferred embodiment, the pharmaceutical dosage form according to the invention further contains a lubricant such as magnesium stearate, stearic acid and stearin. In a preferred embodiment, the content of the lubricant is within the range of from 0.001 to 5 wt.-%, e.g., from 0.1 to 3 wt. %.

In a preferred embodiment, the pharmaceutical dosage form according to the invention further contains a disintegrant such as cross-linked sodium carboxymethyl cellulose (croscarmellose sodium), cross-linked polyvinyl pyrrolidone and sodium starch glycolate. In a preferred embodiment, the content of the disintegrant is within the range of from 0.001 to 5 wt.-%, e.g., from 0.1 to 3 wt. %.

The pharmaceutical dosage form may further contain at least one preservative. Suitable preservatives include but are not limited to antioxidants, such as vitamin A, vitamin E, vitamin C, retinyl palmitate and selenium; cysteine, methionine, citric acid, sodium citrate, methyl paraben and propyl paraben.

In a preferred embodiment, the pharmaceutical dosage form further contains a coating, in particular a polymer-based coating, more in particular a polyvinyl alcohol-based coating such as the ones commercially available under the trade name "Opadry".

In some preferred embodiments, the pharmaceutical dosage form is a tablet which comprises the pharmacologically active agent according to the general formula (I) (e.g., in an amount from 0.6±0.4 wt.-%, 0.6±0.3 wt.-%, 0.6±0.2 wt.-%, 0.6±0.1 wt.-%, 0.04±0.03 wt.-%, 0.04±0.02 wt.-%, or 0.04±0.01 wt.-%), one or more antiadherents (e.g., magnesium stearate) in an amount from 0.001 to 5.0 wt.-% (e.g., 0.01 to 5 wt.-%, 0.1 to 5 wt.-%, 0.1 to 3 wt.-%, 0.1 to 2 wt.-%, or even 0.5 to 1.5 wt.-%), one a more binders (e.g., polyvinyl pyrrolidone and/or microcrystalline cellulose) in an amount from 0.001 to 30 wt.-% (e.g., from 0.1 to 25 wt.-%, 1 to 20 wt.-%, 5 to 20 wt.-%, or 10 to 20 wt.-%), and one or more fillers or diluents (e.g., microcrystalline cellulose and/or lactose) in an amount from 0.001 to 90 wt.-% (e.g., 0.01 to 85 wt.-%, more preferably 0.1 to 80 wt.-%, most preferably 10 to 75 wt.-%). In some embodiments, the tablet also comprises one or more lubricants (e.g., magnesium stearate, stearic acid and/or stearin) in an amount from 0.001 to 5 wt.-% (e.g., from 0.1 to 3 wt. %) and/or one or more disintegrants (e.g., croscarmellose sodium, cross-linked polyvinyl pyrrolidone and/ or sodium starch glycolate) in an amount from 0.001 to 5 wt.-% (e.g., from 0.1 to 3 wt. %).

Preferably, the coating protects the pharmaceutical dosage form from moisture, but dissolves rapidly in gastric juice. More preferably, the coated dosage form has a disintegration time of less than 5 minutes in gastric juice, more preferably of at most 4.5 minutes, still more preferably at most 4 minutes, yet more preferably at most 3.5 minutes, even more preferably at most 3 minutes, most preferably at most 2.5 minutes and in particular at most 2 minutes.

For the manufacture of the pharmaceutical dosage forms according to the invention, the various solid auxiliary substances and the pharmacologically active agent according to general formula (I) are preferably homogenized, processed by means of wet, dry or fusion granulation to form granulates, and compressed to form tablets. Alternatively, they are manufactured by direct tabletting of the auxiliary substances and the pharmacologically active agent according to general formula (I).

In a preferred embodiment, the pharmaceutical dosage form is prepared by means of wet granulation from a granulating fluid containing the pharmacologically active agent according to general formula (I), in particular from an aqueous granulating fluid containing said pharmacologically active agent and the surfactant. Preferably, the resulting granulating fluid is then top-sprayed or bottom-sprayed onto a solid formulation containing at least one auxiliary substance to yield compressible granules, which may optionally be mixed with further auxiliary substances before being compressed to tablets.

A further aspect of the invention relates to the pharmaceutical dosage form according to the invention as described above for use in the treatment of pain.

A further aspect of the invention relates to a method of treating pain comprising the twice daily, once daily, or less frequently, preferably oral administration of the pharmaceutical dosage form according to the invention to a subject in need thereof.

Preferably, the pain is selected from acute, visceral, neuropathic or chronic pain.

In another particular preferred embodiment,
the pharmaceutical dosage form contains 0.01% to 95% of the pharmacologically active agent (A); and/or
the pharmaceutical dosage form has a weight within the range of from 0.1 mg to 2,000 mg; and/or
the pharmaceutical dosage form is adapted for oral administration; and/or
the pharmaceutical dosage form contains the pharmacologically active agent according to general formula (I) in a dose of from 10 µg to 50 µg or from 25 µg to 80 µg; and/or
the pharmacologically active agent according to general formula (I) is contained in the dosage form in an amount that is sub-therapeutic with regard to a single administration of the dosage form; and/or
the pharmacologically active agent according to general formula (I) is contained in the dosage form in a quantity that is sub-therapeutic with regard to acute pain treatment; and/or
the pharmacologically active agent according to general formula (I) is contained in the dosage form in a quantity such that initial dose titration is not required; and/or
the pharmacologically active agent according to general formula (I) is contained in the dosage form in a quantity such that number of adverse events that occur during administration of the dosage form is decreased compared to a dosage form comprising a pure µ-opioid receptor agonist, such as morphine in a therapeutically equally effective amount; and/or $t_{max}$ is within the range of from 2 to 10 h, preferably from 2 to 6 h; and/or the ratio $AUC_{0-t}$/dose is within the range of from 0.5 to 16.5 h/m³, preferably from 6 to 12 h/m³; and/or ratio $C_{max}$/dose is within the range of from 0.06 to 1.69 m⁻³, preferably within the range of from 0.3 to 1.3 m⁻³; and/or the highest plasma concentration of the pharmacological agent reached after once daily administration of the pharmaceutical dosage form for at least 5 consecutive days is within the range from 10 to 120 µg/m³, preferably 20 to 80 µg/m³.

A further aspect of the invention relates to a method of treating neuropathic pain, preferably chronic neuropathic pain comprising the administration of a pharmacologically effective amount of the pharmacologically active agent according to general formula (I) or a physiologically acceptable salt thereof; preferably the once daily, preferably oral administration of the pharmaceutical dosage form according to the invention; to a subject in need thereof.

Preferably, the pain is chronic neuropathic pain or acute neuropathic pain, peripheral neuropathic pain or central neuropathic pain, mononeuropathic pain or polyneuropathic pain. When the neuropathic pain is chronic, it may be chronic peripheral neuropathic pain or chronic central neuropathic pain, in a preferred embodiment chronic peripheral mononeuropathic pain or chronic central mononeuropathic pain, in another preferred embodiment chronic peripheral polyneuropathic pain or chronic central polyneuropathic pain. When the neuropathic pain is acute, it may be acute peripheral neuropathic pain or acute central neuropathic pain, in a preferred embodiment acute peripheral mononeuropathic pain or acute central mononeuropathic pain, in another preferred embodiment acute peripheral polyneuropathic pain or acute central polyneuropathic pain.

Preferably, the pain is chronic neuropathic pain. For the purpose of the specification, neuropathic pain is pain that originates from nerve damage or nerve malfunction. It becomes classified as chronic neuropathic pain when it is present for more than 3 months.

In another particular preferred embodiment of the invention, the pharmaceutical dosage form contains 0.01% to 95% of the pharmacologically active agent (A); and/or the pharmaceutical dosage form has a weight within the range of from 0.1 mg to 2,000 mg; and/or the pharmaceutical dosage form is adapted for oral administration; and/or the pharmaceutical dosage form contains the pharmacologically active agent according to general formula (I) in a dose of from 200 µg to 800 µg or from 300 µg to 500 µg; and/or the pharmacologically active agent according to general formula (I) is contained in the dosage form in an amount that is sub-therapeutic with regard to a single administration of the dosage form; and/or the pharmacologically active agent according to general formula (I) is contained in the dosage form in a quantity such that initial dose titration is not required; and/or the pharmacologically active agent according to general formula (I) is contained in the dosage form in a quantity such that number of adverse events that occur during administration of the dosage form is decreased compared to a dosage form comprising a pure µ-opioid receptor agonist, such as morphine in a therapeutically equally effective amount; and/or $t_{max}$ is within the range of from 2 to 10 h, preferably from 5 to 7 h; and/or the ratio $AUC_{0-t}$/dose is within the range of from 0.5 to 16.5 h/m³, preferably from 6 to 12 h/m³; and/or ratio $C_{max}$/dose is within the range of from 0.06 to 1.69 m⁻³, preferably within the range of from 0.30 to 1.30 m⁻³.

A further aspect of the invention relates to a method of treating nociceptive pain, preferably acute or chronic nociceptive pain, comprising the once daily, preferably oral administration of the pharmaceutical dosage form according to the invention to a subject in need thereof.

BRIEF DESCRIPTION OF THE DRAWINGS

The invention will be described in further detail hereinafter with reference to the accompanying drawings, in which:

FIG. 10 shows the mean maximum plasma concentration of the compound according to formula (I'b) measured on the last day of a 5-day once daily dosing period in comparison to the plasma concentration measured 8 to 10 days later at the end of a wash-out phase.

EXAMPLES

Figure 1:
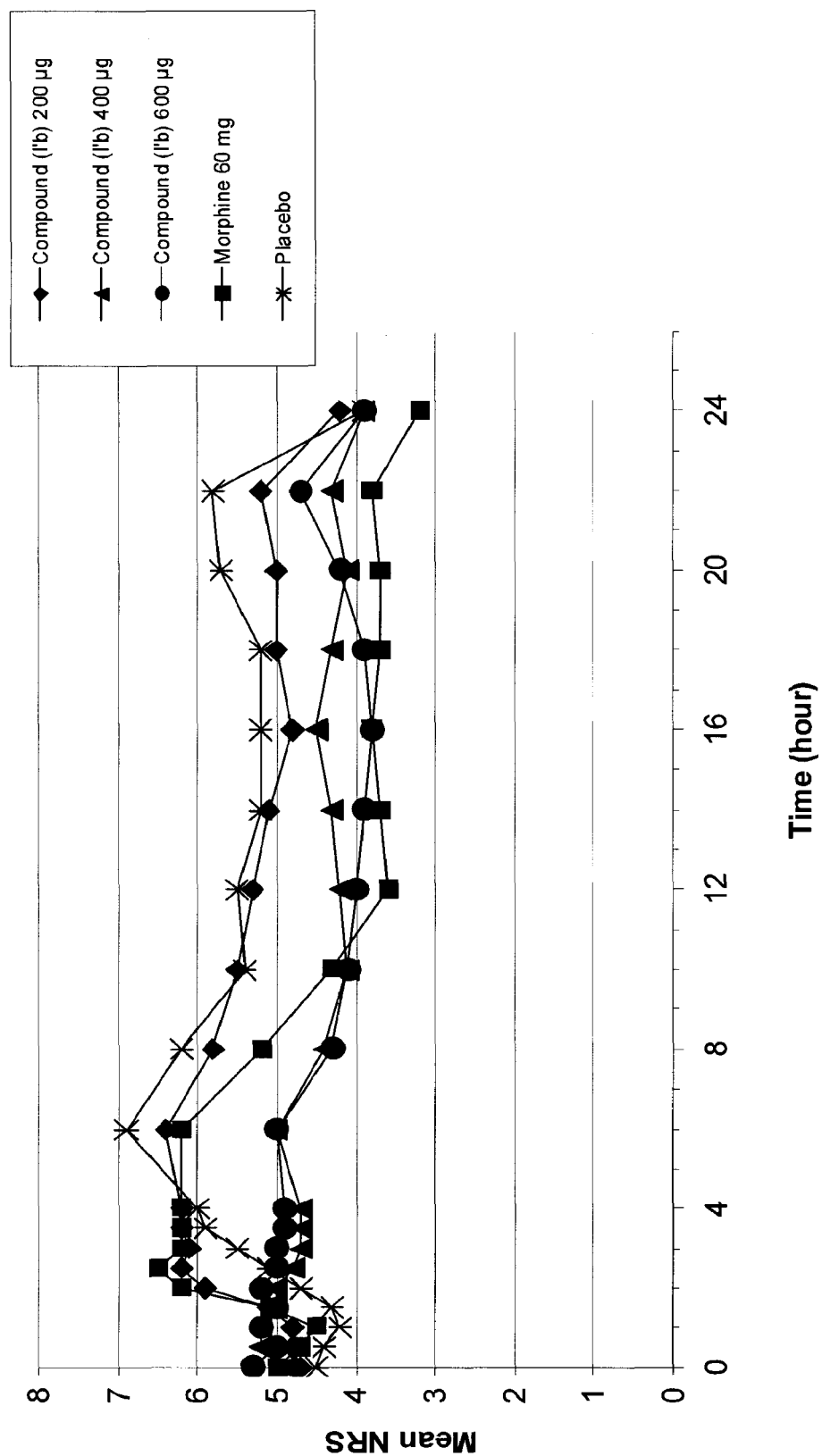
FIG. 1 shows the averaged numerical rating scale (NRS) values measured over a 24 hour period after administration of different single doses of the compound according to formula (I'b) (200, 400, 600 µg) compared to slow release morphine and placebo in patients with acute post-operative pain following orthopedic surgery (bunionectomy).

The following examples further illustrate the invention but are not to be construed as limiting its scope.

Example 1a

In order to find a suitable combination of oil, surfactant and hydrophilic solvent, the saturation concentration of the pharmacologically active agent according to formula (I'b) was first determined in a variety of oils as follows:

A saturated solution of said pharmacologically active agent was made by suspending an appropriate amount in 5 g of the respective medium. After removing any trace of undissolved material by filtration through a sintered glass filter (0.45 μm and 0.22 μm), the remaining solution was concentrated under vacuum. The vacuum was maintained until all obvious traces of solvent had been removed, and the flask was then stored over night under high vacuum. The weight of the remaining compound was determined and the saturation concentration of (I'b) in the respective oil was calculated.

The results are displayed in the following Table 4:

TABLE 4

| Oil | Amount of Solvent [g] | Amount of (I'b) (before filtration) [g/5 g] | Saturation concentration [mg/g] |
| --- | --- | --- | --- |
| Oleic acid | 5 | 0.26061 | 30.0060 |
| Caprylic acid | 5 | 0.13559 | 26.0920 |
| Ethyl oleate | 5 | 0.01373 | 0.8043 |
| Soybean oil | 5 | 0.01587 | 0.8739 |
| Peanut oil | 5 | 0.01400 | 0.9898 |
| Miglyol 812 | 5 | 0.01075 | 0.9400 |
| Captex 355 | 5 | 0.01221 | 0.9615 |
| Labrafac WL 1349 | 5 | 0.01207 | 0.9349 |
| Capryol 90 | 5 | 0.02153 | 3.3547 |
| Capric acid | 5 | 0.12076 | 23.5590 |
| Maisine 35-1 50° C. | 5 | 0.04688 | 3.7418 |
| Labrafil M 1944 CS | 5 | 0.04197 | 4.8707 |
| Labrafil M 2125 CS | 5 | 0.04855 | 5.0369 |
| Myristic Acid | 5 | 0.01934 | 3.7878 |

The saturation concentration of compound (I'b) was determined accordingly in a variety of surfactants at 50° C. (filter: 0.45 μm). The results are displayed in the following Table 5:

TABLE 5

| Surfactant | Amount of Solvent [g] | Amount of (I'b) (before filtration) [g/5 g] | Saturation concentration [mg/g] |
| --- | --- | --- | --- |
| TPGS (PEG-Vit.E succhinate) | 5 | 0.04921 | 8.0491 |
| Gelucire 44/14 | 5 | 0.04265 | 3.7280 |
| Gelucire 50/13 65° C. | 5 | 0.05182 | 10.0160 |
| Cremophor EL | 5 | 0.04342 | 9.0519 |
| Cremophor RH40 | 5 | 0.04884 | 9.6462 |
| Tween 20 | 5 | 0.03895 | 7.4428 |
| Tween 60 | 5 | 0.04151 | 8.7866 |
| Tween 80 | 5 | 0.02177 | 4.2641 |
| Labrasol | 5 | 0.05707 | 10.7540 |
| Glycerol monooleate (Peceol) | 5 | 0.01517 | 2.9428 |
| Solutol HS15 | 5 | 0.04921 | 10.1650 |

As suitable oils oleic acid, caprylic acid and capric acid were identified (solubility >20 mg/g solvent), whereas labrasol, solutol HS 15 and gelucire 50/13 were identified as suitable surfactants (solubility >10 mg/g solvent).

The saturation concentration of compound (I'b) was determined accordingly in ethanol and selected propylene glycols. The results are displayed in the following Table 6:

TABLE 6

| Solvent | Amount of Solvent [g] | Amount of (I'b) (before filtration) [g/5 g] | Saturation concentration [mg/g] |
| --- | --- | --- | --- |
| Ethanol | 5 | 0.01498 | 0.1458 |
| Propylenglycol | 5 | 0.01858 | 0.1084 |
| PEG 400 | 5 | 0.03061 | 4.7791 |
| PEG 1500 | 5 | 0.02565 | 8.2633 |
| PEG 4000 | 5 | 0.03992 | 7.6528 |

Example 1b

According to example 1a, the saturation concentration of compound (I'b) was determined in two-component formulations of one oil (oleic acid, caprylic acid or capric acid) and one surfactant (labrasol, tween 60, solutol HS 15 and gelucire 50/13). Since these two-component formulations are solid at room-temperature, these solubility studies were conducted at 50° C. If these two-component formulations contain sufficient amounts of (I'b), they are also liquid at room temperature. A saturated solution of the two-component formulation is a liquid, as well.

TABLE 7

| Formulation | Ratio surfactant/oil | Amount of (I'b) (before filtration) [g/5 g] | Saturation concentration [mg/g] |
| --- | --- | --- | --- |
| Labrasol/Caprylic Acid | 5:95 | 0.10308 | 17.24 |
| Labrasol/Caprylic Acid | 10:90 | 0.09126 | 16.87 |
| Labrasol/Caprylic Acid | 20:80 | 0.09185 | 15.89 |
| Labrasol/Caprylic Acid | 40:60 | 0.07167 | 12.3 |
| Labrasol/Oleic Acid | 5:95 | 0.14580 | 28.76 |
| Labrasol/Oleic Acid | 10:90 | 0.12596 | 22.45 |
| Labrasol/Oleic Acid | 20:80 | 0.01154 | 22.85 |
| Labrasol/Oleic Acid | 40:60 | 0.09044 | 19.57 |
| Tween60/Caprylic Acid | 5:95 | 0.09633 | 18.85 |
| Tween60/Caprylic Acid | 10:90 | 0.09832 | 18.98 |
| Tween60/Caprylic Acid | 20:80 | 0.02941 | 7.36 |
| Tween60/Caprylic Acid | 40:60 | 0.03410 | 6.59 |
| Solutol HS15/Caprylic Acid | 5:95 | 0.09329 | 18.32 |
| Solutol HS15/Caprylic Acid | 10:90 | 0.08622 | 16.14 |
| Solutol HS15/Caprylic Acid | 20:80 | 0.07366 | 15.13 |
| Solutol HS15/Caprylic Acid | 40:60 | 0.05841 | 12.39 |
| Solutol HS15/Capryol 90 | 5:95 | 0.05355 | 3.008 |
| Solutol HS15/Capryol 90 | 10:90 | 0.04418 | 3.138 |
| Solutol HS15/Capryol 90 | 20:80 | 0.05118 | 3.650 |
| Solutol HS15/Capryol 90 | 40:60 | 0.04335 | 4.561 |
| Gelucire44/14/Capryol 90 | 5:95 | 0.04786 | 3.060 |
| Gelucire44/14/Capryol 90 | 10:90 | 0.04515 | 3.312 |
| Gelucire44/14/Capryol 90 | 20:80 | 0.04667 | 4.047 |
| Gelucire44/14/Capryol 90* | 40:60 | 0.06647 | 6.068 |

Accordingly, the saturation concentration of (I'b) in the following three-component formulation was determined:

| | |
|---|---|
| Solutol ® HS 15 | 60% (w/w) |
| Miglyol 812 | 20% (w/w) |
| Ethanol (abs.) | 20% (w/w) |

The saturation concentration of (I'b) in said formulation was determined to be 1.3 mg/g.

Example 2

The phase behavior of the oil/surfactant mixtures according to example 1 b was determined in presence of an aqueous medium.

For that purpose, 20 g of the respective two-component mixture was made by mixing the respective amounts of oil and surfactant. 0.5 g of the mixture was then added to 250 g of water or 250 g of gastric juice, respectively.

The formation of an emulsion in the aqueous medium was observed, described visually (qualitative extent of turbidity) and measured quantitatively by means of a conventional turbidity photometer.

TABLE 8

| | ratio surfactant/oil | Appearance of the formulation (clear, turbid, colour, . . . ) | | | | |
|---|---|---|---|---|---|---|
| | [wt.-%/ wt.-%] | in absence of aqueous media | [TE/F] | in 250 mL $H_2O$ | [TE/F] | in 250 mL gastric juice |
| Labrasol/Caprylic Acid | | clear | 25 | emulsion | 32 | oil droplets, turbid |
| Labrasol/Caprylic Acid | 10:90 | clear | 23 | emulsion | 2.9 | oil droplets, clear |
| Labrasol/Caprylic Acid | 20:80 | clear | 21 | emulsion | 11 | oil droplets, clear |
| Labrasol/Caprylic Acid | 40:60 | clear | 82 | emulsion | 15 | oil droplets, clear |
| Labrasol/Oleic Acid | 5:95 | clear | 36 | emulsion, clear | 12.2 | oil droplets, turbid |
| Labrasol/Oleic Acid | 10:90 | clear | 46 | emulsion, clear | 19 | oil droplets, turbid |
| Labrasol/Oleic Acid | 20:80 | clear | 41 | emulsion, clear | 33 | oil droplets, turbid |
| Labrasol/Oleic Acid | 40:60 | clear | 124 | emulsion, clear | 71 | oil droplets, turbid |
| Labrasol/Capric Acid | 5:95 | solid, white, crystalline | 28 | n.d. | 9 | Solid, partly fibrous matter |
| Labrasol/Capric Acid | 10:90 | solid, white, crystalline | 34 | n.d. | 7.7 | Solid, partly fibrous matter |
| Labrasol/Capric Acid | 20:80 | solid, white, crystalline | 27 | n.d. | 10.3 | Solid, partly fibrous matter |
| Labrasol/Capric Acid | 40:60 | solid, white, clear | 60 | n.d. | 11 | Solid, partly fibrous matter |
| Tween60/Caprylic Acid | 5:95 | clear, slightly yellowish | 33 | turbid, drop formation | 19 | small droplets, turbid |
| Tween60/Caprylic Acid | 10:90 | clear, slightly yellowish | 34 | turbid, drop formation | 36 | droplets, turbid |
| Tween60/Caprylic Acid | 20:80 | clear, yellowish | 69 | opaque | 80 | flocculate |
| Tween60/Caprylic Acid | 40:60 | clear, deep yellow | 162 | turbid, no drop formation visible | 155 | Turbid, no drop formation visible |
| Tween60/Oleic Acid | 5:95 | clear, slightly yellowish | 404 | milky, upper layer, flocculate | 350 | flocculate |
| Tween60/Oleic Acid | 10:90 | clear, slightly yellowish | >680 | milky, upper layer, flocculate | 776 | flocculate |
| Tween60/Oleic Acid | 20:80 | clear, slightly yellowish | 614 | milky, upper layer, flocculate | 876 | flocculate |
| Tween60/Oleic Acid | 40:60 | clear, slightly yellowish | 910 | milky, upper layer, flocculate | 520 | flocculate |
| Tween60/Capric Acid | 5:95 | solid, yellowish-white, crystalline | 34 | solid, fibrous | 17 | solid upper layer, flocculate |
| Tween60/Capric Acid | 10:90 | Solid, yellowish-white, crystalline | 35 | containing solid matter | 25 | solid upper layer, flocculate |

TABLE 8-continued

| | ratio surfactant/oil [wt.-%/wt.-%] | Appearance of the formulation (clear, turbid, colour, . . . ) | | | | |
|---|---|---|---|---|---|---|
| | | in absence of aqueous media | [TE/F] | in 250 mL H$_2$O | [TE/F] | in 250 mL gastric juice |
| Tween60/Capric Acid | 20:80 | solid, yellowish-white, crystalline | 72 | deeply turbid | 85 | solid upper layer, flocculate |
| Tween60/Capric Acid | 40:60 | Solid, yellowish-white | 646 | turbid, no drop formation visible | 279 | solid upper layer, flocculate |
| Solutol HS15/ Caprylic Acid | 5:95 | clear | 27 | floating oily drops | 8.1 | oil droplets |
| Solutol HS15/ Caprylic Acid | 10:90 | clear | 12.4 | floating oily drops | 11 | oil droplets |
| Solutol HS15/ Caprylic Acid | 20:80 | clear | 28 | emulsoid, slightly turbid | 18 | emulsoid, small droplets |
| Solutol HS15/ Caprylic Acid | 40:60 | clear | 54 | opaque, (micro-emulsion) | 98 | opaque (micro-emulsion) |
| Solutol HS15/ Oleic Acid | 5:95 | clear | 55 | drop formation, opaque | 30 | large droplets |
| Solutol HS15/ Oleic Acid | 10:90 | clear | 36 | flocculate, turbid | 60 | flocculate |
| Solutol HS15/ Oleic Acid | 20:80 | clear | 704 | flocculate, turbid | 450 | flocculate |
| Solutol HS15/ Oleic Acid | 40:60 | 2 phases: clear, turbid | 1267 | flocculate, turbid | 777 | flocculate, deeply turbid |
| Solutol HS15/ Capric Acid | 5:95 | solid, white, clear | 8.5 | needles | 11.4 | solid upper layer |
| Solutol HS15/ Capric Acid | 10:90 | solid, white, clear | 21 | needles | 8.8 | solid upper layer |
| Solutol HS15/ Capric Acid | 20:80 | solid, white, clear | 23 | needles | 13.7 | solid upper layer |
| Solutol HS15/ Capric Acid | 40:60 | 2 phases: liquid, clear; crystalline, white | 144 | turbid, upper layer | 93 | small crystal needles |
| Gelucire 50/13/ Caprylic Acid | 5:95 | Clear | 26 | transparent, small drops | 26 | emulsoid, turbid |
| Gelucire 50/13/ Caprylic Acid | 10:90 | Clear; crystalline, white, precipitate | 12.1 | transparent, small drops | 24 | emulsoid, turbid |
| Gelucire 50/13/ Caprylic Acid | 20:80 | Clear; crystalline, white, precipitate | 19 | transparent, drops of variable size | 65 | emulsoid, turbid |
| Gelucire 50/13/ Caprylic Acid | 40:60 | Clear; crystalline, white, precipitate | 90 | turbid, flocculate | 87 | opaque, particles |
| Gelucire 50/13/ Oleic Acid | 5:95 | Clear; crystalline, white, precipitate | 335 | upper layer, white foam | 450 | emulgator seems not to be soluble |
| Gelucire 50/13/ Oleic Acid | 10:90 | Clear; crystalline, white, precipitate | 465 | upper layer, white foam | 1031 | emulgator seems not to be soluble |
| Gelucire 50/13/ Oleic Acid | 20:80 | Clear; crystalline, white, precipitate, highly viscous | 1050 | upper layer, white foam | 260 | emulgator seems not to be soluble |
| Gelucire 50/13/ Oleic Acid | 40:60 | Clear; crystalline, white precipitate, highly viscous | 403 | upper layer, white foam | 263 | emulgator seems not to be soluble |
| Gelucire 50/13/ Capric Acid | 5:95 | solid, white, crystalline | 7.3 | Solid upper layer | 32 | n.d. |
| Gelucire 50/13/ Capric Acid | 10:90 | solid, white, crystalline | 21 | Solid upper layer | 57 | n.d. |
| Gelucire 50/13/ Capric Acid | 20:80 | solid, white, crystalline | 62 | Solid upper layer | 58 | n.d. |
| Gelucire 50/13/ Capric Acid | 40:60 | solid, white, crystalline | 520 | Solid upper layer | 433 | n.d. |

The extent of turbidity is an indication for the size of the droplets of an emulsion. Micro- or nanoemulsions appear clear to the naked eye and do not show turbidity, since the size of the droplets is too small for refracting visible light.

As a result, two-component mixtures of labrasol and caprylic acid, labrasol and oleic acid, tween 60 and caprylic acid, as well as solutol HS 15 and caprylic acid formed clear solutions in absence of any aqueous media. All of them formed emulsions in water and gastric juice. Tween 60/caprylic acid (40:60) and solutol HS 15/caprylic acid (40:60) showed the best phase behavior in aqueous media forming clear microemulsions without visible drop formation in water and in gastric juice.

Emulsions which gave promising results in the previous study were then subjected to particle size analysis (using a laser-based particle size analyzer type Zetasizer NanoZS, Malvern Instruments) with a particle size measurement range of 0.02 to 2,000 μm. Particle size was calculated from the volume size distribution.

TABLES 9-17

| Measurement | Peak 1 diameter [nm] | Peak 1 occurence [%] | Peak 2 diameter [nm] | Peak 2 occurence [%] | Peak 3 diameter [nm] | Peak 3 occurence [%] |
|---|---|---|---|---|---|---|
| Labrasol-oleic acid 40:60 in 250 g H$_2$O | | | | | | |
| 1 | 326.2 | 3.1 | 100.2 | 96.9 | 0 | 0 |
| 2 | 169.8 | 100 | 0 | 0 | 0 | 0 |
| 3 | 2956 | 0.1 | 152 | 99.9 | 0 | 0 |
| Labrasol-oleic acid 40:60 in 250 g gastric juice | | | | | | |
| 1 | 242.6 | 100 | 0 | 0 | 0 | 0 |
| 2 | 243.8 | 100 | 0 | 0 | 0 | 0 |
| 3 | 265.8 | 100 | 0 | 0 | 0 | 0 |
| Labrasol-oleic acid 5:95 in 250 g H$_2$O | | | | | | |
| 1 | 0 | 0 | 0 | 0 | 0 | 0 |
| 2 | 6.411 | 100 | 0 | 0 | 0 | 0 |
| 3 | 19.35 | 100 | 0 | 0 | 0 | 0 |
| Solutol-caprylic acid 40:60 in 250 g H$_2$O | | | | | | |
| 1 | 289.7 | 8.4 | 2938 | 0 | 94.4 | 91.6 |
| 2 | 154.9 | 96 | 772.2 | 3.2 | 0 | 0 |
| 3 | 175.7 | 97.6 | 982.8 | 2.4 | 0 | 0 |
| Solutol-caprylic acid 40:60 in 250 g gastric juice | | | | | | |
| 1 | 142 | 100 | 0 | 0 | 0 | 0 |
| 2 | 107.8 | 100 | 0 | 0 | 0 | 0 |
| 3 | 206 | 100 | 0 | 0 | 0 | 0 |
| Tween 60-caprylic acid 40:60 in 250 g H$_2$O | | | | | | |
| 1 | 62.06 | 100 | 0 | 0 | 0 | 0 |
| 2 | 79.3 | 100 | 0 | 0 | 0 | 0 |
| 3 | 53.32 | 100 | 0 | 0 | 0 | 0 |
| Tween 60-caprylic acid 40:60 in 250 g gastric juice | | | | | | |
| 1 | 52.24 | 99.6 | 204.5 | 0.4 | 0 | 0 |
| 2 | 49.07 | 99.2 | 146.6 | 0.8 | 0 | 0 |
| 3 | 46.15 | 98.4 | 117.3 | 1.6 | 546.6 | 0 |
| Tween 60-caprylic acid 20:80 in 250 g H$_2$O | | | | | | |
| 1 | 151.3 | 0.1 | 28.37 | 99.9 | 0 | 0 |
| 2 | 198.2 | 100 | 0 | 0 | 0 | 0 |
| 3 | 186.3 | 100 | 0 | 0 | 0 | 0 |
| Tween 60-caprylic acid 20:80 in 250 g gastric juice | | | | | | |
| 1 | 1218 | 0.2 | 59.09 | 99.8 | 0 | 0 |
| 2 | 442.2 | 100 | 0 | 0 | 0 | 0 |
| 3 | 892.6 | 0.3 | 65.8 | 99.7 | 0 | 0 |

Example 3

The stability of compound (I'b) in a variety of oils and surfactants was determined under stress (elevated temperature):

For this study, 50 mg of said compound was dissolved in 50 g of the respective medium and objected to elevated temperatures for 6 weeks. The same study was conducted using 500 mg of compound (I'b). After this period, the corresponding demethylated derivative (I'a) and/or the corresponding cis/trans-isomerized derivatives were identified as main degradation products.

The results show that the lowest degradation occurred in Solutol, Capryol and Gelucire. In general, the degradation was lower in the higher dosed samples.

TABLE 18

|  | 50 mg in 50 g Oleic acid | 50 mg in 50 g Caprylic acid | 50 mg in 50 g Capric acid | 50 mg in 50 g Gelucire | 41 mg in 41 g Tween 60 | 50 mg in 50 g Labrasol | 50 mg in 50 g Solutol | 50 mg in 50 g Capryol |
|---|---|---|---|---|---|---|---|---|
| Content of (I'b) | | | | | | | | |
| in the assay | 170.01% | 100.39% | 186.13% | 100.46% | 93.05% | 99.55% | 100.11% | 99.70% |
| after 2 weeks at 25° C. | 175.72% | 101.01% | 101.68% | 101.29% | 96.73% | 99.94% | 102.72% | 101.06% |
| 2 weeks at 40° C.F. | 176.43% | 100.68% | 101.10% | 101.09% | 92.43% | 95.69% | 102.13% | 100.67% |
| 4 weeks at 25° C. | 156.64% | 101.43% | 97.62% | 102.62% | 92.22% | 98.33% | 100.25% | 99.46% |
| 4 weeks at 40° C.F. | 143.56% | 101.11% | 91.46% | 102.56% | 89.09% | 91.93% | 100.08% | 99.07% |
| 6 weeks at 25° C. | 156.85% | 101.69% | 120.87% | 100.75% | 91.45% | 97.63% | 100.45% | 99.86% |
| 6 weeks at 40° C.F. | 141.66% | 100.93% | 94.19% | 100.41% | 86.93% | 89.87% | 99.69% | 99.36% |
| Purity | | | | | | | | |
| in the assay | 93.85% | 95.26% | 94.93% | 99.34% | 96.63% | 98.36% | 98.83% | 97.44% |
| compound (I'a) | 4.93% | — | — | 0.66% | — | 1.64% | — | 0.22% |
| cis isomer of (I'a) | — | — | — | — | — | — | — | — |
| Amount other | 1.23% | 4.74% | 5.07% | — | 3.37% | — | 1.08% | 2.34% |
| cis isomer of (I'b) | — | — | — | — | — | — | 0.09% | — |
| after 2 weeks at 25° C. | 93.22% | 95.19% | 94.71% | 99.60% | 97.01% | 98.22% | 98.92% | 97.51% |
| compound (I'a) | 5.75% | — | — | — | — | 1.71% | — | 0.13% |
| cis isomer of (I'a) | — | — | — | — | — | — | — | — |
| amount other | 1.03% | 4.81% | 3.95% | 0.40% | 2.99% | 0.06% | 1.01% | 2.36% |
| cis isomer of (I'b) | — | — | 1.35% | — | — | — | 0.07% | — |
| after 2 weeks at 40° C.F. | 88.45% | 95.12% | 94.57% | 99.30% | 94.62% | 95.11% | 98.81% | 97.37% |
| compound (I'a) | 9.69% | — | — | — | — | 4.29% | — | 0.22% |
| cis isomer of (I'a) | — | — | — | — | — | — | — | — |
| amount other | 1.77% | 4.88% | 4.13% | 0.70% | 5.38% | 0.61% | 1.03% | 2.41% |
| cis isomer of (I'b) | 0.10% | — | 1.30% | — | — | — | 0.17% | — |
| after 4 weeks at 25° C. | 89.17% | 94.51% | 98.96% | 99.36% | 96.96% | 97.07% | 99.12% | 99.29% |
| compound (I'a) | 10.72% | 0.05% | — | 0.59% | — | 2.82% | 0.04% | 0.20% |
| cis isomer of (I'a) | — | — | 1.04% | 0.03% | — | 0.03% | — | — |
| amount other | 0.12% | 5.45% | — | 0.03% | 3.03% | 0.08% | 0.84% | 0.51% |
| cis isomer of (I'b) | — | — | — | — | — | — | — | — |
| after 4 weeks at 40° C.F. | 84.27% | 97.30% | 99.13% | 98.96% | 94.12% | 92.02% | 98.90% | 98.10% |
| compound (I'a) | 15.48% | 0.08% | — | 0.98% | — | 7.87% | 0.16% | 0.34% |
| cis isomer of (I'a) | — | — | — | 0.03% | — | 0.02% | — | — |
| amount other | 0.25% | 2.62% | 0.87% | 0.03% | 5.87% | 0.09% | 0.95% | 1.57% |
| cis isomer of (I'b) | — | — | — | — | — | — | — | — |
| after 6 weeks at 25° C. | 88.41% | 96.57% | 93.36% | 99.44% | 96.89% | 96.71% | 99.15% | 98.54% |
| compound (I'a) | 11.52% | 0.32% | 5.63% | 0.53% | 2.78% | 3.24% | 0.08% | 0.16% |
| cis isomer of (I'a) | — | — | 0.95% | 0.03% | — | — | — | — |
| amount other | 0.07% | 3.11% | 0.06% | — | 0.33% | 0.04% | 0.77% | 1.29% |
| cis isomer of (I'b) | — | — | — | — | — | — | — | — |
| after 6 weeks at 40° C.F. | 84.99% | 96.06% | 92.74% | 98.81% | 93.60% | 90.17% | 98.82% | 98.22% |
| compound (I'a) | 14.45% | 0.5% | 6.34% | 1.17% | 5.99% | 9.78% | 0.20% | 0.37% |
| cis isomer of (I'a) | — | — | 0.92% | 0.02% | — | — | — | — |
| amount other | 0.57% | 3.43% | — | — | 0.41% | 0.05% | 0.98% | 1.42% |
| cis isomer of (I'b) | — | — | — | — | — | — | — | — |

|  | 500 mg in 50 g Oleic acid | 500 mg in 50 g Caprylic acid | 500 mg in 50 g Capric acid | 400 mg in 50 g Gelucire | 400 mg in 50 g Labrasol | 400 mg in 50 g Solutol | 350 mg in 50 g Tween 60 | 100 mg in 50 g Capryol |
|---|---|---|---|---|---|---|---|---|
| Content of (I'b) | | | | | | | | |
| in the assay | 102.13% | 100.13% | 101.20% | 100.93% | 98.55% | 98.18% | 99.41% | 99.46% |
| after 2 weeks at 25° C. | 102.61% | 100.12% | 102.50% | 102.67% | 97.36% | 100.21% | 94.96% | 100.97% |
| 2 weeks at 40° C.F. | 100.48% | 100.22% | 102.19% | 101.53% | 97.09% | 89.65% | 105.18% | 101.57% |
| 4 weeks at 25° C. | 96.79% | 99.46% | 98.89% | 100.90% | 97.63% | 98.41% | 99.26% | 100.10% |
| 4 weeks at 40° C.F. | 95.70% | 99.62% | 100.76% | 100.54% | 95.60% | 80.83% | 89.08% | 99.63% |
| 6 weeks at 25° C. | 93.24% | 99.77% | 112.08% | 99.77% | 97.41% | 99.16% | 78.26% | 99.62% |
| 6 weeks at 40° C.F. | 94.39% | 99.02% | 100.26% | 99.16% | 96.52% | 88.83% | 84.54% | 99.22% |
| Purity | | | | | | | | |
| in the assay | 94.62% | 99.35% | 98.94% | 99.91% | 98.78% | 99.82% | 99.02% | 98.00% |
| compound (I'a) | 4.62% | — | — | 0.09% | 1.22% | — | 0.81% | 0.29% |
| cis isomer of (I'a) | — | — | — | — | — | — | — | — |
| Amount other | 0.76% | 0.65% | 1.06% | — | — | 0.11% | — | 1.71% |
| cis isomer of (I'b) | — | — | — | — | — | 0.07% | 0.17% | — |
| after 2 weeks at 25° C. | 94.40% | 99.61% | 100.00% | 99.91% | 98.77% | 99.81% | 98.98% | 98.79% |
| compound (I'a) | 4.96% | — | — | 0.09% | 1.23% | — | 0.73% | 0.13% |
| cis isomer of (I'a) | — | — | — | — | — | — | — | — |
| amount other | 0.64% | 0.39% | — | — | — | 0.12% | 0.30% | 1.08% |
| cis isomer of (I'b) | — | — | — | — | — | 0.06% | — | — |
| after 2 weeks at 40° C.F. | 91.26% | 99.61% | 99.92% | 99.90% | 97.75% | 99.74% | 98.09% | 98.67% |

TABLE 18-continued

| | | | | | | | | |
|---|---|---|---|---|---|---|---|---|
| compound (I'a) | 7.09% | — | — | 0.10% | 2.25% | 0.06% | 1.26% | 0.20% |
| cis isomer of (I'a) | — | — | — | — | — | — | — | — |
| amount other | 1.57% | 0.39% | — | — | — | 0.09% | 0.65% | 1.13% |
| cis isomer of (I'b) | 0.08% | — | 0.08% | — | — | 0.11% | — | — |
| after 4 weeks at 25° C. | 93.55% | 99.75% | 99.91% | 99.86% | 98.10% | 99.78% | 98,82% | 98.99% |
| compound (I'a) | 6.33% | — | — | 0.11% | 1.87% | 0.05% | 0.04% | 0.15% |
| cis isomer of (I'a) | — | — | — | — | — | 0.06% | — | — |
| amount other | 0.12% | 0.25% | 0.09% | 0.03% | 0.03% | 0.12% | 0.84% | 0.85% |
| cis isomer of (I'b) | — | — | — | — | — | — | — | — |
| after 4 weeks at 40° C. | 91.70% | 99.71% | 99.90% | 99.79% | 96.79% | 99.64% | 97.99% | 98.79% |
| compound (I'a) | 8.30% | 0.03% | 0.02% | 0.17% | 3.17% | 0.10% | 1.76% | 0.29% |
| cis isomer of (I'a) | — | — | — | — | — | 0.15% | 0.25% | — |
| amount other | 0.10% | 0.25% | 0.08% | 0.03% | 0.04% | 0.11% | — | 0.93% |
| cis isomer of (I'b) | — | — | — | — | — | — | — | — |
| after 6 weeks at 25° C. | 93.26% | 99.72% | 99.85% | 99.89% | 97.92% | 99.71% | 98.79% | 99.05% |
| compound (I'a) | 6.65% | 0.02% | 0.05% | 0.08% | 2.06% | 0.11% | 1.08% | 0.16% |
| cis isomer of (I'a) | — | 0.21% | 0.05% | 0.03% | 0.02% | 0.13% | 0.13% | — |
| amount other | 0.10% | 0.05% | 0.04% | — | — | 0.06% | — | 0.79% |
| cis isomer of (I'b) | — | — | — | — | — | — | — | — |
| after 6 weeks at 40° C.F. | 92.03% | 99.70% | 99.01% | 99.82% | 96.52% | 99.80% | 97.99% | 98.91% |
| compound (I'a) | 7.88% | 0.04% | 0.31% | 0.16% | 3.46% | 9.78% | 1.85% | 0.27% |
| cis isomer of (I'a) | — | 0.21% | 0.61% | 0.02% | 0.02% | — | 0.16% | — |
| amount other | 0.09% | 0.04% | 0.08% | — | — | 0.05% | — | 0.83% |
| cis isomer of (I'b) | — | — | — | — | — | — | — | — |

Example 4

The ability and performance of Solutol HS 15/Capryol mixtures and Gelucire 44/14/Capryol mixtures to (micro) emulsify, each containing compound (I'b), was determined next.

For that purpose, 20 g of the respective formulation was made by mixing the respective amounts of oil, surfactant and compound (I'b). 0.5 g of the resulting formulation were then exposed to 250 mL of water or 250 mL of gastric juice and the resulting emulsion formation was measured qualitatively (visually) and quantitatively by means of a conventional turbidity photometer.

TABLE 19

| | ratio | Solubility of (I'b) | Appearance of the formulation (clear, turbid, colour, . . . ) | | | | |
|---|---|---|---|---|---|---|---|
| | surfactant/oil [wt.-%/wt.-%] | (in surfactant/oil) [mg/g] | in absence of aqueous media | [TE/F] | in 250 mL $H_2O$ | [TE/F] | in 250 mL gastric juice |
| Solutol HS/ Capryol | 5:95 | 3.01 | clear | 169 | emulsion, transparent, slightly turbid | 313 | milky, opaque, uniformly turbid |
| Solutol HS/ Capryol | 10:90 | 3.14 | clear | 430 | emulsion, than previous sample | 411 | milky, opaque more turbid |
| Solutol HS/ Capryol | 20:80 | 3.65 | clear | 180 | turbid, floating particles, vanish during shaking | 238 | transparent, slightly opaque, microemulsion |
| Solutol HS/ Capryol | 40:60 | 4.56 | clear | 66 | turbid, floating particles, vanish during shaking | 56 | transparent, microemulsion, more turbid than previous sample |
| Gelucire 44/14/ Capryol | 5:95 | 3.06 | clear | 101 | clear, emulsion | 136 | Turbid with particles, rather suspension |
| Gelucire 44/14/ Capryol | 10:90 | 3.31 | transparent with streaks | 85 | slightly opaque, emulsion | 290 | Turbid with particles, rather suspension |
| Gelucire 44/14/ Capryol | 20:80 | 4.05 | white, solid, flocculate, turbid | 136 | opaque, emulsoid | 338 | Turbid with particles, rather suspension |
| Gelucire 44/14/ Capryol | 40:60 | 6.07 | Solid and liquid parts at 25° C., saturated solution of (I'b) is liquid | 31 | milky, emulsoid | 50 | Turbid with particles, rather suspension |

The formation of a microemulsion was observed in those samples which contained Solutol HS 15 and Capryol in ratios of 20:80 and 40:60, respectively.

Example 5

A formulation was formulated from the following composition:

| | |
|---|---|
| Solutol ® HS 15 | 60% (w/w) |
| Miglyol 812 | 20% (w/w) |
| Ethanol (abs.) | 20% (w/w) |

By adding the appropriate amount of compound (I'a) to the said formulation, solutions of three different concentrations were prepared:

TABLE 20

| | C-1 (placebo) | I-1 | I-2 | I-3 |
|---|---|---|---|---|
| Formulation | 1 mL | 1 mL | 1 mL | 1 mL |
| Compound (1'a) | — | 0.1 mg | 1.0 mg | 10 mg |
| Concentration of (1'a) in the formulation | | 0.01 wt.-% | 0.1 wt.-% | 1.0 wt.-% |

1 mL of each of these mixtures was diluted with 20 mL of water. Additional water was sequentially added to the respective solution in 5 mL portions and the turbidity process was analyzed by means of a conventional turbidity spectrometer:

TABLE 21

| | C-1 (placebo) | I-1 | I-2 | I-3 |
|---|---|---|---|---|
| +0 mL $H_2O$ | 58 | 54 | 57 | 55 |
| +5 mL $H_2O$ | 51 | 47 | 51 | 47 |
| +10 mL $H_2O$ | 44 | 42 | 49 | 41 |
| +15 mL $H_2O$ | 40 | 36 | 42 | 37 |
| +20 mL $H_2O$ | 36 | 29 | 36 | 32 |
| +25 mL $H_2O$ | 32 | 27 | 32 | 29 |
| +30 mL $H_2O$ | 30 | 25 | 28 | 26 |
| +35 mL $H_2O$ | 28 | 23 | 27 | 24 |
| +40 mL $H_2O$ | 25 | 21 | 27 | 24 |
| +45 mL $H_2O$ | 24 | 20 | 22 | 21 |
| +50 mL $H_2O$ | 22 | 19 | 21 | 19 |
| +55 mL $H_2O$ | 21 | 17.7 | 20 | 18 |
| +60 mL $H_2O$ | 20 | 16.7 | 20 | 17.3 |
| +65 mL $H_2O$ | 19 | 16.2 | 20 | 16.4 |
| +70 mL $H_2O$ | 18.1 | 15.4 | 16.9 | 15.5 |
| +75 mL $H_2O$ | 17.5 | 14.5 | 15.8 | 15.2 |
| +80 mL $H_2O$ | 16.2 | 14.2 | 15.4 | 14 |
| +85 mL $H_2O$ | 15.9 | 13.4 | 16 | 14 |
| +90 mL $H_2O$ | 15.4 | 13.7 | 16 | 13.5 |
| +95 mL $H_2O$ | 14.8 | 13.1 | 14.1 | 12.2 |
| +100 mL $H_2O$ | 14.3 | 12.3 | 13.5 | 11.9 |
| +105 mL $H_2O$ | 13.6 | 12.5 | 14.4 | 11.1 |
| +110 mL $H_2O$ | 13.2 | 11.6 | 12.6 | 11.4 |
| +115 mL $H_2O$ | 12.9 | 11.8 | 12.6 | 10.2 |
| +120 mL $H_2O$ | 12.5 | 11.2 | 12.1 | 10.2 |
| +125 mL $H_2O$ | 12 | 10.8 | 15.5 | 9.7 |
| +130 mL $H_2O$ | 11.9 | 10.4 | 12.7 | 9.3 |
| +135 mL $H_2O$ | 11.6 | 10.5 | 11.3 | 9.3 |
| +140 mL $H_2O$ | 11.5 | 9.6 | 10.8 | 9.2 |
| +145 mL $H_2O$ | 11.1 | 10.4 | 10.7 | 8.7 |
| +150 mL $H_2O$ | 10.8 | 10 | 13 | 9 |
| +155 mL $H_2O$ | 10.7 | 9.2 | 10.1 | 8.3 |
| +160 mL $H_2O$ | 10.3 | 9.2 | 9.8 | 8.2 |
| +165 mL $H_2O$ | 10 | 10 | 9.3 | 8.1 |
| +170 mL $H_2O$ | 9.8 | 8.6 | 9.3 | 7.9 |
| +175 mL $H_2O$ | 9.5 | 8.6 | 9.2 | 7.7 |
| +180 mL $H_2O$ | 9.2 | 8.2 | 10.5 | 7.8 |
| +185 mL $H_2O$ | 9 | 8 | 8.5 | 8.2 |
| +190 mL $H_2O$ | 9.4 | 8.3 | 8.4 | 7 |
| +195 mL $H_2O$ | 9.4 | 7.6 | 8.2 | 7 |
| +200 mL $H_2O$ | 9 | 7.8 | 8.5 | 6.9 |
| +205 mL $H_2O$ | 8.4 | 7.8 | 7.8 | 6.5 |
| +210 mL $H_2O$ | 8.4 | 7.3 | 7.7 | 6.5 |
| +215 mL $H_2O$ | 8.1 | 7 | 7.5 | 6.3 |
| +220 mL $H_2O$ | 8.8 | 7 | 7.8 | 6 |
| +225 mL $H_2O$ | 8.3 | 6.9 | 7.6 | 6 |
| +230 mL $H_2O$ | 8.1 | 6.7 | 7.2 | 5.9 |

The experimental findings show that the turbidity profile of formulation according to the comparative sample C-1 is comparable to the turbidity profiles of the formulations according to the inventive examples I-1, I-2 and I-3, meaning that the presence of compound (I'a) hardly has an influence on the ability to (micro)emulsify of these formulations

Example 6

The following SMEDDS (self-microemulsifying drug delivery system) formulation was prepared:

| | |
|---|---|
| Solutol ® HS 15 | 60% (w/w) |
| Miglyol 812 | 20% (w/w) |
| Ethanol (abs.) | 20% (w/w) |

From the SMEDDS formulation and appropriate amounts of compound (1'b), solutions were prepared, that were then put into hard gelatin capsules. According to the following composition capsules of two dosages were prepared (50 µg and 400 µg):

TABLE 22

| Ingredient | % (m/m), Dosage 50 μg | Amount per capsule [mg] | % (m/m), Dosage 400 μg | Amount per capsule [mg] |
|---|---|---|---|---|
| Formulation SMEDDS | 99.986 | 349.95 | 99.886 | 349.6 |
| Compound (I'b) | 0.014 | 0.05 | 0.114 | 0.4 |
| Total | 100.0 | 350.0 | 100.0 | 350.0 |

Two batches of about 1000 of these hard gelatin capsules were manufactured for each of both dosages and packaged in brown glasses with screw caps. The SMEDDS formulations were put into empty hard gelatin capsules (size 0) and subjected to stability testing studies at 25° C./60% relative humidity (RH) (long-term storage conditions) and 40° C./75% RH (accelerated storage conditions). Samples were charged in stability chambers with humidity and temperature control. They were withdrawn at specified intervals for analysis over a period of 6 months. Drug content of the capsules was analyzed using a previously developed and validated stability-indicating HPLC method. Besides the chemical stability of the drug, the dissolution profile of the dosage form was also studied.

The testing results revealed that all measured parameters (unity of the drug content, the drug's purity, release of the drug) met the demands of the ICH and FDA guidelines. The determined content of the decomposition product 6'-fluoro-4-phenyl-4',9'-dihydro-3'H-spiro[cyclohex-3-ene-1,1-pyrano[3,4-b]indole] after storage at 40° C. and 75% rh was for dosage 50 μg 0.16% after 1 month, 0.25% after 3 months and 0.42% after 6 months; and for dosage 400 μg 0.09% after 1 month, 0.12% after 3 months and 0.25% after 6 months.

Example 7

Clinical studies were conducted to determine the analgesic efficacy and tolerability of single doses of the compound according to formula (I'b) (200 μg, 400 μg and 600 μg; hemicitrate oral solution of compound (I'b) in Macrogol 400; all dosages relative to the free base of the drug) compared to that of morphine (60 mg, controlled-released form) and placebo in patients with acute post-operative pain following orthopedic surgery (bunionectomy).

For this purpose, 258 patients of either sex were included in a randomized, placebo-controlled, double-blind clinical trial in parallel groups. Treatment groups were well-balanced with respect to demographics and baseline characteristics with a slight imbalance in baseline pain and ethnicity.

After surgery, all patients were initially treated with local post-operative anesthesia via a popliteal block. Due to different kinetics of the compound according to formula (I'b) and morphine, the patients were then treated with either one of the two drugs or with placebo at slightly different times:

One hour before the popliteal block was stopped, patients were randomized and part of them were dosed with a single dose of the compound according to formula (I'b) (200 μg, 400 μg or 600 μg) or placebo, while the others received morphine or placebo 2 hours after the popliteal block had been stopped.

The primary efficacy assessment endpoint was the absolute pain intensity over a 24 hour period. Pain intensity was measured using an 11-point numerical rating scale (NRS). At each time point, patients were instructed to evaluate their current pain intensity relative to an 11-point numerical rating scale. A score of zero represented no pain and a score of 10 represented worst possible pain. Missing scheduled pain assessments for the patients were imputed with the last observation carried forward (LOCF). The resulting averaged NRS values over the 24 hour period are depicted in FIG. 1.

Sum of pain intensity differences over different time periods were analyzed using an analysis of covariance (ANCOVA) model with factors for treatment and site and baseline pain intensity score (using the pain intensity NPRS score). Only subjects with non-missing baseline pain intensity were included. A summary of the analysis for the 2 to 10 hour period is presented in Table 23. The resulting p-values are summarized in Table 24.

TABLE 23

|  | n | LS mean | SE | LS mean Δplacebo | SE | P-value |
|---|---|---|---|---|---|---|
| Placebo | 45 | 49.13 | 2.85 |  |  |  |
| compound (I'b) 200 μg | 52 | 46.05 | 2.78 | −3.08 | 3.49 | 0.3776 |
| compound (I'b) 400 μg | 47 | 35.28 | 2.81 | −13.85 | 3.57 | 0.0001 |
| compound (I'b) 600 μg | 55 | 35.15 | 2.67 | −13.98 | 3.45 | <0.0001 |
| morphine, controlled-release 60 mg | 49 | 42.01 | 2.83 | −7.12 | 3.54 | 0.0454 |

LS mean: least squares means; SE: statistical error

The resulting p-values of the analysis of all time windows evaluated are summarized in Table 24.

TABLE 24

|  | p-values (sum of pain intensity differences) | | | | | |
|---|---|---|---|---|---|---|
|  | 2-6 h | 2-10 h | 2-12 h | 2-14 h | 2-18 h | 2-24 h |
| compound (I'b) 200 μg | 0.4514 | 0.3776 | 0.3387 | 0.3427 | 0.3205 | 0.2923 |
| compound (I'b) 400 μg | 0.0009 | 0.0001 | <0.0001 | 0.0001 | 0.0005 | 0.0008 |
| compound (I'b) 600 μg | 0.0009 | <0.0001 | <0.0001 | <0.0001 | <0.0001 | 0.0001 |
| morphine, controlled-release 60 mg | 0.4664 | 0.0454 | 0.0084 | 0.0036 | 0.0014 | 0.0005 |

Accordingly, on the primary parameter, a statistically significant difference was observed between groups that had received a 400 µg or 600 µg dose of compound (I'b) and placebo groups, whereas no statistically significant difference was observed for groups that had received a 200 µg dose of compound (I'b).

Tables 25 and 26 summarize the treatment emergent adverse events (TEAE(s)) experienced by the five treatment groups.

TABLE 25

|  | Placebo | compound (I'b) 200 µg | compound (I'b) 400 µg | compound (I'b) 600 µg | morphine 60 mg |
|---|---|---|---|---|---|
| subjects with TEAE(s) (n (%)) | 32 (68.1) | 37 (67.3) | 38 (77.6) | 48 (84.2) | 46 (92.0) |
| related (n (%)) | 17 (36.2) | 24 (43.6) | 32 (65.3) | 43 (75.4) | 42 (84.0) |
| serious (n (%)) | 1 (2.1) | 0 | 0 | 0 | 0 |
| total number of TEAE's (n) | 74 | 75 | 125 | 198 | 144 |
| related (n (%)) | 32 (43.2) | 37 (49.3) | 74 (59.2) | 146 (73.7) | 99 (68.8) |
| subjects with SAE's | 1 (2.1) | 0 | 0 | 0 | 0 |
| deaths | 0 | 0 | 0 | 0 | 0 |

TEAE: treatment emergent adverse event;
SAE: serious adverse event

TABLE 26

|  | Placebo | compound (I'b) 200 µg | compound (I'b) 400 µg | compound (I'b) 600 µg | morphine 60 mg |
|---|---|---|---|---|---|
| Nausea | 17.0 | 29.1 | 49.0 | 64.9 | 66.0 |
| Vomiting | 2.1 | 9.1 | 20.4 | 49.1 | 40.0 |
| Dizziness | 6.4 | 20.0 | 22.4 | 26.3 | 24.0 |
| Somnolence | 2.1 | 1.8 | 10.2 | 14.0 | 16.0 |
| ASAT increased | 2.1 | 1.8 | 6.1 | 1.8 | 2.0 |
| Hot flush | 0 | 1.8 | 4.1 | 7.0 | 4.0 |
| Pruritus | 0 | 0 | 6.1 | 3.5 | 2.0 |
| Hyperhidrosis | 0 | 0 | 0 | 5.3 | 6.0 |

100% = total number of subjects in corresponding treatment group;
ASAT: aspartate aminotransferase It becomes evident from Tables 25 and 26 that all four active treatments were well tolerated under these circumstances and the adverse events that showed up most frequently are in line with what can be expected from µ-opioid receptor agonists. For the patient group that had been treated with compound (I'b), the incidence of adverse events increased with the dose, and at a dose of 600 µg the incidence of adverse events was comparable to that of the morphine patient group, although the 400 µg dose was already comparable in efficacy.

Example 8

Clinical studies were conducted to determine the bioavailability of a liquid filled capsule formulation containing compound (I'b) in a dose strength of 400 µg compared to a hemicitrate oral solution of compound (I'b) (400 µg, 400 µg/mL oral solution) in a Macrogol 400 formulation after single oral administration. 24 healthy white male subjects were included in a randomized, open-label, 3-way crossover, single-center clinical trial. The main pharmacokinetic parameters were $AUC_{0-t}$, $AUC_{0-72h}$, and $C_{max}$.

The results are summarized in Tables 27 to 29.

TABLE 27

| pharmacokinetic parameter | $t_{max}$* [h] | $C_{max}$ [pg/mL] | $AUC_{0-72h}$ [h · pg/mL] | $AUC_{0-t}$ [h · pg/mL] |
|---|---|---|---|---|
| 400 µg/mL oral solution | 6.00 (2.08; 6.00) | 127 ± 52.4 (41.2%) | 2771 ± 1376 (49.7%) | 3843 ± 2081 (54.1%) |
| 400 µg capsule | 6.00 (2.08; 10.0) | 131 ± 58.1 (44.2%) | 2814 ± 1637 (58.2%) | 3733 ± 2265 (60.7%) |

N = 24; The table presents the arithmetic means +/− the standard deviation (coefficient of variation).

TABLE 28

| comparison capsules/oral solution | $C_{max}$ | $AUC_{0-72h}$ | $AUC_{0-t}$ |
|---|---|---|---|
| 400 µg capsule/ 400 µg/mL oral solution | 105% (94.4%-116%) | 105% (96%-116%) | 100% (91.0%-111%) |

TABLE 29

|  | total number of subjects (N) | Subjects with TEAE(s) n | TEAE(s) % | TEAE(S) e |
|---|---|---|---|---|
| 400 µg capsule | 24 | 14 | 58.3 | 32 |
| 400 µg/mL oral solution | 24 | 18 | 75.0 | 43 | n: number of subjects with at least one TEAE (treatment emergent adverse event);
%: corresponding ratio of subjects experiencing TEAE(s);
e: number of TEAE(s)

Accordingly, the relative bioavailability of the 400 µg capsule and 400 µg/mL oral solution based on $AUC_{0-72h}$ was 105%, with 90%-Cl within the 80% to 125% range conventionally used for assessing bioequivalence.

Single oral dose administrations of 400 µg of compound (I'b) were safe and well tolerated independent from the galenic formulation. No serious adverse events occurred.

Prophetic Examples

Prophetic examples of pharmaceutical dosage forms according to the invention are provided below. Their compositions are intended to be exemplary and it should be understood that the ingredients, the amount thereof and the procedure to obtain the dosage form may be varied.

According to example 6, hard gelatin capsules containing compound (I'b) in a dosage of, for instance, 40 or 400 µg, can also be produced by means of the following SMEDDS formulations:

| Ingredients [%] | PE-A1 | PE-A2 | IPE-A3 | IPE-A4 | IPE-A5 |
|---|---|---|---|---|---|
| Solutol ® HS 15 | 10 | 17.5 | 25 | 32.5 | 40 |
| Miglyol 812 | 60 | 55 | 50 | 40 | 30 |
| Ethanol (abs.) | 30 | 27.5 | 25 | 27.5 | 30 |

|  | PE-A6 | PE-A7 | IPE-A8 | IPE-A9 | PE-A10 |
|---|---|---|---|---|---|
| Solutol ® HS 15 | 45 | 50 | 65 | 80 | 87.5 |
| Miglyol 812 | 27.5 | 25 | 20 | 15 | 10 |
| Ethanol (abs.) | 27.5 | 25 | 15 | 5 | 2.5 |

| Ingredients [%] | PE-B1 | PE-B2 | PE-B3 | PE-B4 | PE-B5 |
|---|---|---|---|---|---|
| Gelucire 44/14 | 50 | 55 | 60 | 62.5 | 65 |
| Labrasol | 25 | 22.5 | 20 | 20 | 20 |
| Capryol 90 | 25 | 22.5 | 20 | 17.5 | 15 |

| Ingredients [%] | PE-B6 | PE-B7 | PE-B8 | PE-B9 | PE-B10 |
|---|---|---|---|---|---|
| Gelucire 44/14 | 67.5 | 70 | 75 | 80 | 82.5 |
| Labrasol | 17.5 | 15 | 12.5 | 10 | 7.5 |
| Capryol 90 | 15 | 15 | 12.5 | 10 | 10 |

| Ingredients [%] | PE-C1 | PE-C2 | PE-C3 | PE-C4 | PE-C5 |
|---|---|---|---|---|---|
| Cremophor RH 40 | 5 | 12.5 | 20 | 25 | 30 |
| Peceol | 15 | 17.5 | 20 | 20 | 20 |
| Miglyol 812 | 80 | 70 | 60 | 55 | 50 |

| Ingredients [%] | PE-C6 | PE-C7 | PE-C8 | PE-C9 | PE-C10 |
|---|---|---|---|---|---|
| Cremophor RH 40 | 35 | 40 | 47.5 | 55 | 60 |
| Peceol | 20 | 20 | 17.5 | 15 | 12.5 |
| Miglyol 812 | 45 | 40 | 35 | 30 | 27.5 |

General Procedure for Preparing the Solid Solution According to the Invention

Active pharmaceutical ingredient (API), i.e. the pharmacologically active agent according to general formula (I), and a polymer were dispersed in dichloromethane in a flask. In some cases, a surfactant was added. The flask was heated and subjected to ultrasound in order to dissolve the ingredients properly. Where applicable, the solution was filtered through a sintered glass filter in order to remove traces of undissolved material. The solvent was evaporated by means of a rotary evaporator at a temperature of 60° C. The solid residue was further dried under high vacuum overnight. The dried material was transferred to a sealed glass vial for the analysis for amorphous contents by using XRPD and DSC. The dissolution behavior was analyzed in 0.1N HCl.

Example 9

Following the general procedure, solid solutions having the following compositions were prepared:

| Ex. | API | polymer | weight ratio API:polymer | surfactant | content surfactant |
|---|---|---|---|---|---|
| 1-A | + | — | — | — | — |
| 1-B | + | Kollidon 90 | 1:4 | — | — |
| 1-C | + | Kollidon 90 | 1:4 | Pluronic F68 | 5 wt.-% |
| 1-D | + | Kollidon VA 64 | 1:5 | Tween 80 | 5 wt.-% |
| 1-E | + | Kollidon VA 64 | 1:19 | Tween 80 | 5 wt.-% |

Figure 2:
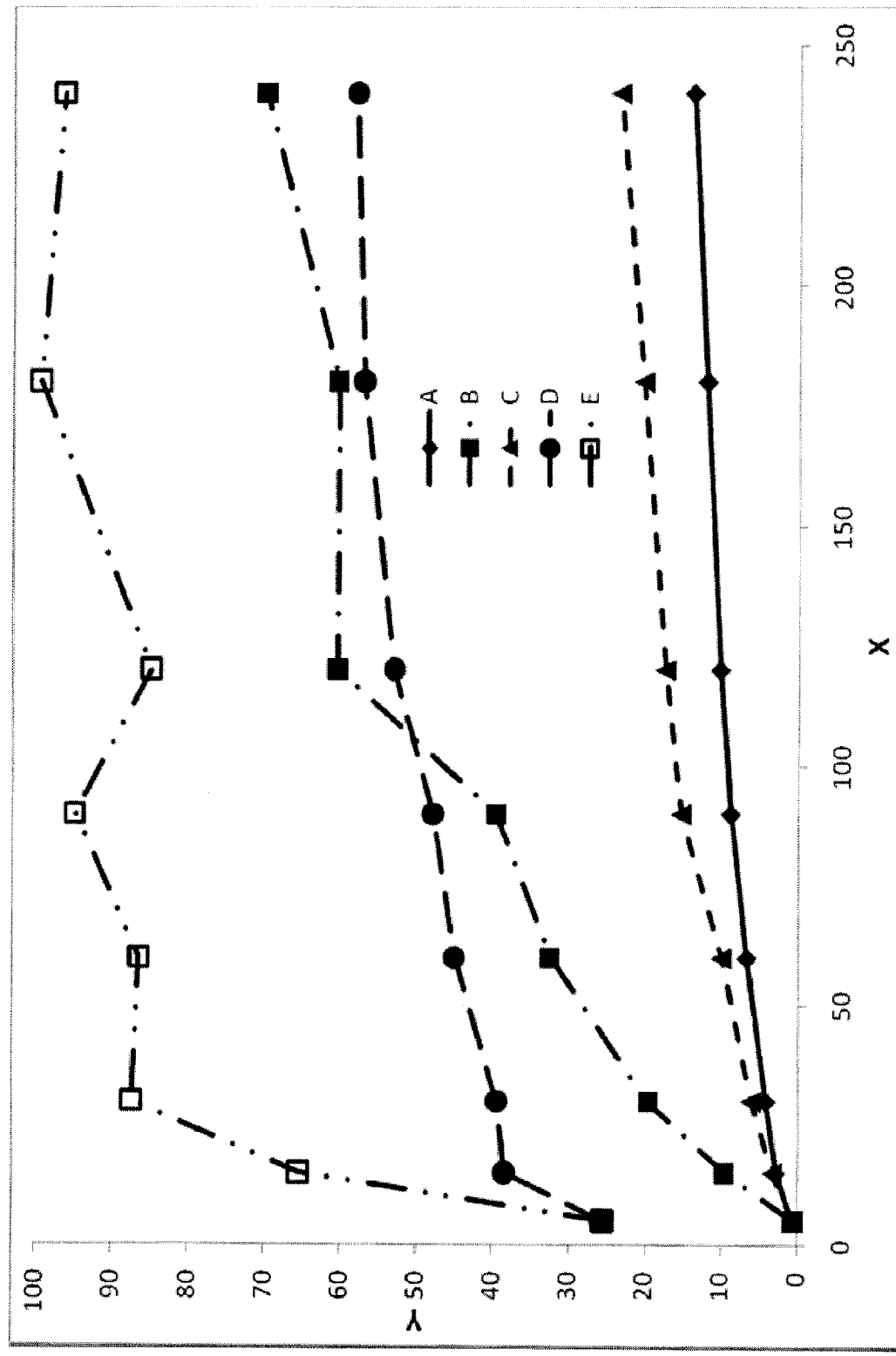
FIG. 2 shows the release profile of the pharmacologically active agent according to general formula (I'b) from the pure solid itself (A), from solid formulations containing the active agent and a polymer (Kollidon 90; B) and from solid solutions containing the active agent, a polymer (Kollidon 90 or Kollidon VA 64) and a surfactant (Pluronic F68 or Tween 80; C-E) in hydrochloric acid (0.1 N). The X-Axis refers to the time in minutes and the Y-Axis refers to the amount of dissolved active agent in percent in relation to the whole amount of active agent originally contained in the dosage form.

FIG. 2 shows the release profile of the API. The X-Axis refers to the time in minutes and the Y-Axis refers to the amount of dissolved API in percent in relation to the whole amount API originally contained in the dosage form.

It becomes evident from FIG. 2 that the solid solution containing Kollidon VA64/Tween 80 in a ratio of 1:19 of the API and the polymer (example 1-E) showed a substantially higher dissolution rate than any of the other formulations (examples 1-A to 1-D). Nearly 90% of the API was dissolved in the first 30 minutes. Pluronic F68 to the formulation with Kollidon 90 (1:4) resulted in a substantial decrease of the dissolution rate. Pluronic F68 is a difunctional block copolymer surfactant terminating in primary hydroxyl groups and having a HLB value of >24.

Example 10

Following the general procedure and in analogy to example 1, solid solutions having the following compositions were prepared:

| Ex. | API | polymer | weight ratio API: polymer | surfactant | content surfactant |
|---|---|---|---|---|---|
| 2-A | + | — | — | — | — |
| 2-B | + | Kollidon VA64 | 1:19 | — | — |
| 2-C | + | Kollidon VA64 | 1:19 | Tween 80 | 5 wt.-% |

Figure 3:
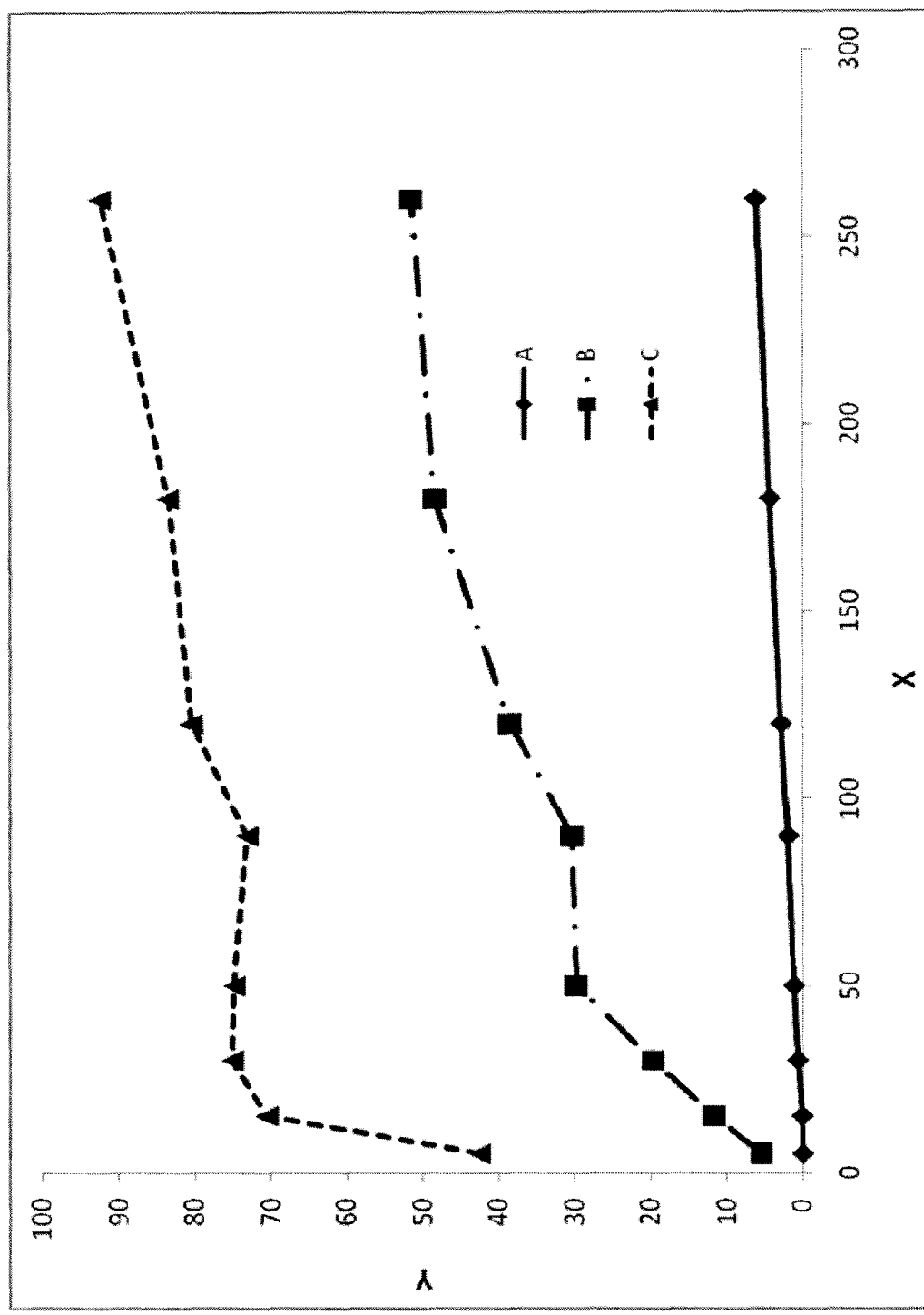
FIG. 3 shows the release profile of the pharmacologically active agent according to general formula (I'b) from the pure solid itself (A), from a solid formulation containing the active agent and a polymer (Kollidon VA64; B) and from solid solutions containing the active agent, a polymer (Kollidon VA 64) and a surfactant (Tween 80; C) in hydrochloric acid (0.1 N). The X-Axis refers to the time in minutes and the Y-Axis refers to the amount of dissolved active agent in percent in relation to the whole amount of active agent originally contained in the dosage form.

FIG. 3 shows the release profile of the API. The X-Axis refers to the time in minutes and the Y-Axis refers to the amount of dissolved API in percent in relation to the whole amount API originally contained in the dosage form.

It becomes evident from FIG. 3 that the formulation containing Tween 80 provided a faster release with a high extent of dissolution, while in the absence of the surfactant the dissolution rate was reduced; in the absence of surfactant (example 2-B), the overall extent of dissolution was only 55% compared to the formulation containing Tween 80 (example 2-C).

Example 11

The storage stability of a solid solution was tested under various conditions and analyzed by using XRPD. The solid solution was prepared in accordance with examples 1 and 2 and had the following composition:

| Ex. | API | polymer | weight ratio API:polymer | surfactant | content surfactant |
|---|---|---|---|---|---|
| 3 | + | Kollidon VA64 | 1:19 | Tween 80 | 4 wt.-% |

Unit doses of the blended formulation were filled into size 0 hard gelatin capsules. The encapsulated formulations were stored at 25° C. and 60% relative humidity (RH) at 30° C. and 65% relative humidity, respectively. After predetermined time periods of 1, 2, and 4 weeks, the capsules were removed from the storage and analyzed.

The solid solution of the API, especially the formulation with API:V64 in a ratio of 1:19, revealed to be physically stable over a time period of 4 weeks at 25° C. and 30° C. demonstrated via XRPD.

Figure 4:
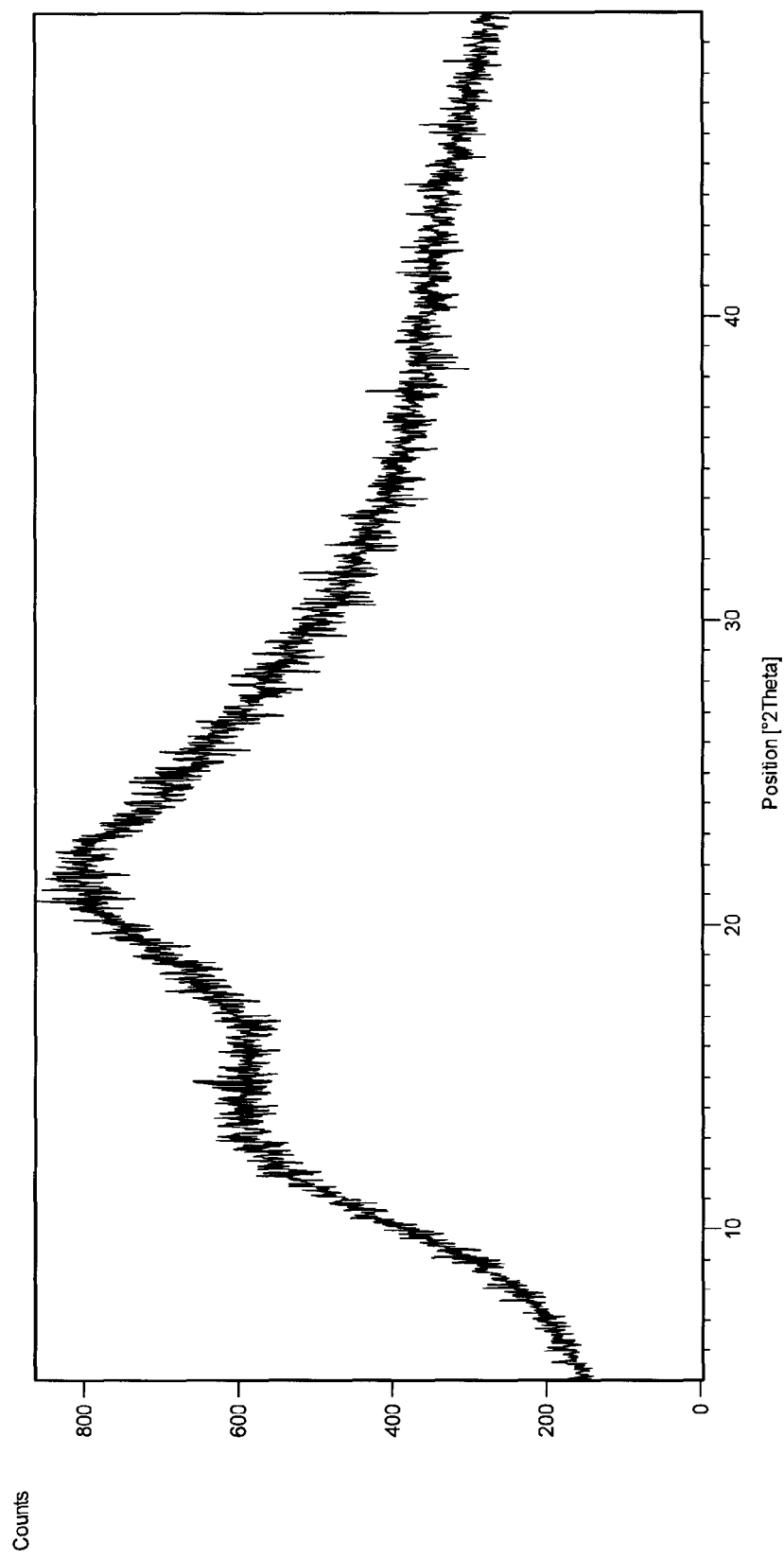
FIG. 4 shows the X-ray powder diffractogram of a solid solution containing the pharmacologically active agent according to general formula (I'b), polymer Kollidon VA64 and surfactant Tween 80 before being objected to a storage stability test.

FIG. 4 shows the XRPD result of the API solid solution at time zero.

Figure 5:
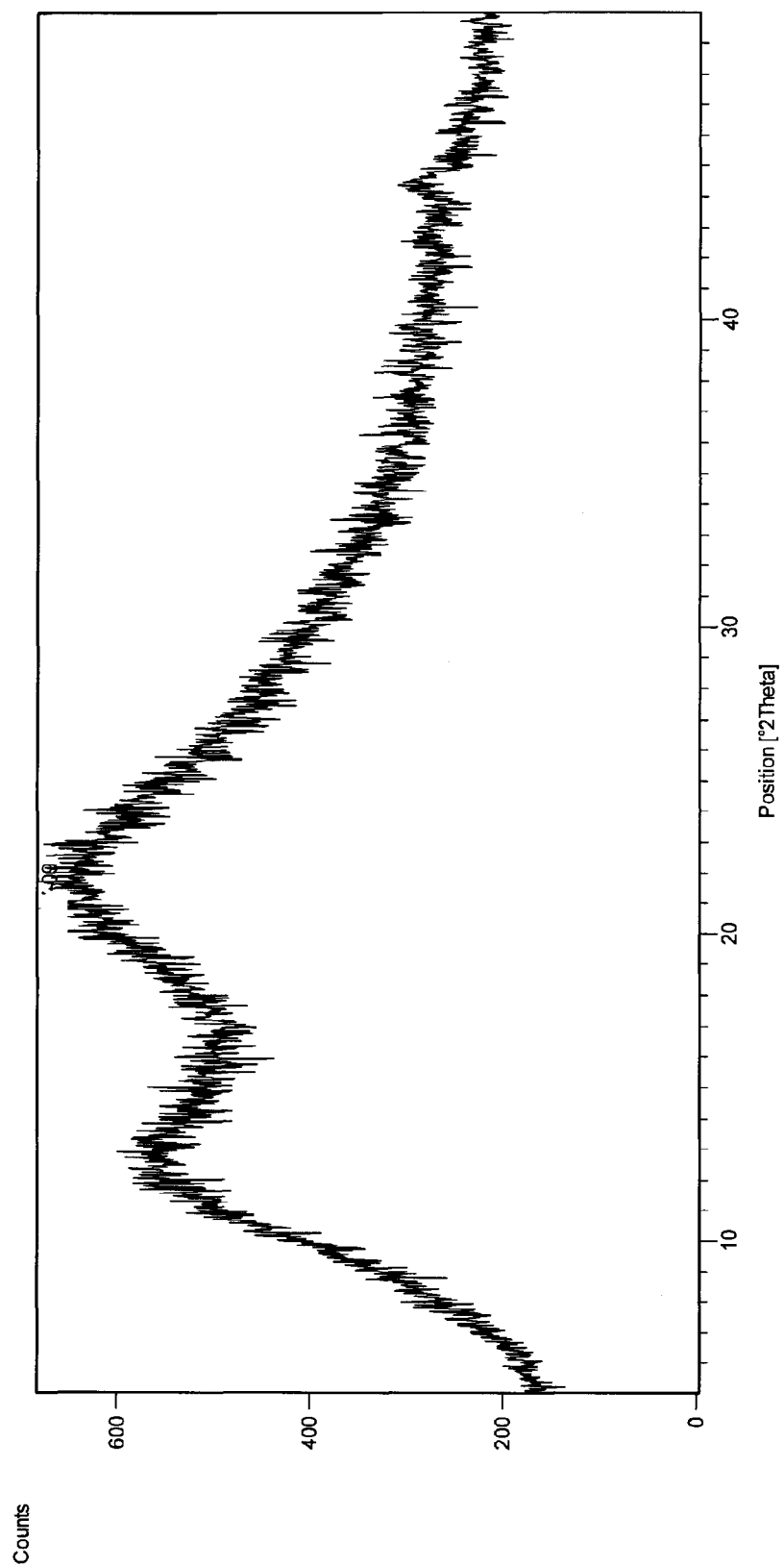
FIG. 5 shows the X-ray powder diffractogram of a solid solution containing the pharmacologically active agent according to general formula (I'b), polymer Kollidon VA64 and surfactant Tween 80 after 4 weeks of storage at 25° C. and 60% relative humidity.
Figure 6:
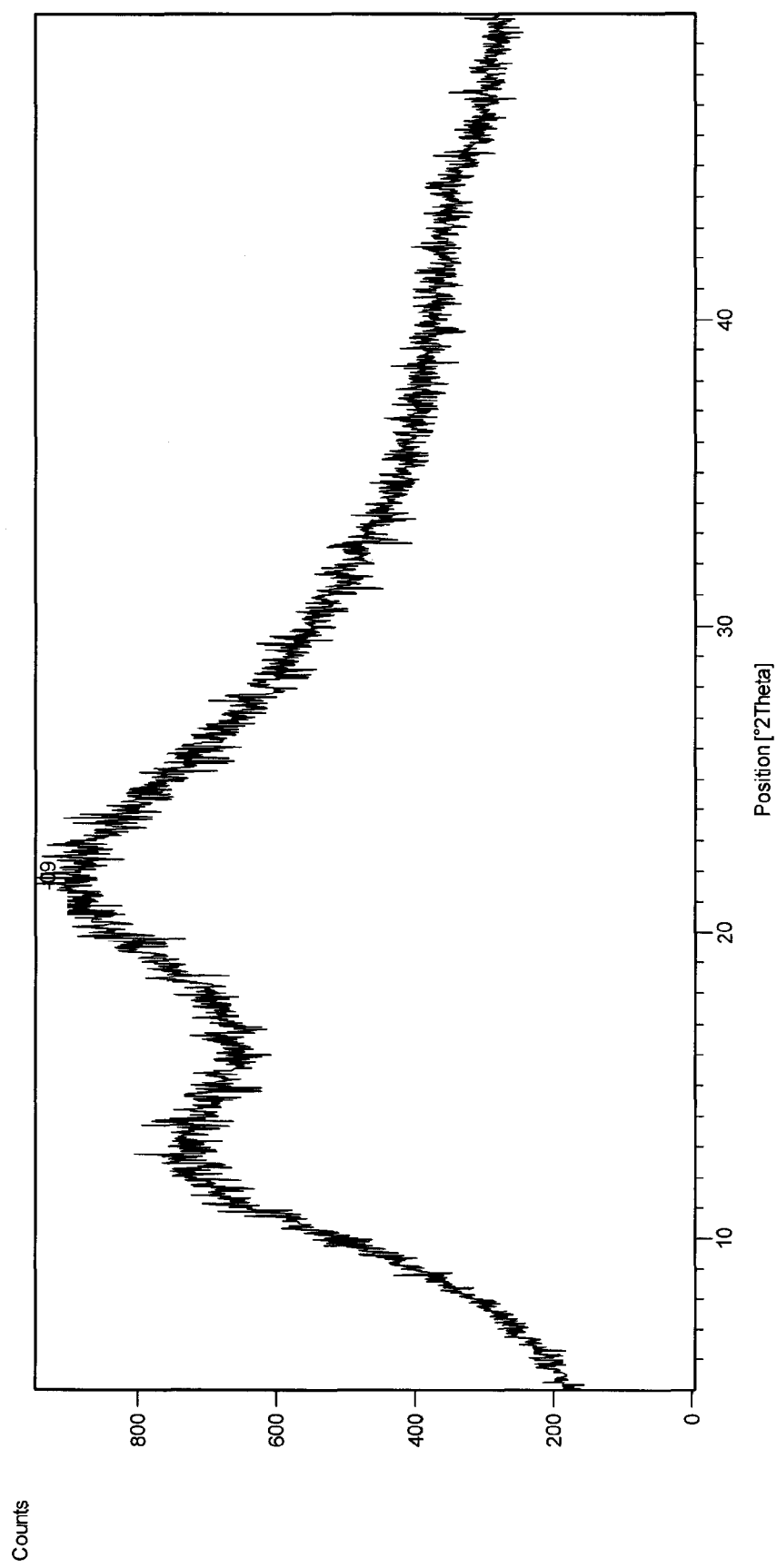
FIG. 6 shows the X-ray powder diffractogram of a solid solution containing the pharmacologically active agent according to general formula (I'b), polymer Kollidon VA64 and surfactant Tween 80 after 4 weeks of storage at 30° C. and 65% relative humidity.

FIGS. 5 and 6 show the result after 4 weeks of storage at 25° C. and 60% relative humidity and at 30° C. and 65% relative humidity, respectively.

It is clear from FIGS. 4 to 6 that the drug product has amorphous or at least semi-amorphous nature.

Example 12

Clinical studies were conducted to determine the analgesic efficacy and tolerability of single doses of the compound according to formula (I'b) (200 µg, 400 µg and 600 µg, based on the amount of the free base; hemicitrate oral solution of compound (I'b) in Macrogol 400) compared to that of morphine (60 mg, controlled-released form) and placebo in patients with acute post-operative pain following orthopedic surgery (bunionectomy).

For this purpose, 258 patients of either sex were included in a randomized, placebo-controlled, double-blind clinical trial in parallel groups. Treatment groups were well-balanced with respect to demographics and baseline characteristics with a slight imbalance in baseline pain and ethnicity.

After surgery, all patients were initially treated with local post-operative anesthesia via a popliteal block. Due to different kinetics of the compound according to formula (I'b) and morphine, the patients were then treated with either one of the two drugs or with placebo at slightly different times:

One hour before the popliteal block was stopped, patients were randomized and part of them were dosed with a single dose of the compound according to formula (I'b) (200 µg, 400 µg or 600 µg) or placebo, while the others received morphine or placebo 2 hours after the popliteal block had been stopped.

The primary efficacy assessment endpoint was the absolute pain intensity over a 24 hour period. Pain intensity was measured using an 11-point numerical rating scale (NRS). At each time point, patients were instructed to evaluate their current pain intensity relative to an 11-point numerical rating scale. A score of zero represented no pain and a score of 10 represented worst possible pain. Missing scheduled pain assessments for the patients were imputed with the last observation carried forward (LOCF). The resulting averaged NRS values over the 24 hour period are depicted in FIG. 6.

Sum of pain intensity differences over different time periods were analyzed using an analysis of covariance (ANCOVA) model with factors for treatment and site and baseline pain intensity score (using the pain intensity NPRS score). Only subjects with non-missing baseline pain intensity were included. A summary of the analysis for the 2 to 10 hour period is presented in the following Table 30:

TABLE 30

| | n | LS mean | SE | LS mean Δplacebo | SE | P-value |
|---|---|---|---|---|---|---|
| placebo | 45 | 49.13 | 2.85 | | | |
| compound (I'b) 200 µg | 52 | 46.05 | 2.78 | −3.08 | 3.49 | 0.3776 |
| compound (I'b) 400 µg | 47 | 35.28 | 2.81 | −13.85 | 3.57 | 0.0001 |
| compound (I'b) 600 µg | 55 | 35.15 | 2.67 | −13.98 | 3.45 | <0.0001 |
| morphine, controlled-release 60 mg | 49 | 42.01 | 2.83 | −7.12 | 3.54 | 0.0454 |

LS mean: least squares means; SE: statistical error

The resulting p-values are summarized in the following Table 31:

TABLE 31

| | p-values (sum of pain intensity differences) | | | | | |
|---|---|---|---|---|---|---|
| | 2-6 h | 2-10 h | 2-12 h | 2-14 h | 2-18 h | 2-24 h |
| compound (I'b) 200 µg | 0.4514 | 0.3776 | 0.3387 | 0.3427 | 0.3205 | 0.2923 |
| compound (I'b) 400 µg | 0.0009 | 0.0001 | <0.0001 | 0.0001 | 0.0005 | 0.0008 |

TABLE 31-continued

| | p-values (sum of pain intensity differences) | | | | | |
|---|---|---|---|---|---|---|
| | 2-6 h | 2-10 h | 2-12 h | 2-14 h | 2-18 h | 2-24 h |
| compound (I'b) 600 μg | 0.0009 | <0.0001 | <0.0001 | <0.0001 | <0.0001 | 0.0001 |
| morphine, controlled-release 60 mg | 0.4664 | 0.0454 | 0.0084 | 0.0036 | 0.0014 | 0.0005 |

Accordingly, on the primary parameter, a statistically significant difference was observed between groups that had received a 400 μg or 600 μg dose of compound (I'b) and placebo groups, whereas no statistically significant difference was observed for groups that had received a 200 μg dose of compound (I'b).

The following Tables 32 and 33 summarize the treatment emergent adverse events (TEAE(s)) experienced by the five treatment groups.

TABLE 32

| | Placebo | compound (I'b) 200 μg | compound (I'b) 400 μg | compound (I'b) 600 μg | morphine 60 mg |
|---|---|---|---|---|---|
| subjects with TEAE(s) (n (%)) | 32 (68.1) | 37 (67.3) | 38 (77.6) | 48 (84.2) | 46 (92.0) |
| related (n (%)) | 17 (36.2) | 24 (43.6) | 32 (65.3) | 43 (75.4) | 42 (84.0) |
| serious (n (%)) | 1 (2.1) | 0 | 0 | 0 | 0 |
| total number of TEAE's (n) | 74 | 75 | 125 | 198 | 144 |
| related (n (%)) | 32 (43.2) | 37 (49.3) | 74 (59.2) | 146 (73.7) | 99 (68.8) |
| subjects with SAE's | 1 (2.1) | 0 | 0 | 0 | 0 |
| Deaths | 0 | 0 | 0 | 0 | 0 |

TEAE: treatment emergent adverse event;
SAE: serious adverse event

TABLE 33

| | Placebo | compound (I'b) 200 μg | compound (I'b) 400 μg | compound (I'b) 600 μg | morphine 60 mg |
|---|---|---|---|---|---|
| Nausea | 17.0 | 29.1 | 49.0 | 64.9 | 66.0 |
| Vomiting | 2.1 | 9.1 | 20.4 | 49.1 | 40.0 |
| Dizziness | 6.4 | 20.0 | 22.4 | 26.3 | 24.0 |
| Somnolence | 2.1 | 1.8 | 10.2 | 14.0 | 16.0 |
| ASAT increased | 2.1 | 1.8 | 6.1 | 1.8 | 2.0 |
| Hot flush | 0 | 1.8 | 4.1 | 7.0 | 4.0 |
| Pruritus | 0 | 0 | 6.1 | 3.5 | 2.0 |
| Hyperhidrosis | 0 | 0 | 0 | 5.3 | 6.0 |

100% = total number of subjects in corresponding treatment group;
ASAT: aspartate aminotransferase It becomes evident from the foregoing Tables 32 and 33 that all four active treatments were well tolerated under these circumstances and the adverse events that showed up most frequently are in line with what can be expected from μ-opioid receptor agonists. For the patient group that had been treated with compound (I'b), the incidence of adverse events increased with the dose, and at a dose of 600 μg the incidence of adverse events was comparable to that of the morphine patient group.

Prophetic Examples

Prophetic examples of pharmaceutical dosage forms according to the invention are provided below. Their compositions are intended to be exemplary and it should be understood that the ingredients, the amount thereof and the procedure to obtain the dosage form may be varied.

In analogy to examples 1, 2 and 3, the following compositions (solid solutions) can be prepared in accordance with the general procedure:

| Ex. | API | polymer | weight ratio API:polymer | surfactant | content surfactant |
|---|---|---|---|---|---|
| P1-1-A-1 | + | Kollidon 90 | 1:8 | Tween 80 | 1 wt.-% |
| P1-1-A-2 | + | Kollidon 90 | 1:8 | Tween 80 | 2.5 wt.-% |
| P1-1-A-3 | + | Kollidon 90 | 1:8 | Tween 80 | 5 wt.-% |
| P1-1-A-4 | + | Kollidon 90 | 1:8 | Tween 80 | 7.5 wt.-% |
| P1-1-A-5 | + | Kollidon 90 | 1:8 | Tween 80 | 10 wt.-% |
| P1-1-B-1 | + | Kollidon 90 | 1:12 | Tween 80 | 1 wt.-% |
| P1-1-B-2 | + | Kollidon 90 | 1:12 | Tween 80 | 2.5 wt.-% |
| P1-1-B-3 | + | Kollidon 90 | 1:12 | Tween 80 | 5 wt.-% |
| P1-1-B-4 | + | Kollidon 90 | 1:12 | Tween 80 | 7.5 wt.-% |
| P1-1-B-5 | + | Kollidon 90 | 1:12 | Tween 80 | 10 wt.-% |
| P1-1-C-1 | + | Kollidon 90 | 1:16 | Tween 80 | 1 wt.-% |
| P1-1-C-2 | + | Kollidon 90 | 1:16 | Tween 80 | 2.5 wt.-% |
| P1-1-C-3 | + | Kollidon 90 | 1:16 | Tween 80 | 5 wt.-% |
| P1-1-C-4 | + | Kollidon 90 | 1:16 | Tween 80 | 7.5 wt.-% |
| P1-1-C-5 | + | Kollidon 90 | 1:16 | Tween 80 | 10 wt.-% |
| P1-1-D-1 | + | Kollidon 90 | 1:20 | Tween 80 | 1 wt.-% |
| P1-1-D-2 | + | Kollidon 90 | 1:20 | Tween 80 | 2.5 wt.-% |
| P1-1-D-3 | + | Kollidon 90 | 1:20 | Tween 80 | 5 wt.-% |
| P1-1-D-4 | + | Kollidon 90 | 1:20 | Tween 80 | 7.5 wt.-% |
| P1-1-D-5 | + | Kollidon 90 | 1:20 | Tween 80 | 10 wt.-% |
| P1-1-E-1 | + | Kollidon 90 | 1:24 | Tween 80 | 1 wt.-% |
| P1-1-E-2 | + | Kollidon 90 | 1:24 | Tween 80 | 2.5 wt.-% |
| P1-1-E-3 | + | Kollidon 90 | 1:24 | Tween 80 | 5 wt.-% |
| P1-1-E-4 | + | Kollidon 90 | 1:24 | Tween 80 | 7.5 wt.-% |
| P1-1-E-5 | + | Kollidon 90 | 1:24 | Tween 80 | 10 wt.-% |
| P1-2-A-1 | + | Kollidon 90 | 1:8 | Solutol HS 15 | 1 wt.-% |
| P1-2-A-2 | + | Kollidon 90 | 1:8 | Solutol HS 15 | 2.5 wt.-% |
| P1-2-A-3 | + | Kollidon 90 | 1:8 | Solutol HS 15 | 5 wt.-% |
| P1-2-A-4 | + | Kollidon 90 | 1:8 | Solutol HS 15 | 7.5 wt.-% |
| P1-2-A-5 | + | Kollidon 90 | 1:8 | Solutol HS 15 | 10 wt.-% |
| P1-2-B-1 | + | Kollidon 90 | 1:12 | Solutol HS 15 | 1 wt.-% |
| P1-2-B-2 | + | Kollidon 90 | 1:12 | Solutol HS 15 | 2.5 wt.-% |
| P1-2-B-3 | + | Kollidon 90 | 1:12 | Solutol HS 15 | 5 wt.-% |
| P1-2-B-4 | + | Kollidon 90 | 1:12 | Solutol HS 15 | 7.5 wt.-% |
| P1-2-B-5 | + | Kollidon 90 | 1:12 | Solutol HS 15 | 10 wt.-% |
| P1-2-C-1 | + | Kollidon 90 | 1:16 | Solutol HS 15 | 1 wt.-% |
| P1-2-C-2 | + | Kollidon 90 | 1:16 | Solutol HS 15 | 2.5 wt.-% |
| P1-2-C-3 | + | Kollidon 90 | 1:16 | Solutol HS 15 | 5 wt.-% |
| P1-2-C-4 | + | Kollidon 90 | 1:16 | Solutol HS 15 | 7.5 wt.-% |

-continued

| Ex. | API | polymer | weight ratio API:polymer | surfactant | content surfactant |
|---|---|---|---|---|---|
| P1-2-C-5 | + | Kollidon 90 | 1:16 | Solutol HS 15 | 10 wt.-% |
| P1-2-D-1 | + | Kollidon 90 | 1:20 | Solutol HS 15 | 1 wt.-% |
| P1-2-D-2 | + | Kollidon 90 | 1:20 | Solutol HS 15 | 2.5 wt.-% |
| P1-2-D-3 | + | Kollidon 90 | 1:20 | Solutol HS 15 | 5 wt.-% |
| P1-2-D-4 | + | Kollidon 90 | 1:20 | Solutol HS 15 | 7.5 wt.-% |
| P1-2-D-5 | + | Kollidon 90 | 1:20 | Solutol HS 15 | 10 wt.-% |
| P1-2-E-1 | + | Kollidon 90 | 1:24 | Solutol HS 15 | 1 wt.-% |
| P1-2-E-2 | + | Kollidon 90 | 1:24 | Solutol HS 15 | 2.5 wt.-% |
| P1-2-E-3 | + | Kollidon 90 | 1:24 | Solutol HS 15 | 5 wt.-% |
| P1-2-E-4 | + | Kollidon 90 | 1:24 | Solutol HS 15 | 7.5 wt.-% |
| P1-2-E-5 | + | Kollidon 90 | 1:24 | Solutol HS 15 | 10 wt.-% |
| P1-3-A-1 | + | Kollidon 90 | 1:8 | Tween 60 | 1 wt.-% |
| P1-3-A-2 | + | Kollidon 90 | 1:8 | Tween 60 | 2.5 wt.-% |
| P1-3-A-3 | + | Kollidon 90 | 1:8 | Tween 60 | 5 wt.-% |
| P1-3-A-4 | + | Kollidon 90 | 1:8 | Tween 60 | 7.5 wt.-% |
| P1-3-A-5 | + | Kollidon 90 | 1:8 | Tween 60 | 10 wt.-% |
| P1-3-B-1 | + | Kollidon 90 | 1:12 | Tween 60 | 1 wt.-% |
| P1-3-B-2 | + | Kollidon 90 | 1:12 | Tween 60 | 2.5 wt.-% |
| P1-3-B-3 | + | Kollidon 90 | 1:12 | Tween 60 | 5 wt.-% |
| P1-3-B-4 | + | Kollidon 90 | 1:12 | Tween 60 | 7.5 wt.-% |
| P1-3-B-5 | + | Kollidon 90 | 1:12 | Tween 60 | 10 wt.-% |
| P1-3-C-1 | + | Kollidon 90 | 1:16 | Tween 60 | 1 wt.-% |
| P1-3-C-2 | + | Kollidon 90 | 1:16 | Tween 60 | 2.5 wt.-% |
| P1-3-C-3 | + | Kollidon 90 | 1:16 | Tween 60 | 5 wt.-% |
| P1-3-C-4 | + | Kollidon 90 | 1:16 | Tween 60 | 7.5 wt.-% |
| P1-3-C-5 | + | Kollidon 90 | 1:16 | Tween 60 | 10 wt.-% |
| P1-3-D-1 | + | Kollidon 90 | 1:20 | Tween 60 | 1 wt.-% |
| P1-3-D-2 | + | Kollidon 90 | 1:20 | Tween 60 | 2.5 wt.-% |
| P1-3-D-3 | + | Kollidon 90 | 1:20 | Tween 60 | 5 wt.-% |
| P1-3-D-4 | + | Kollidon 90 | 1:20 | Tween 60 | 7.5 wt.-% |
| P1-3-D-5 | + | Kollidon 90 | 1:20 | Tween 60 | 10 wt.-% |
| P1-3-E-1 | + | Kollidon 90 | 1:24 | Tween 60 | 1 wt.-% |
| P1-3-E-2 | + | Kollidon 90 | 1:24 | Tween 60 | 2.5 wt.-% |
| P1-3-E-3 | + | Kollidon 90 | 1:24 | Tween 60 | 5 wt.-% |
| P1-3-E-4 | + | Kollidon 90 | 1:24 | Tween 60 | 7.5 wt.-% |
| P1-3-E-5 | + | Kollidon 90 | 1:24 | Tween 60 | 10 wt.-% |
| P1-4-A-1 | + | Kollidon 90 | 1:8 | Myrj 51 | 1 wt.-% |
| P1-4-A-2 | + | Kollidon 90 | 1:8 | Myrj 51 | 2.5 wt.-% |
| P1-4-A-3 | + | Kollidon 90 | 1:8 | Myrj 51 | 5 wt.-% |
| P1-4-A-4 | + | Kollidon 90 | 1:8 | Myrj 51 | 7.5 wt.-% |
| P1-4-A-5 | + | Kollidon 90 | 1:8 | Myrj 51 | 10 wt.-% |
| P1-4-B-1 | + | Kollidon 90 | 1:12 | Myrj 51 | 1 wt.-% |
| P1-4-B-2 | + | Kollidon 90 | 1:12 | Myrj 51 | 2.5 wt.-% |
| P1-4-B-3 | + | Kollidon 90 | 1:12 | Myrj 51 | 5 wt.-% |
| P1-4-B-4 | + | Kollidon 90 | 1:12 | Myrj 51 | 7.5 wt.-% |
| P1-4-B-5 | + | Kollidon 90 | 1:12 | Myrj 51 | 10 wt.-% |
| P1-4-C-1 | + | Kollidon 90 | 1:16 | Myrj 51 | 1 wt.-% |
| P1-4-C-2 | + | Kollidon 90 | 1:16 | Myrj 51 | 2.5 wt.-% |
| P1-4-C-3 | + | Kollidon 90 | 1:16 | Myrj 51 | 5 wt.-% |
| P1-4-C-4 | + | Kollidon 90 | 1:16 | Myrj 51 | 7.5 wt.-% |
| P1-4-C-5 | + | Kollidon 90 | 1:16 | Myrj 51 | 10 wt.-% |
| P1-4-D-1 | + | Kollidon 90 | 1:20 | Myrj 51 | 1 wt.-% |
| P1-4-D-2 | + | Kollidon 90 | 1:20 | Myrj 51 | 2.5 wt.-% |
| P1-4-D-3 | + | Kollidon 90 | 1:20 | Myrj 51 | 5 wt.-% |
| P1-4-D-4 | + | Kollidon 90 | 1:20 | Myrj 51 | 7.5 wt.-% |
| P1-4-D-5 | + | Kollidon 90 | 1:20 | Myrj 51 | 10 wt.-% |
| P1-4-E-1 | + | Kollidon 90 | 1:24 | Myrj 51 | 1 wt.-% |
| P1-4-E-2 | + | Kollidon 90 | 1:24 | Myrj 51 | 2.5 wt.-% |
| P1-4-E-3 | + | Kollidon 90 | 1:24 | Myrj 51 | 5 wt.-% |
| P1-4-E-4 | + | Kollidon 90 | 1:24 | Myrj 51 | 7.5 wt.-% |
| P1-4-E-5 | + | Kollidon 90 | 1:24 | Myrj 51 | 10 wt.-% |
| P1-5-A-1 | + | Kollidon 90 | 1:8 | Brij 98 | 1 wt.-% |
| P1-5-A-2 | + | Kollidon 90 | 1:8 | Brij 98 | 2.5 wt.-% |
| P1-5-A-3 | + | Kollidon 90 | 1:8 | Brij 98 | 5 wt.-% |
| P1-5-A-4 | + | Kollidon 90 | 1:8 | Brij 98 | 7.5 wt.-% |
| P1-5-A-5 | + | Kollidon 90 | 1:8 | Brij 98 | 10 wt.-% |
| P1-5-B-1 | + | Kollidon 90 | 1:12 | Brij 98 | 1 wt.-% |
| P1-5-B-2 | + | Kollidon 90 | 1:12 | Brij 98 | 2.5 wt.-% |
| P1-5-B-3 | + | Kollidon 90 | 1:12 | Brij 98 | 5 wt.-% |
| P1-5-B-4 | + | Kollidon 90 | 1:12 | Brij 98 | 7.5 wt.-% |
| P1-5-B-5 | + | Kollidon 90 | 1:12 | Brij 98 | 10 wt.-% |
| P1-5-C-1 | + | Kollidon 90 | 1:16 | Brij 98 | 1 wt.-% |
| P1-5-C-2 | + | Kollidon 90 | 1:16 | Brij 98 | 2.5 wt.-% |
| P1-5-C-3 | + | Kollidon 90 | 1:16 | Brij 98 | 5 wt.-% |
| P1-5-C-4 | + | Kollidon 90 | 1:16 | Brij 98 | 7.5 wt.-% |

-continued

| Ex. | API | polymer | weight ratio API:polymer | surfactant | content surfactant |
|---|---|---|---|---|---|
| P1-5-C-5 | + | Kollidon 90 | 1:16 | Brij 98 | 10 wt.-% |
| P1-5-D-1 | + | Kollidon 90 | 1:20 | Brij 98 | 1 wt.-% |
| P1-5-D-2 | + | Kollidon 90 | 1:20 | Brij 98 | 2.5 wt.-% |
| P1-5-D-3 | + | Kollidon 90 | 1:20 | Brij 98 | 5 wt.-% |
| P1-5-D-4 | + | Kollidon 90 | 1:20 | Brij 98 | 7.5 wt.-% |
| P1-5-D-5 | + | Kollidon 90 | 1:20 | Brij 98 | 10 wt.-% |
| P1-5-E-1 | + | Kollidon 90 | 1:24 | Brij 98 | 1 wt.-% |
| P1-5-E-2 | + | Kollidon 90 | 1:24 | Brij 98 | 2.5 wt.-% |
| P1-5-E-3 | + | Kollidon 90 | 1:24 | Brij 98 | 5 wt.-% |
| P1-5-E-4 | + | Kollidon 90 | 1:24 | Brij 98 | 7.5 wt.-% |
| P1-5-E-5 | + | Kollidon 90 | 1:24 | Brij 98 | 10 wt.-% |

Prophetic Example 2

| Ex. | API | polymer | weight ratio API:polymer | surfactant | content surfactant |
|---|---|---|---|---|---|
| P2-1-A-1 | + | Kollidon VA64 | 1:8 | Tween 80 | 1 wt.-% |
| P2-1-A-2 | + | Kollidon VA64 | 1:8 | Tween 80 | 2.5 wt.-% |
| P2-1-A-3 | + | Kollidon VA64 | 1:8 | Tween 80 | 5 wt.-% |
| P2-1-A-4 | + | Kollidon VA64 | 1:8 | Tween 80 | 7.5 wt.-% |
| P2-1-A-5 | + | Kollidon VA64 | 1:8 | Tween 80 | 10 wt.-% |
| P2-1-B-1 | + | Kollidon VA64 | 1:12 | Tween 80 | 1 wt.-% |
| P2-1-B-2 | + | Kollidon VA64 | 1:12 | Tween 80 | 2.5 wt.-% |
| P2-1-B-3 | + | Kollidon VA64 | 1:12 | Tween 80 | 5 wt.-% |
| P2-1-B-4 | + | Kollidon VA64 | 1:12 | Tween 80 | 7.5 wt.-% |
| P2-1-B-5 | + | Kollidon VA64 | 1:12 | Tween 80 | 10 wt.-% |
| P2-1-C-1 | + | Kollidon VA64 | 1:16 | Tween 80 | 1 wt.-% |
| P2-1-C-2 | + | Kollidon VA64 | 1:16 | Tween 80 | 2.5 wt.-% |
| P2-1-C-3 | + | Kollidon VA64 | 1:16 | Tween 80 | 5 wt.-% |
| P2-1-C-4 | + | Kollidon VA64 | 1:16 | Tween 80 | 7.5 wt.-% |
| P2-1-C-5 | + | Kollidon VA64 | 1:16 | Tween 80 | 10 wt.-% |
| P2-1-D-1 | + | Kollidon VA64 | 1:20 | Tween 80 | 1 wt.-% |
| P2-1-D-2 | + | Kollidon VA64 | 1:20 | Tween 80 | 2.5 wt.-% |
| P2-1-D-3 | + | Kollidon VA64 | 1:20 | Tween 80 | 5 wt.-% |
| P2-1-D-4 | + | Kollidon VA64 | 1:20 | Tween 80 | 7.5 wt.-% |
| P2-1-D-5 | + | Kollidon VA64 | 1:20 | Tween 80 | 10 wt.-% |
| P2-1-E-1 | + | Kollidon VA64 | 1:24 | Tween 80 | 1 wt.-% |
| P2-1-E-2 | + | Kollidon VA64 | 1:24 | Tween 80 | 2.5 wt.-% |
| P2-1-E-3 | + | Kollidon VA64 | 1:24 | Tween 80 | 5 wt.-% |
| P2-1-E-4 | + | Kollidon VA64 | 1:24 | Tween 80 | 7.5 wt.-% |
| P2-1-E-5 | + | Kollidon VA64 | 1:24 | Tween 80 | 10 wt.-% |
| P2-2-A-1 | + | Kollidon VA64 | 1:8 | Solutol HS 15 | 1 wt.-% |
| P2-2-A-2 | + | Kollidon VA64 | 1:8 | Solutol HS 15 | 2.5 wt.-% |
| P2-2-A-3 | + | Kollidon VA64 | 1:8 | Solutol HS 15 | 5 wt.-% |
| P2-2-A-4 | + | Kollidon VA64 | 1:8 | Solutol HS 15 | 7.5 wt.-% |
| P2-2-A-5 | + | Kollidon VA64 | 1:8 | Solutol HS 15 | 10 wt.-% |
| P2-2-B-1 | + | Kollidon VA64 | 1:12 | Solutol HS 15 | 1 wt.-% |
| P2-2-B-2 | + | Kollidon VA64 | 1:12 | Solutol HS 15 | 2.5 wt.-% |
| P2-2-B-3 | + | Kollidon VA64 | 1:12 | Solutol HS 15 | 5 wt.-% |
| P2-2-B-4 | + | Kollidon VA64 | 1:12 | Solutol HS 15 | 7.5 wt.-% |
| P2-2-B-5 | + | Kollidon VA64 | 1:12 | Solutol HS 15 | 10 wt.-% |
| P2-2-C-1 | + | Kollidon VA64 | 1:16 | Solutol HS 15 | 1 wt.-% |
| P2-2-C-2 | + | Kollidon VA64 | 1:16 | Solutol HS 15 | 2.5 wt.-% |
| P2-2-C-3 | + | Kollidon VA64 | 1:16 | Solutol HS 15 | 5 wt.-% |
| P2-2-C-4 | + | Kollidon VA64 | 1:16 | Solutol HS 15 | 7.5 wt.-% |
| P2-2-C-5 | + | Kollidon VA64 | 1:16 | Solutol HS 15 | 10 wt.-% |
| P2-2-D-1 | + | Kollidon VA64 | 1:20 | Solutol HS 15 | 1 wt.-% |
| P2-2-D-2 | + | Kollidon VA64 | 1:20 | Solutol HS 15 | 2.5 wt.-% |
| P2-2-D-3 | + | Kollidon VA64 | 1:20 | Solutol HS 15 | 5 wt.-% |
| P2-2-D-4 | + | Kollidon VA64 | 1:20 | Solutol HS 15 | 7.5 wt.-% |
| P2-2-D-5 | + | Kollidon VA64 | 1:20 | Solutol HS 15 | 10 wt.-% |
| P2-2-E-1 | + | Kollidon VA64 | 1:24 | Solutol HS 15 | 1 wt.-% |
| P2-2-E-2 | + | Kollidon VA64 | 1:24 | Solutol HS 15 | 2.5 wt.-% |
| P2-2-E-3 | + | Kollidon VA64 | 1:24 | Solutol HS 15 | 5 wt.-% |
| P2-2-E-4 | + | Kollidon VA64 | 1:24 | Solutol HS 15 | 7.5 wt.-% |
| P2-2-E-5 | + | Kollidon VA64 | 1:24 | Solutol HS 15 | 10 wt.-% |
| P2-3-A-1 | + | Kollidon VA64 | 1:8 | Pluronic F127 | 1 wt.-% |
| P2-3-A-2 | + | Kollidon VA64 | 1:8 | Pluronic F127 | 2.5 wt.-% |
| P2-3-A-3 | + | Kollidon VA64 | 1:8 | Pluronic F127 | 5 wt.-% |

| Ex. | API | polymer | weight ratio API: polymer | surfactant | content surfactant |
|---|---|---|---|---|---|
| P2-3-A-4 | + | Kollidon VA64 | 1:8 | Pluronic F127 | 7.5 wt.-% |
| P2-3-A-5 | + | Kollidon VA64 | 1:8 | Pluronic F127 | 10 wt.-% |
| P2-3-B-1 | + | Kollidon VA64 | 1:12 | Pluronic F127 | 1 wt.-% |
| P2-3-B-2 | + | Kollidon VA64 | 1:12 | Pluronic F127 | 2.5 wt.-% |
| P2-3-B-3 | + | Kollidon VA64 | 1:12 | Pluronic F127 | 5 wt.-% |
| P2-3-B-4 | + | Kollidon VA64 | 1:12 | Pluronic F127 | 7.5 wt.-% |
| P2-3-B-5 | + | Kollidon VA64 | 1:12 | Pluronic F127 | 10 wt.-% |
| P2-3-C-1 | + | Kollidon VA64 | 1:16 | Pluronic F127 | 1 wt.-% |
| P2-3-C-2 | + | Kollidon VA64 | 1:16 | Pluronic F127 | 2.5 wt.-% |
| P2-3-C-3 | + | Kollidon VA64 | 1:16 | Pluronic F127 | 5 wt.-% |
| P2-3-C-4 | + | Kollidon VA64 | 1:16 | Pluronic F127 | 7.5 wt.-% |
| P2-3-C-5 | + | Kollidon VA64 | 1:16 | Pluronic F127 | 10 wt.-% |
| P2-3-D-1 | + | Kollidon VA64 | 1:20 | Pluronic F127 | 1 wt.-% |
| P2-3-D-2 | + | Kollidon VA64 | 1:20 | Pluronic F127 | 2.5 wt.-% |
| P2-3-D-3 | + | Kollidon VA64 | 1:20 | Pluronic F127 | 5 wt.-% |
| P2-3-D-4 | + | Kollidon VA64 | 1:20 | Pluronic F127 | 7.5 wt.-% |
| P2-3-D-5 | + | Kollidon VA64 | 1:20 | Pluronic F127 | 10 wt.-% |
| P2-3-E-1 | + | Kollidon VA64 | 1:24 | Pluronic F127 | 1 wt.-% |
| P2-3-E-2 | + | Kollidon VA64 | 1:24 | Pluronic F127 | 2.5 wt.-% |
| P2-3-E-3 | + | Kollidon VA64 | 1:24 | Pluronic F127 | 5 wt.-% |
| P2-3-E-4 | + | Kollidon VA64 | 1:24 | Pluronic F127 | 7.5 wt.-% |
| P2-3-E-5 | + | Kollidon VA64 | 1:24 | Pluronic F127 | 10 wt.-% |
| P2-4-A-1 | + | Kollidon VA64 | 1:8 | Myrj 51 | 1 wt.-% |
| P2-4-A-2 | + | Kollidon VA64 | 1:8 | Myrj 51 | 2.5 wt.-% |
| P2-4-A-3 | + | Kollidon VA64 | 1:8 | Myrj 51 | 5 wt.-% |
| P2-4-A-4 | + | Kollidon VA64 | 1:8 | Myrj 51 | 7.5 wt.-% |
| P2-4-A-5 | + | Kollidon VA64 | 1:8 | Myrj 51 | 10 wt.-% |
| P2-4-B-1 | + | Kollidon VA64 | 1:12 | Myrj 51 | 1 wt.-% |
| P2-4-B-2 | + | Kollidon VA64 | 1:12 | Myrj 51 | 2.5 wt.-% |
| P2-4-B-3 | + | Kollidon VA64 | 1:12 | Myrj 51 | 5 wt.-% |
| P2-4-B-4 | + | Kollidon VA64 | 1:12 | Myrj 51 | 7.5 wt.-% |
| P2-4-B-5 | + | Kollidon VA64 | 1:12 | Myrj 51 | 10 wt.-% |
| P2-4-C-1 | + | Kollidon VA64 | 1:16 | Myrj 51 | 1 wt.-% |
| P2-4-C-2 | + | Kollidon VA64 | 1:16 | Myrj 51 | 2.5 wt.-% |
| P2-4-C-3 | + | Kollidon VA64 | 1:16 | Myrj 51 | 5 wt.-% |
| P2-4-C-4 | + | Kollidon VA64 | 1:16 | Myrj 51 | 7.5 wt.-% |
| P2-4-C-5 | + | Kollidon VA64 | 1:16 | Myrj 51 | 10 wt.-% |
| P2-4-D-1 | + | Kollidon VA64 | 1:20 | Myrj 51 | 1 wt.-% |
| P2-4-D-2 | + | Kollidon VA64 | 1:20 | Myrj 51 | 2.5 wt.-% |
| P2-4-D-3 | + | Kollidon VA64 | 1:20 | Myrj 51 | 5 wt.-% |
| P2-4-D-4 | + | Kollidon VA64 | 1:20 | Myrj 51 | 7.5 wt.-% |
| P2-4-D-5 | + | Kollidon VA64 | 1:20 | Myrj 51 | 10 wt.-% |
| P2-4-E-1 | + | Kollidon VA64 | 1:24 | Myrj 51 | 1 wt.-% |
| P2-4-E-2 | + | Kollidon VA64 | 1:24 | Myrj 51 | 2.5 wt.-% |
| P2-4-E-3 | + | Kollidon VA64 | 1:24 | Myrj 51 | 5 wt.-% |
| P2-4-E-4 | + | Kollidon VA64 | 1:24 | Myrj 51 | 7.5 wt.-% |
| P2-4-E-5 | + | Kollidon VA64 | 1:24 | Myrj 51 | 10 wt.-% |
| P2-5-A-1 | + | Kollidon VA64 | 1:8 | Brij 98 | 1 wt.-% |
| P2-5-A-2 | + | Kollidon VA64 | 1:8 | Brij 98 | 2.5 wt.-% |
| P2-5-A-3 | + | Kollidon VA64 | 1:8 | Brij 98 | 5 wt.-% |
| P2-5-A-4 | + | Kollidon VA64 | 1:8 | Brij 98 | 7.5 wt.-% |
| P2-5-A-5 | + | Kollidon VA64 | 1:8 | Brij 98 | 10 wt.-% |
| P2-5-B-1 | + | Kollidon VA64 | 1:12 | Brij 98 | 1 wt.-% |
| P2-5-B-2 | + | Kollidon VA64 | 1:12 | Brij 98 | 2.5 wt.-% |
| P2-5-B-3 | + | Kollidon VA64 | 1:12 | Brij 98 | 5 wt.-% |
| P2-5-B-4 | + | Kollidon VA64 | 1:12 | Brij 98 | 7.5 wt.-% |
| P2-5-B-5 | + | Kollidon VA64 | 1:12 | Brij 98 | 10 wt.-% |
| P2-5-C-1 | + | Kollidon VA64 | 1:16 | Brij 98 | 1 wt.-% |
| P2-5-C-2 | + | Kollidon VA64 | 1:16 | Brij 98 | 2.5 wt.-% |
| P2-5-C-3 | + | Kollidon VA64 | 1:16 | Brij 98 | 5 wt.-% |
| P2-5-C-4 | + | Kollidon VA64 | 1:16 | Brij 98 | 7.5 wt.-% |
| P2-5-C-5 | + | Kollidon VA64 | 1:16 | Brij 98 | 10 wt.-% |
| P2-5-D-1 | + | Kollidon VA64 | 1:20 | Brij 98 | 1 wt.-% |
| P2-5-D-2 | + | Kollidon VA64 | 1:20 | Brij 98 | 2.5 wt.-% |
| P2-5-D-3 | + | Kollidon VA64 | 1:20 | Brij 98 | 5 wt.-% |
| P2-5-D-4 | + | Kollidon VA64 | 1:20 | Brij 98 | 7.5 wt.-% |
| P2-5-D-5 | + | Kollidon VA64 | 1:20 | Brij 98 | 10 wt.-% |
| P2-5-E-1 | + | Kollidon VA64 | 1:24 | Brij 98 | 1 wt.-% |
| P2-5-E-2 | + | Kollidon VA64 | 1:24 | Brij 98 | 2.5 wt.-% |
| P2-5-E-3 | + | Kollidon VA64 | 1:24 | Brij 98 | 5 wt.-% |
| P2-5-E-4 | + | Kollidon VA64 | 1:24 | Brij 98 | 7.5 wt.-% |
| P2-5-E-5 | + | Kollidon VA64 | 1:24 | Brij 98 | 10 wt.-% |

Prophetic Examples

Prophetic examples of pharmaceutical dosage forms according to the invention are provided in the following Table 34. Their compositions are intended to be exemplary and it should be understood that the ingredients, the amount thereof and the procedure to obtain the dosage form may be varied.

For example, the ingredients of the following examples may be split up into intragranular and extragranular ingredients as well as ingredients from which a granulating solution is formed in order to process dosage forms by fluid bed granulation according to inventive example 1; or they may be processed by an alternative process, such as dry granulation or direct compression.

TABLE 34

| Ingredients [mg] | PE-1 | PE-2 | PE-3 | PE-4 | PE-5 | PE-6 |
|---|---|---|---|---|---|---|
| Lactose Monohydrate | 69.65 | 69.65 | 64.00 | 64.00 | 59.65 | 59.65 |
| Avicel ® (PH101 or PH 102) | 20.00 | 20.00 | 25.00 | 25.00 | 30.00 | 30.00 |
| Croscarmellose sodium | 3.00 | 3.00 | 2.50 | 2.50 | 3.00 | 3.00 |
| Compound (I'b) | 0.60 | 0.60 | 0.30 | 0.30 | 0.60 | 0.60 |
| Polyvinyl pyrrolidone | 5.00 | 5.00 | 5.50 | 5.50 | 5.00 | 5.00 |
| Sodium cetylstearyl sulfate | 1.00 | — | 2.00 | — | 1.00 | — |
| Sodium dioctylsulfosuccinate | — | 1.00 | — | 2.00 | — | 1.00 |
| Magnesium stearate | 0.75 | 0.75 | 0.70 | 0.70 | 0.75 | 0.75 |

Non-Prophetic Examples

The following examples further illustrate the invention but are not to be construed as limiting its scope.

Example 13

Pharmaceutical dosage forms were manufactured by fluid bed granulation according to the following compositions:

TABLE 35

| Ingredients | content (dosage: 40 µg) | | content (dosage: 600 µg) | |
|---|---|---|---|---|
| | wt.-% | amount per tablet [mg] | % (w/w) | amount per tablet [mg] |
| Intragranular | | | | |
| Lactose Monohydrate (200M) | 50.21 | 50.21 | 49.65 | 49.65 |
| Lactose Monohydrate (100M) | 20.00 | 20.00 | 20.00 | 20.00 |
| Avicel ® PH101 | 10.00 | 10.00 | 10.00 | 10.00 |
| Croscarmellose sodium | 1.50 | 1.50 | 1.50 | 1.50 |
| Granulating Solution | | | | |
| Compound (I'b) | 0.04 | 0.04 | 0.6 | 0.6 |
| Polyvinylpyrrolidone | 5.00 | 5.00 | 5.00 | 5.00 |
| Sodium Lauryl Sulphate | 1.00 | 1.00 | 1.00 | 1.00 |
| Purified water | — | — | | |
| Extragranular | | | | |
| Croscarmellose sodium | 1.50 | 1.50 | 1.50 | 1.50 |
| Avicel ® PH102 | 10.00 | 10.00 | 10.00 | 10.00 |
| Magnesium stearate | 0.75 | 0.75 | 0.75 | 0.75 |

Avicel ® PH101 and Avicel ® PH102 are microcrystalline celluloses with different mean particle sizes (50 and 100 microns). Purified water was used as part of the granulating fluid, but was removed during the granulation process.

General Procedure

For the fluid bed granulation process, all intragranular ingredients [lactose monohydrate (200 M and 100 M), Avicel® PH101, croscarmellose sodium] were weighed out and screened through a 710 micron screen into a 5 L Pharmatech shell. The material was then blended for 10 minutes at 25 rpm using a Pharmatech blender. The granulating solution was prepared by dissolving sodium lauryl sulfate in 600 g of purified water. 400 g of the corresponding solution was then used for dissolving the pharmacologically active agent according to formula (I') (1,1-(3-methylamino-3-phenylpentamethylene)-6-fluoro-1,3,4,9-tetrahydropyrano[3,4-b]indole (trans)) and the binder (polyvinylpyrrolidone) to form a drug suspension. The drug suspension was top sprayed over the intragranular material at a suitable rate using the Diosna minilab machine to yield compressible granules. The compressible granules were then added to the extragranular ingredients (croscarmellose sodium, Avicel® PH102, magnesium stearate) and mixed. Compression into tablets was then performed on a single punch Manesty F3 compression machine using a 6.00 mm NCCP tooling. The tablets were coated by means of the polyvinyl alcohol-based coating system OPADRY® AMB.

For dosage 50 µg, the determined content of the decomposition product 6'-fluoro-4-phenyl-4',9'-dihydro-3'H-spiro[cyclohex-3-ene-1,1-pyrano[3,4-b]indole] after storage at 25° C. and 60% rh as well as after storage at 40° C. and 75% RH was <0.1% after 6 months.

Example 14

Clinical studies were conducted to determine the analgesic efficacy and tolerability of single doses of the compound according to formula (I'b) (200 µg, 400 µg and 600 µg, based on the content of the free base; hemicitrate oral solution of compound (I'b) in Macrogol 400) compared to that of morphine (60 mg, controlled-released form) and placebo in patients with acute post-operative pain following orthopedic surgery (bunionectomy).

For this purpose, 258 patients of either sex were included in a randomized, placebo-controlled, double-blind clinical trial in parallel groups. Treatment groups were well-balanced with respect to demographics and baseline characteristics with a slight imbalance in baseline pain and ethnicity.

After surgery, all patients were initially treated with local post-operative anesthesia via a popliteal block. Due to different kinetics of the compound according to formula (I'b) and morphine, the patients were then treated with either one of the two drugs or with placebo at slightly different times:

One hour before the popliteal block was stopped, patients were randomized and part of them were dosed with a single dose of the compound according to formula (I'b) (200 µg, 400 µg or 600 µg) or placebo, while the others received morphine or placebo 2 hours after the popliteal block had been stopped.

The primary efficacy assessment endpoint was the absolute pain intensity over a 24 hour period. Pain intensity was measured using an 11-point numerical rating scale (NRS). At each time point, patients were instructed to evaluate their current pain intensity relative to an 11-point numerical rating scale. A score of zero represented no pain and a score of 10 represented worst possible pain. Missing scheduled pain assessments for the patients were imputed with the last observation carried forward (LOCF). The resulting averaged NRS values over the 24 hour period are depicted in FIG. 1.

Sum of pain intensity differences over different time periods were analyzed using an analysis of covariance (ANCOVA) model with factors for treatment and site and baseline pain intensity score (using the pain intensity NPRS score). Only subjects with non-missing baseline pain intensity were included. A summary of the analysis for the 2 to 10 hour period is presented in Table 36. The resulting p-values are summarized in Table 37.

TABLE 36

| | n | LS mean | SE | LS mean Δplacebo | SE | P-value |
|---|---|---|---|---|---|---|
| placebo | 45 | 49.13 | 2.85 | | | |
| compound (I'b) 200 µg | 52 | 46.05 | 2.78 | −3.08 | 3.49 | 0.3776 |
| compound (I'b) 400 µg | 47 | 35.28 | 2.81 | −13.85 | 3.57 | 0.0001 |
| compound (I'b) 600 µg | 55 | 35.15 | 2.67 | −13.98 | 3.45 | <0.0001 |
| morphine, controlled-release 60 mg | 49 | 42.01 | 2.83 | −7.12 | 3.54 | 0.0454 |

LS mean: least squares means; SE: statistical error

TABLE 37

| | p-values (sum of pain intensity differences) | | | | | |
|---|---|---|---|---|---|---|
| | 2-6 h | 2-10 h | 2-12 h | 2-14 h | 2-18 h | 2-24 h |
| compound (I'b) 200 μg | 0.4514 | 0.3776 | 0.3387 | 0.3427 | 0.3205 | 0.2923 |
| compound (I'b) 400 μg | 0.0009 | 0.0001 | <0.0001 | 0.0001 | 0.0005 | 0.0008 |
| compound (I'b) 600 μg | 0.0009 | <0.0001 | <0.0001 | <0.0001 | <0.0001 | 0.0001 |
| morphine, controlled-release 60 mg | 0.4664 | 0.0454 | 0.0084 | 0.0036 | 0.0014 | 0.0005 |

Accordingly, on the primary parameter, a statistically significant difference was observed between groups that had received a 400 μg or 600 μg dose of compound (I'b) and placebo groups, whereas no statistically significant difference was observed for groups that had received a 200 μg dose of compound (I'b).

Tables 38 and 39 summarize the treatment emergent adverse events (TEAE(s)) experienced by the five treatment groups.

TABLE 38

| | Placebo | compound (I'b) 200 μg | compound (I'b) 400 μg | compound (I'b) 600 μg | morphine 60 mg |
|---|---|---|---|---|---|
| subjects with TEAE(s) (n (%)) | 32 (68.1) | 37 (67.3) | 38 (77.6) | 48 (84.2) | 46 (92.0) |
| related (n (%)) | 17 (36.2) | 24 (43.6) | 32 (65.3) | 43 (75.4) | 42 (84.0) |
| serious (n (%)) | 1 (2.1) | 0 | 0 | 0 | 0 |
| total number of TEAE's (n) | 74 | 75 | 125 | 198 | 144 |
| related (n (%)) | 32 (43.2) | 37 (49.3) | 74 (59.2) | 146 (73.7) | 99 (68.8) |
| subjects with SAE's | 1 (2.1) | 0 | 0 | 0 | 0 |
| Deaths | 0 | 0 | 0 | 0 | 0 |

TEAE: treatment emergent adverse event;
SAE: serious adverse event

TABLE 39

| | Placebo | compound (I'b) 200 μg | compound (I'b) 400 μg | compound (I'b) 600 μg | morphine 60 mg |
|---|---|---|---|---|---|
| Nausea | 17.0 | 29.1 | 49.0 | 64.9 | 66.0 |
| Vomiting | 2.1 | 9.1 | 20.4 | 49.1 | 40.0 |
| Dizziness | 6.4 | 20.0 | 22.4 | 26.3 | 24.0 |
| Somnolence | 2.1 | 1.8 | 10.2 | 14.0 | 16.0 |
| ASAT increased | 2.1 | 1.8 | 6.1 | 1.8 | 2.0 |
| Hot flush | 0 | 1.8 | 4.1 | 7.0 | 4.0 |
| Pruritus | 0 | 0 | 6.1 | 3.5 | 2.0 |
| Hyperhidrosis | 0 | 0 | 0 | 5.3 | 6.0 |

100% = total number of subjects in corresponding treatment group;
ASAT: aspartate aminotransferase It becomes evident from Tables 38 and 39 that all four active treatments were well tolerated under these circumstances and the adverse events that showed up most frequently are in line with what can be expected from μ-opioid receptor agonists. For the patient group that had been treated with compound (I'b), the incidence of adverse events increased with the dose, and at a dose of 600 µg the incidence of adverse events was comparable to that of the morphine patient group.

Example 15

Clinical studies were conducted to determine the bioavailability of a tablet formulation containing compound (I'b) in a dose strength of 400 µg compared to a hemicitrate oral solution of compound (I'b) (400 µg, 400 µg/mL oral solution) in a Macrogol 400 formulation after single oral administration. 24 healthy white male subjects were included in a randomized, open-label, 3-way crossover, single-center clinical trial. The main pharmacokinetic parameters were $AUC_{0-t}$, $AUC_{0-72h}$ and $C_{max}$.

The results are summarized in Tables 40 to 42.

TABLE 40

| pharmacokinetic parameter | $t_{max}$ [h] | $C_{max}$ [pg/mL] | $AUC_{0-72\,h}$ [h · pg/mL] | $AUC_{0-t}$ [h · pg/mL] |
|---|---|---|---|---|
| 400 µg/mL oral solution | 6.00 (2.08; 6.00) | 120 ± 45.9 (38.3%) | 2861 ± 1251 (43.7%) | 4148 ± 2773 (66.8%) |
| 400 µg Tablet | 6.00 (3.50; 10.0) | 135 ± 52.5 (38.8%) | 3066 ± 1225 (40.0%) | 4501 ± 2658 (59.1%) |

N = 22;
The table presents the arithmetic means +/− the standard deviation (coefficient of variation).

TABLE 41

| Comparison tablets/oral solution | $C_{max}$ | $AUC_{0-72\,h}$ | $AUC_{0-t}$ |
|---|---|---|---|
| 400 µg tablet / 400 µg/mL oral solution | 108% (101%-118%) | 108% (102%-115%) | 110% (103%-118%) |

TABLE 42

| | total number of subjects | Subjects with TEAE(s) | | TEAE(S) |
|---|---|---|---|---|
| | (N) | n | % | e |
| 400 µg tablet | 23* | 14 | 60.9 | 21 |
| 400 µg/mL oral solution | 24 | 19 | 79.2 | 40 | n: number of subjects with at least one TEAE (treatment emergent adverse event);
%: corresponding ratio of subjects experiencing TEAE(s);
e: number of TEAE(s);
*1-drop out due to unrelated adverse event Accordingly, the relative bioavailability of the 400 µg tablet and 400 µg/mL oral solution based on $AUC_{0-72h}$ was 108%, with 90%-CI within the 80% to 125% range used for assessing bioequivalence.

The relative bioavailability of the 400 µg tablet and 400 µg/mL oral solution based on $C_{max}$ was also 108%, with 90%-CI within the 80% to 125% range used for assessing bioequivalence.

Single oral dose administrations of 400 µg of compound (I'b) were safe and well tolerated independent from the galenic formulation. No serious adverse events occurred.

Example 16

Clinical studies were conducted to determine the analgesic efficacy and tolerability of multiple doses of compound (I'b) (40 µg, 80 µg, 100 µg, 120 µg and 200 µg; all dosages as weight equivalent dosages relative to the free base, in the form of the hemicitrate,) compared to that of morphine (60 mg, controlled-release) and placebo in patients with painful diabetic neuropathy.

For this purpose, 86 patients of either sex were included in a randomized, placebo- and dose-controlled, double-blind, triple-crossover clinical trial in parallel groups.

Three studies with a randomized, double-blind, and crossover design were conducted:
Study A: Each patient received 2 different doses of compound (I'b) (40 and 120 µg) and placebo.
Study B: Each patient received 2 different doses of compound (I'b) (80 and 200 µg) and placebo.
Study C: Each patient received 100 µg of compound (I'b), 60 mg morphine and placebo.

Due to CA request to administer the 'high dose' only after exposure of the 'low dose', in studies A and B only three out of six possible sequences were applied, whereas in study C all six sequences were used with a double dummy administration.

In the first 14 to 18 days of the studies, patients did not receive any treatment in order to wash out any drugs from former treatment. At the end of this initial phase, pain intensities were determined and patients were randomized to one of the possible sequences. Then, each patient received dose preparations containing the respective dose of compound (I'b), morphine or placebo once daily for 5 days. This phase was followed by an 8 to 10 days long wash-out phase. The remaining two dose preparations were administered accordingly, i.e. once daily for 5 days followed by a wash-out phase (8 to 10 days).

All treatment groups were well-balanced with respect to demographics and baseline characteristics, only distribution of gender showed relevant variations.

Figure 7:
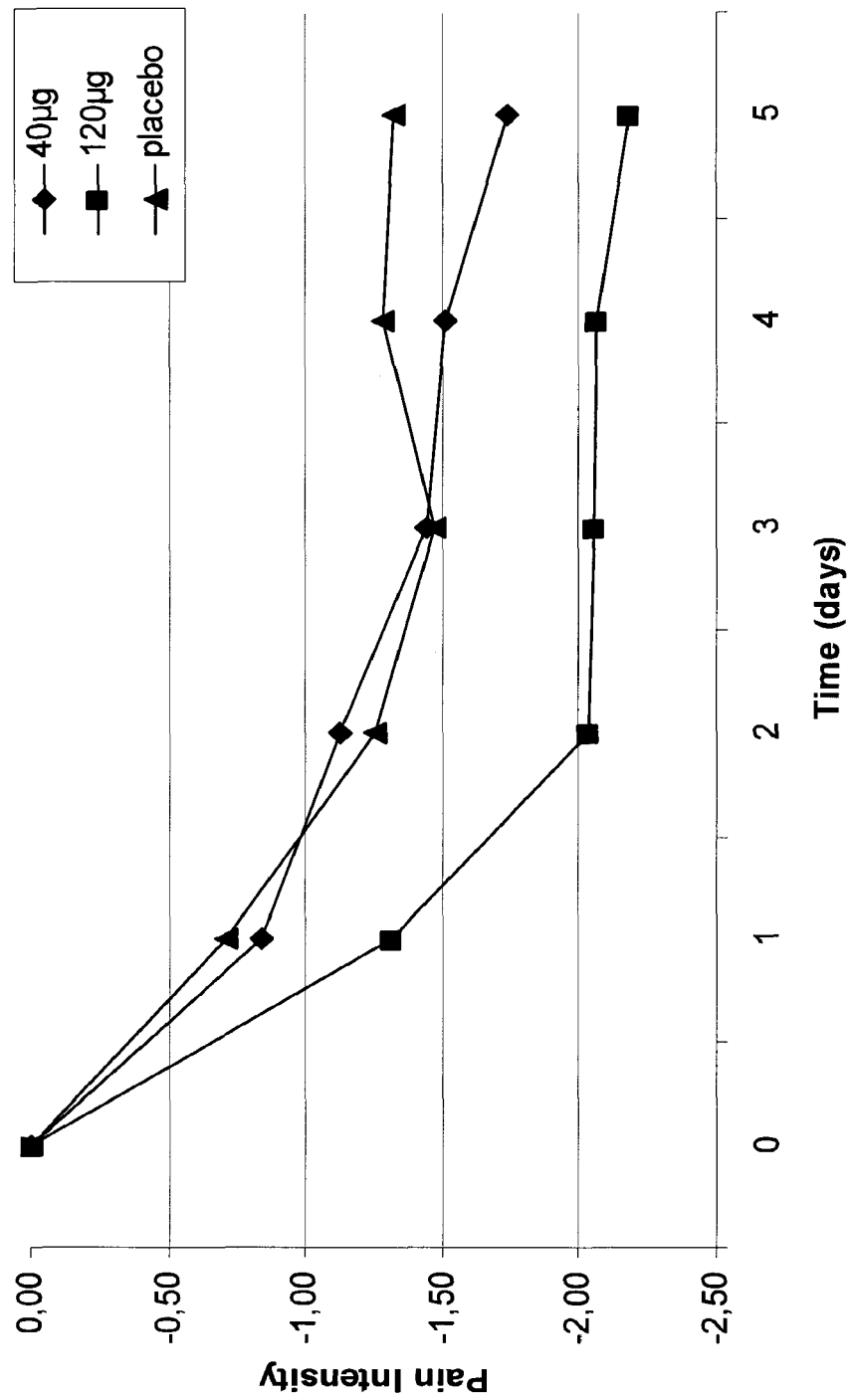
FIG. 7 shows the average daily pain changes (change of NRS value) over a 5-day period after administration of daily doses of the compound according to formula (I'b) (40 μg, 120 μg) compared to placebo in patients with painful diabetic neuropathy.
Figure 8:
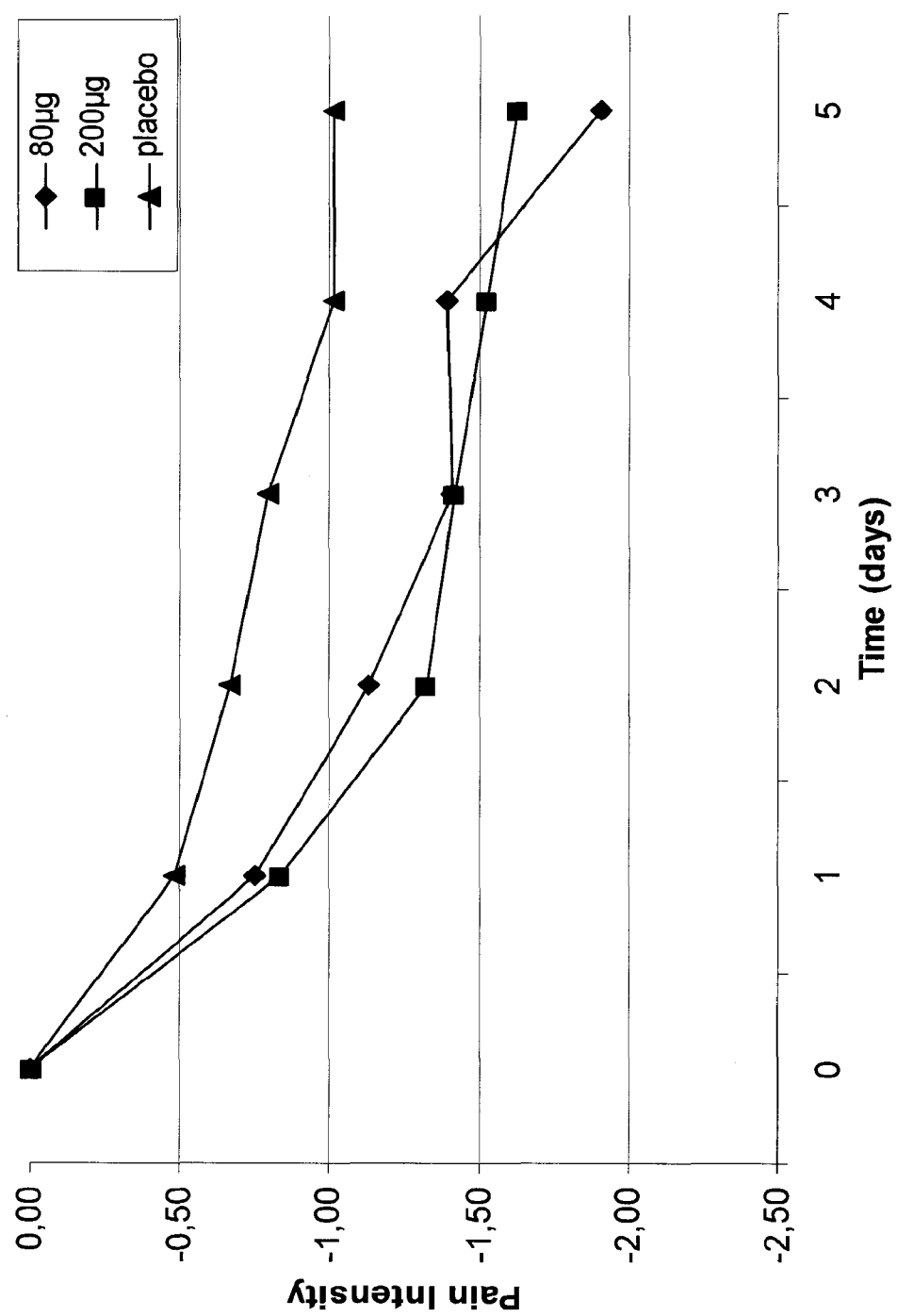
FIG. 8 shows the average daily pain changes (change of NRS value) over a 5-day period after administration of daily doses of the compound according to formula (I'b) (80 μg, 200 μg) compared to placebo in patients with painful diabetic neuropathy.
Figure 9:
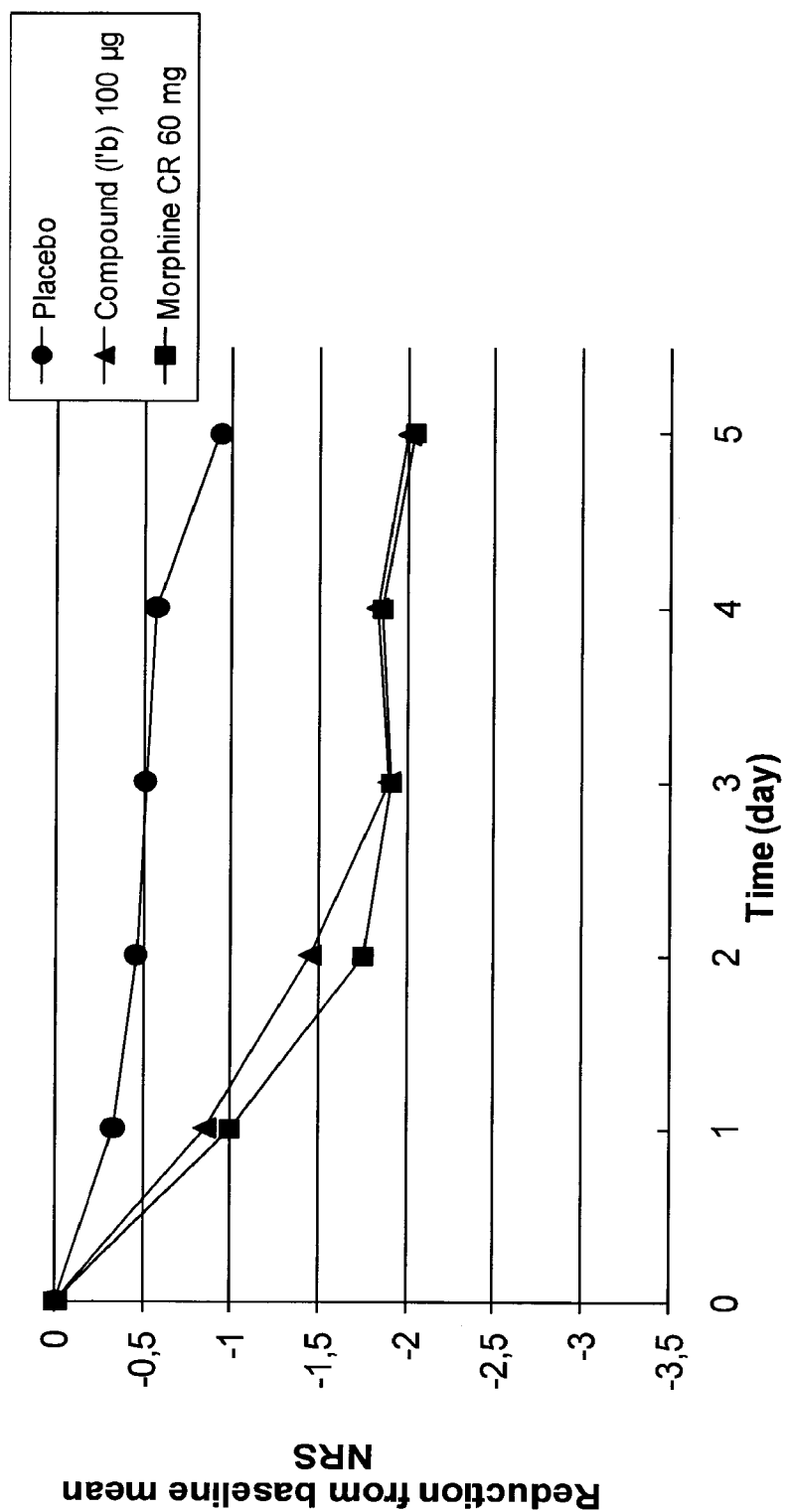
FIG. 9 shows the average daily pain changes (change of NRS value) over a 5-day period after administration of daily doses of the compound according to formula (I'b) (100 μg) compared to placebo and morphine slow release (60 mg) in patients with painful diabetic neuropathy.

The primary endpoint criterion was the reduction from baseline in average pain intensity score over the last 24 hours measured with the 11-point numerical rating scale (NRS) at the final treatment day of each treatment period, in comparison to placebo. Pain assessments were done 5 times a day starting at 7 h a.m. almost every 4 hours. At each time point, patients were instructed to evaluate their current pain intensity relative to the 11-point numerical rating scale via e-diary. A score of zero represented no pain and a score of 10 represented worst possible pain. Missing scheduled pain assessments for the patients were imputed with the last observation carried forward (LOCF). The resulting average daily pain changes (average change of the NRS value) over the 5-day treatment periods are depicted in FIGS. 7 to 9.

Pain intensity changes from the period baseline and the overall baseline were analyzed using descriptive statistics and an analysis of covariance (ANCOVA) model with factors for treatment and site effects, treatment sequence and period effects, and baseline pain effects. For studies A and C a period effect was identified. A summary of the descriptive statistic and ANCOVA analyses is presented in Tables 43, 44 and 45.

TABLE 43

| | Change from period baseline | | Change from overall baseline | |
|---|---|---|---|---|
| Treatment | descriptive statistics | ANCOVA | descriptive statistics | ANCOVA |
| Placebo | −1.32 | −1.62 | −1.65 | −1.93 |
| 40 µg compound (I'b) | −1.74 | −2.25 (p = 0.1217) | −1.63 | −2.37 (p = 0.2647) |

TABLE 43-continued

| | | | | |
|---|---|---|---|---|
| 120 µg compound (I'b) | −2.18 | −1.78 (p = 0.7173) | −2.55 | −2.04 (p = 0.7954) |
| TRT effect: | | p = 0.2979 | | p = 0.5334 |
| TRT sequence effect: | | p = 0.7052 | | p = 0.4140 |
| Period effect: | | p = 0.0002 | | p = 0.0002 |
| Baseline pain effect: | | p = 0.0055 | | p = 0.0053 |
| Centre (site) effect: | | p = 0.0277 | | p = 0.1982 |

TABLE 44

| | Change from period baseline | | Change from overall baseline | |
|---|---|---|---|---|
| Treatment | descriptive statistics | ANCOVA | descriptive statistics | ANCOVA |
| Placebo | −1.01 | −0.99 | −1.51 | −1.54 |
| 80 µg compound (I'b) | −1.91 | −1.78 (p = 0.073) | −2.35 | −2.39 (p = 0.048) |
| 200 µg compound (I'b) | −1.63 | −1.78 (p = 0.076) | −2.74 | −2.68 (p = 0.010) |
| TRT effect: | | p = 0.0836 | | p = 0.0156 |
| TRT sequence effect: | | p = 0.6471 | | p = 0.6079 |
| Period effect: | | p = 0.7325 | | p = 0.8158 |
| Baseline pain effect: | | p = 0.3784 | | p = 0.0781 |

TABLE 45

| | Change from period baseline | | Change from overall baseline | |
|---|---|---|---|---|
| Treatment | descriptive statistics | ANCOVA | descriptive statistics | ANCOVA |
| Placebo | −0.93 | −1.0 | −1.59 | −1.5 |
| 100 µg compound (I'b) | −2.01 | −1.9 (p = 0.0034) | −2.07 | −2.0 (p = 0.1118) |
| 60 µg morphine | −2.04 | −2.2 (p < 0.0001) | −2.27 | −2.5 (p = 0.0035) |
| TRT effect: | | p = 0.0003 | | p = 0.013 |
| TRT sequence effect: | | p = 0.1674 | | p = 0.1803 |
| Period effect: | | p = 0.0769 | | p = 0.0004 |
| Baseline pain effect: | | p = 0.0600 | | p = 0.2223 |

According to these results, on the parameter 'mean daily pain intensity change from baseline', all groups that had received compound (I'b) in the range of 80 µg to 200 µg showed statistically significant differences to placebo (except the 120 µg group, most likely due to a strong sequence of treatment effect). For these doses, separation from placebo starts at day 1 of administration with increasing effect over 5 consecutive days of daily administration. It becomes evident from Table 10 and FIG. 9 that for the 100 µg dose of compound (I'b), the analgesic effect was similar to that of 60 mg morphine. Further, it becomes evident from FIG. 7 that the effect of 40 µg dose of compound (I'b) did not differentiate from placebo from day 1 onwards, but differentiated from placebo on day 5.

This result is in agreement with the pharmacokinetic parameters that were measured in regular time intervals. The arithmetic and geometric means of the highest plasma concentration observed after administration of compound (I'b) on day 5 ($C_{max,\,5\,d}$) as well as of the arithmetic and geometric means of time needed to reach it after administration of this fifth consecutive daily dose ($t_{max,\,5\,d}$) are summarized in Table 11.

TABLE 46

| | arithmetic mean | | | geometric mean | | |
|---|---|---|---|---|---|---|
| dosage | $C_{max,\,5d}$ [pg/mL] | $C_{max,\,5d}$/dose [mL$^{-1}$] | $t_{max,\,5d}$ [h] | $C_{max,\,5d}$ [pg/mL] | $C_{max,\,5d}$/dose [mL$^{-1}$] | $t_{max,\,5d}$ [h] |
| 40 µg | 27.39 | 0.68 | 4.848 | 25.39 | 0.63 | 4.654 |
| 80 µg | 60.20 | 0.75 | 5.150 | 56.89 | 0.71 | 4.783 |
| 100 µg | 75.24 | 0.75 | 5.125 | 69.17 | 0.69 | 4.658 |
| 120 µg | 86.49 | 0.72 | 4.591 | 79.81 | 0.67 | 4.288 |
| 200 µg | 160.38 | 0.80 | 5.745 | 154.68 | 0.77 | 5.269 |

The results of the plasma concentrations measured at 0-3 h after administration on day 1, i.e. $C_{0\text{-}3h,\,1d}$, and at 0-3 h after administration on day 5, i.e. $C_{0\text{-}3h,\,5d}$, are displayed in Table 12 (mean±standard deviation, number of subjects N):

TABLE 47

| | mean | |
|---|---|---|
| dosage | $C_{0\text{-}3\,h,\,1\,d}$ [pg/mL] | $C_{0\text{-}3\,h,\,5\,d}$ [pg/mL] |
| 40 µg | 18.5 ± 18.1 (N = 23) | 14.8 ± 8.7 (N = 26) |
| 80 µg | 26.5 ± 15.4 (N = 21) | 40.3 ± 16.4 (N = 22) |
| 100 µg | 24.6 ± 19.7 (N = 33) | 49.1 ± 27.9 (N = 37) |
| 120 µg | 34.7 ± 25.8 (N = 26) | 50.0 ± 30.6 (N = 25) |
| 200 µg | 53.3 ± 40.1 (N = 22) | 105.2 ± 34.6 (N = 22) |

Table 48 summarizes the plasma concentrations that were measured at different points in time during the five days administration regimen:

TABLE 48

| | arithmetic mean [pg/ml] | | | | geometric mean [pg/ml] | | | |
|---|---|---|---|---|---|---|---|---|
| | 0.5-3 h | | 3-8 h | | 0.5-3 h | | 3-8 h | |
| dosage | day 1 | day 5 | day 3 | day 5 | day 1 | day 5 | day 3 | day 5 |
| 40 µg | 18.47 | 14.84 | 23.42 | 26.83 | 13.53 | 12.69 | 21.40 | 24.66 |
| 80 µg | 26.46 | 40.33 | 56.87 | 58.56 | 21.61 | 37.00 | 55.22 | 55.36 |
| 100 µg | 24.58 | 49.14 | 74.03 | 72.79 | 18.02 | 42.41 | 66.13 | 66.64 |
| 120 µg | 34.64 | 49.97 | 78.46 | 84.65 | 24.51 | 41.47 | 72.84 | 78.10 |
| 200 µg | 53.33 | 105.21 | 153.31 | 154.27 | 40.00 | 99.43 | 148.86 | 147.69 |
| dosage morphine controlled release | | | | | | | | |
| 60 mg | 5.00 | 7.39 | 9.54 | 11.36 | 3.83 | 6.20 | 7.70 | 9.87 |

FIG. 10 shows a comparison of the mean $C_{max}$ values measured on day 5 in comparison to the plasma concentration that was observed before the next dose was administered ($C_{next\,predose}$), i.e. 8 to 10 days after administration of the fifth dose at the end of the wash-out phase.

It is evident from FIG. 10 that samples taken 8-10 days after previous treatment with compound (I'b) still contained this drug in detectable (and statistically relevant) concentrations. Even samples taken 10-15 days after previous treatment with compound (I'b) still had concentrations >2.0 pg/mL.

Tables 49 and 50 summarize the treatment emergent adverse events (TEAE(s)) experienced by the treatment groups.

It is evident from Tables 49 and 50 that doses up to 120 μg of compound (I'b) had a incidence of treatment emergent adverse events (TEAEs) similar to placebo with the exception of dizziness which was reported more frequently compared to placebo at all doses examined. Typical adverse events expected from μ-opioid receptor agonists were starting to be present only at the top dose of 200 μg. There were clearly more TEAEs reported following administration of 60 mg Morphine compared to 100 μg of compound (I'b) paired with a comparable analgesic efficacy (cf. Table 10 and FIG. 9).

The foregoing description and examples have been set forth merely to illustrate the invention and are not intended to be limiting. Since modifications of the described embodi-

TABLE 49

| | Population | | | | | | | | |
|---|---|---|---|---|---|---|---|---|---|
| | Placebo Study A | Placebo Study B | Placebo Study C | 40 μg Study A | 80 μg Study B | 100 μg Study C | 120 μg Study A | 200 μg Study B | 60 mg Morphine Study C |
| Total number of subjects | 26 | 23 | 36 | 26 | 23 | 37 | 26 | 23 | 36 |
| Subjects with TEAEs | 17 (65.4%) | 16 (69.6%) | 25 (69.4%) | 21 (80.8%) | 16 (69.6%) | 27 (73%) | 17 (65.4%) | 19 (82.6%) | 34 (94.4%) |
| Total number of TEAEs[a] | 62 (34) | 42 (21) | 69 (57) | 65 (39) | 53 (24) | 91 (52) | 54 (36) | 91 (76) | 209 (156) |
| Number of serious TEAEs | 0 | 0 | 1* | 0 | 0 | 0 | 0 | 0 | 0 |
| Number of events leading to withdrawal | 0 | 0 | 1 | 0 | 0 | 0 | 0 | 0 | 3 |

TEAEs[a]: treatment emergent adverse event (at least possibly related);
*vitreous heamorrhage, patient with medical history of diabetic retinopathy

TABLE 50

| TEAEs (%) | Placebo Study A | Placebo Study B | Placebo Study C | 40 μg Study A | 80 μg Study B | 100 μg Study C | 120 μg Study A | 200 μg Study B | 60 mg Morphine Study C |
|---|---|---|---|---|---|---|---|---|---|
| Nausea | 19.2 | 17.4 | 16.7 | 26.9 | 13.0 | 13.5 | 23.1 | 39.1 | 47.2 |
| Headache | 23.1 | 17.4 | 5.6 | 34.6 | 13.0 | 8.1 | 23.1 | 17.4 | 25.0 |
| Dizziness | 11.5 | 13.0 | 11.1 | 26.9 | 26.1 | 18.9 | 23.1 | 34.8 | 19.4 |
| Constipation | 11.5 | 8.7 | 8.3 | 23.1 | 0 | 16.2 | 7.7 | 4.3 | 25.0 |
| Fatigue | 19.2 | 4.3 | 2.8 | 11.5 | 4.3 | 13.5 | 3.8 | 21.7 | 19.4 |
| Vomiting | 3.8 | 0 | 8.3 | 0 | 4.3 | 13.5 | 7.7 | 13.0 | 52.8 |
| Vision blurred | 0 | 4.3 | 0 | 0 | 4.3 | 2.7 | 0 | 13.0 | 0 |
| Visual impairment | 0 | 4.3 | 0 | 0 | 0 | 2.7 | 0 | 8.7 | 0 |
| Pruritus | 0 | 0 | 2.8 | 0 | 0 | 10.8 | 0 | 0 | 13.9 |
| Cold sweat | 0 | 0 | 0 | 0 | 8.7 | 2.7 | 0 | 4.3 | 0 |
| Hyperglycemia | 0 | 4.3 | 0 | 0 | 8.7 | 2.7 | 3.8 | 0 | 2.8 |
| ECG QT prolonged | 0 | 4.3 | 0 | 0 | 8.7 | 0 | 3.8 | 0 | 0 |
| Bacteriuria | 0 | 0 | 13.9 | 0 | 8.7 | 10.8 | 0 | 0 | 13.9 |
| Peripheral oedema | 3.8 | 0 | 2.8 | 7.7 | 0 | 0 | 3.8 | 0 | 0 |
| Oral discomfort | 3.8 | 0 | 0 | 7.7 | 0 | 0 | 0 | 0 | 0 |
| Oropharyngeal Pain | 3.8 | 0 | 2.8 | 0 | 0 | 5.6 | 0 | 0 | 8.1 |
| Dyspepsia | 3.8 | 4.3 | 2.8 | 7.7 | 4.3 | 5.4 | 0 | 0 | 2.8 |
| Back pain | 0 | 0 | 2.8 | 7.7 | 0 | 0 | 0 | 0 | 5.6 |

The invention claimed is:

1. A method of treating pain in a subject in need thereof, said method comprising administering to said subject once daily or less frequently a pharmaceutical dosage form which contains a pharmacologically active agent corresponding to formula (I')

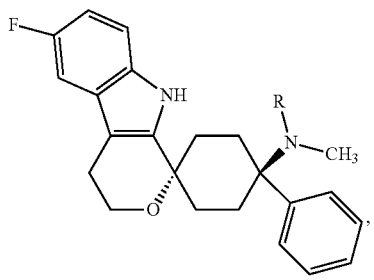

wherein R is —H or —CH$_3$,
or a physiologically acceptable salt thereof; and
wherein said dosage form provides a release profile in vitro of the pharmacologically active agent corresponding to formula (I'), such that under in vitro conditions in 900 mL artificial gastric juice at pH 1.2 and 37±0.5° C. according to the paddle method with sinker at 100 rpm, said dosage form has released at least 50 wt.-% of the pharmacologically active agent corresponding to formula (I') after 30 minutes, based on the total amount of the pharmacologically active agent originally contained in the pharmaceutical dosage form; and
wherein the pharmaceutical dosage form contains a surfactant having a hydrophilic-lipophilic balance (HLB) of at least 10.

2. A method according to claim 1, wherein the pain is selected from the group consisting of acute pain, visceral pain, neuropathic pain and chronic pain.

3. The method of claim 1, wherein said dosage form has a pharmacokinetic parameter $t_{max}$ within the range of from 2 to 10 hours.

4. The method of claim 1, wherein after once daily administration of the pharmaceutical dosage form to a subject for at least 5 consecutive days, said dosage form produces in said subject a highest plasma concentration of the pharmacological agent within the range from 10 to 120 μg/m$^3$.

5. The method of claim 1, wherein the pharmacologically active agent corresponding to formula (I') is (1r,4r)-6'-fluoro-N,N-dimethyl-4-phenyl-4',9'-dihydro-3'H-spiro[cyclohexane-1,1'-pyrano[3,4,b]indol]-4-amine, (1r,4r)-6'-fluoro-N-methyl-4-phenyl-4',9'-dihydro-3'H-spiro[cyclohexane-1,1'-pyrano[3,4,b]indol]-4-amine, or physiologically acceptable salt thereof.

6. The method of claim 1, wherein under in vitro conditions in 900 mL artificial gastric juice at pH 1.2 said dosage form releases after 30 minutes at least 80 wt.-% of the pharmacologically active agent corresponding to formula (I'), based on the total amount of the pharmacologically active agent corresponding to formula (I') originally contained in the dosage form.

7. The method of claim 1, wherein
the pharmacokinetic parameter $t_{max}$ is within the range of from 0.5 to 16 hours; and/or
the ratio of the pharmacokinetic parameter AUC$_{0-t}$/dose is within the range of from 0.3 to 20 h/m$^3$; and/or
the ratio of the pharmacokinetic parameter C$_{max}$/dose is within the range of from 0.06 to 1.69 m$^{-3}$.

8. The method of claim 4, wherein the time to reach the highest plasma concentration of the pharmacological agent reached after once daily administration of the pharmaceutical dosage form for at least 5 consecutive days is within the range of from 2 to 6 hours.

9. The method of claim 1, wherein said dosage form contains the pharmacologically active agent corresponding to formula (I') in a dose of from 200 μg to 600 μg.

10. The method of claim 1, wherein the pharmacologically active agent corresponding to formula (I') is (1r,4r)-6'-fluoro-N,N-dimethyl-4-phenyl-4',9'-dihydro-3'H-spiro[cyclohexane-1,1'-pyrano[3,4,b]indol]-4-amine, or physiologically acceptable salt thereof.

11. The method of claim 1, wherein the pharmacologically active agent corresponding to formula (I') is (1r,4r)-6'-fluoro-N,N-dimethyl-4-phenyl-4',9'-dihydro-3'H-spiro[cyclohexane-1,1'-pyrano[3,4,b]indol]-4-amine.

12. The method of claim 1, wherein said dosage form further comprises a disintegrant, and wherein said dosage form disintegrates in 5 minutes or less following exposure to a disintegrating medium.

13. The method of claim 12, wherein the disintegrant is croscarmellose sodium, cross-linked polyvinyl pyrrolidone or sodium starch glycolate.

14. The method of claim 12, wherein the content of the disintegrant is within the range of from 0.001 to 5 wt. % relative to the total weight of the dosage form.

15. The method of claim 12, wherein said dosage form disintegrates in 2 minutes or less following exposure to a disintegrating medium.

16. The method of claim 1, wherein the surfactant has the general formula (IIa)

$$C_nH_{2n+1}O-SO_3^-M^+ \quad\quad\quad (II\text{-}a),$$

wherein n is an integer of from 8 to 30 and M is selected from Li$^+$, Na$^+$, K$^+$, NH$_4^+$ ½Mg$^{2+}$ or ½Ca$^{2+}$.

17. The method of claim 1, wherein the surfactant is selected from the group consisting of sodium glycocholate, sodium taurocholate, sodium lauryl sulfate, sodium cetyl sulfate, sodium cetylstearyl sulfate, sodium stearyl sulfate, sodium dioctylsulfosuccinate, and corresponding salts thereof.

18. The method of claim 1, wherein the content of the surfactant is at least 0.001 wt.-%, based on the total weight of the pharmaceutical dosage form.

19. The method of claim 17, wherein the content of the surfactant is 0.25 wt.-% to 5 wt.-%, based on the total weight of the pharmaceutical dosage form.

20. The method of claim 1, wherein the surfactant is sodium lauryl sulfate, and wherein surfactant content is 1 wt.-%, relative to the total weight of the dosage form.

21. The method of claim 1, wherein said dosage form contains the pharmacologically active agent corresponding to formula (I') in a dose of from 0.1 μg to 5000 μg.

22. The method of claim 1, wherein said dosage form contains the pharmacologically active agent corresponding to formula (I') in a dose of from 0.1 μg to 1000 μg.

23. The method of claim 1, wherein said dosage form contains the pharmacologically active agent corresponding to formula (I') in a dose of from 150 μg to 800 μg.

24. The method of claim 1, wherein said dosage form contains the pharmacologically active agent corresponding to formula (I') in a dose of 400±350 μg.

25. The method of claim 1, wherein
the pharmacokinetic parameter $t_{max}$ is within the range of 6±1.5 hours; and/or
the ratio of the pharmacokinetic parameter $AUC_{0-t}$/dose is within the range of 9.5 h/m³; and/or
the ratio of the pharmacokinetic parameter $C_{max}$/dose is within the range of 0.06±0.40 m⁻³.

26. The method of claim 1, wherein said dosage form is a tablet for oral administration.

27. The method of claim 1, wherein the content of the pharmacologically active agent in the pharmaceutical dosage form is at most 10 wt.-%.

28. The method of claim 1, wherein the surfactant having a HLB value of at least 10 is an anionic surfactant.

29. A method of treating pain in a subject in need thereof, said method comprising administering to said subject once daily or less frequently a pharmaceutical dosage form, which contains a pharmacologically active agent corresponding to formula (I')

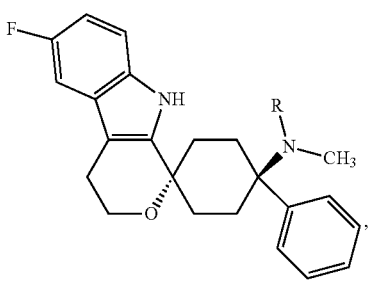

(I')

wherein R is —H or —CH₃,
or a physiologically acceptable salt thereof;
wherein said dosage form is a tablet for oral administration;
wherein the content of the pharmacologically active agent in the pharmaceutical dosage form is at most 10 wt.-%;
wherein said dosage form further comprises a surfactant having a HLB value of at least 10;
wherein said dosage form has released at least 50 wt.-% of the pharmacologically active agent corresponding to formula (I') after 30 minutes, based on the total amount of the pharmacologically active agent corresponding to formula (I') originally contained in the dosage form.

30. A method of treating pain in a subject in need thereof, said method comprising administering to said subject once daily or less frequently a pharmaceutical dosage form, which contains a pharmacologically active agent corresponding to formula (I')

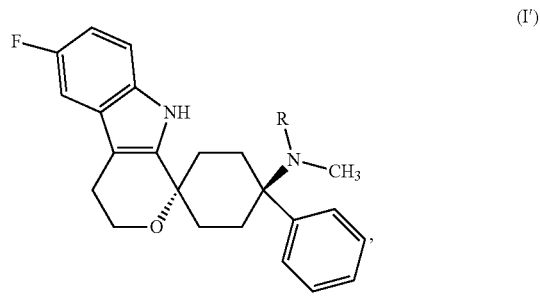

(I')

wherein R is —H or —CH₃,
or a physiologically acceptable salt thereof;
wherein said dosage form is a tablet for oral administration;
wherein the content of the pharmacologically active agent in the pharmaceutical dosage form is at most 10 wt.-%;
wherein said dosage form further comprises a surfactant having a HLB value of at least 10;
wherein said dosage form provides immediate release in vitro of the pharmacologically active agent corresponding to formula (I'), such that under in vitro conditions in 900 mL artificial gastric juice at pH 1.2 and 37±0.5° C. according to the paddle method with sinker at 100 rpm, said dosage form has released at least 50 wt.-% of the pharmacologically active agent corresponding to formula (I') after 30 minutes, based on the total amount of the pharmacologically active agent corresponding to formula (I') originally contained in the dosage form;
and wherein said dosage form further comprises a disintegrant, and wherein said dosage form disintegrates in 10 minutes or less following exposure to a disintegrating medium.

* * * * *